(12) United States Patent
Facchetti et al.

(10) Patent No.: US 9,666,805 B2
(45) Date of Patent: May 30, 2017

(54) BITHIOPHENE SULFONAMIDE-BASED MOLECULAR AND POLYMERIC SEMICONDUCTORS

(71) Applicants: Polyera Corporation, Skokie, IL (US); Northwestern University, Evanston, IL (US)

(72) Inventors: Antonio Facchetti, Chicago, IL (US); Tobin J. Marks, Evanston, IL (US); Yu Xia, Northbrook, IL (US); Martin Drees, Glenview, IL (US); Ferdinand Melkonyan, Chicago, IL (US); Wei Zhao, Skokie, IL (US)

(73) Assignees: Northwestern University, Evanston, IL (US); Flexterra, Inc., Skokie, IL (US)

( * ) Notice: Subject to any disclaimer, the term of this patent is extended or adjusted under 35 U.S.C. 154(b) by 0 days.

(21) Appl. No.: 14/951,628

(22) Filed: Nov. 25, 2015

(65) Prior Publication Data

US 2016/0149138 A1    May 26, 2016

Related U.S. Application Data

(60) Provisional application No. 62/084,535, filed on Nov. 25, 2014.

(51) Int. Cl.
| | | |
|---|---|---|
| *C07D 513/14* | (2006.01) |
| *C08G 75/06* | (2006.01) |
| *H01L 51/00* | (2006.01) |
| *C08G 61/12* | (2006.01) |
| *C09K 11/06* | (2006.01) |
| *H01L 51/05* | (2006.01) |
| *H01L 51/42* | (2006.01) |

(52) U.S. Cl.
CPC ........ *H01L 51/0036* (2013.01); *C07D 513/14* (2013.01); *C08G 61/122* (2013.01); *C08G 61/126* (2013.01); *C08G 75/06* (2013.01); *C09K 11/06* (2013.01); *H01L 51/0043* (2013.01); *H01L 51/0068* (2013.01); *H01L 51/0071* (2013.01); *C08G 2261/124* (2013.01); *C08G 2261/1424* (2013.01); *C08G 2261/3223* (2013.01); *C08G 2261/3243* (2013.01); *C08G 2261/344* (2013.01); *C08G 2261/364* (2013.01); *C08G 2261/414* (2013.01); *C08G 2261/92* (2013.01); *H01L 51/0558* (2013.01); *H01L 51/4253* (2013.01); *Y02E 10/549* (2013.01)

(58) Field of Classification Search
CPC .............. C07D 513/14; H01L 51/0036; H01L 51/0068; H01L 51/0043; C08G 75/06
USPC ............................................................. 544/33
See application file for complete search history.

(56) References Cited

U.S. PATENT DOCUMENTS 4,656,265 A * 4/1987 Lombardino ........ C07D 513/14
                                                          544/33
4,914,101 A * 4/1990 Marfat ................. C07D 513/04
                                                          514/229.8

\* cited by examiner

*Primary Examiner* — Kahsay Habte
(74) *Attorney, Agent, or Firm* — Karen K. Chan

(57) ABSTRACT

The present invention relates to new semiconducting compounds having at least one optionally substituted bithiophene sulfonamide moiety. The compounds disclosed herein can exhibit high carrier mobility and/or efficient light absorption/emission characteristics, and can possess certain processing advantages such as solution-processability and/or good stability at ambient conditions.

16 Claims, 8 Drawing Sheets

BITHIOPHENE SULFONAMIDE-BASED MOLECULAR AND POLYMERIC SEMICONDUCTORS

CROSS-REFERENCE TO RELATED APPLICATIONS

This application claims priority to and the benefit of U.S. Provisional Patent Application Ser. No. 62/084,535, filed on Nov. 25, 2014, the disclosure of which is incorporated by reference herein in its entirety.

STATEMENT REGARDING FEDERALLY SPONSORED RESEARCH OR DEVELOPMENT

This invention was made with government support under grant number DE-SC0001059 awarded by the Department of Energy. The government has certain rights in the invention.

BACKGROUND

Flexible, printed electronics is a revolutionary new concept for fabricating optoelectronic devices using high-throughput, inexpensive solution processes (e.g., printing methodologies) on flexible plastic foils, which contrasts sharply with the highly specialized and expensive facilities and equipment required for silicon fabrication. By developing new electronic materials, these technologies can enable inexpensive, lightweight, flexible, optically transparent, and unbreakable components for a wide variety of applications such as displays, cell phones, medical diagnostics, RFID tags, and solar modules, which then can be integrated with textiles, printed batteries, solar cells, aircraft or satellite structures, and the like. The enabling material component of all these technologies (among other essential materials) is the semiconductor where charge transport, light absorption, and/or light generation occur. To broaden device functionalities and applications, two types of semiconductors are required: p-type (hole-transporting) and n-type (electron-transporting). The use and combination of these two types of semiconductors enable the fabrication of elementary electronic building blocks for driving displays, harvesting light, generating light, carrying out logic operations, and sensor functions. To enable high device efficiencies such as large charge carrier mobilities ($\mu$) needed for transistor/circuit operations, or efficient exciton formation/splitting necessary for photonic devices, organic semiconductors should have an appropriate electronic structure to favor specific functions.

Several p- and n-channel molecular semiconductors have achieved acceptable device performance and stability. For example, OTFTs based on acenes and oligothiophenes (p-channel) and perylenes (n-channel) have reported carrier mobilities ($\mu$'s)>1 $cm^2$/Vs in ambient conditions. However, molecular semiconductors typically are less easily processable via printing methodologies than polymeric semiconductors due to solution viscosity requirements.

Accordingly, the art desires new molecular and polymeric semiconducting compounds, particularly those having good stability, processing properties, and/or charge transport characteristics in ambient conditions.

SUMMARY

In light of the foregoing, the present teachings provide organic semiconducting compounds that can address various deficiencies and shortcomings of the prior art, including those outlined above. Compounds according to the present teachings can exhibit properties such as optimized optical absorption, good charge transport characteristics and chemical stability in ambient conditions, low-temperature processability, large solubility in common solvents, and processing versatility (e.g., via various solution processes). As a result, optoelectronic devices such as OPV cells that incorporate one or more of the present compounds as a photoactive layer can exhibit high performance in ambient conditions, for example, demonstrating one or more of low band-gap, high fill factor, high open circuit voltage, and high power conversion efficiency, and preferably all of these criteria. Similarly, other organic semiconductor-based devices such as OTFTs can be fabricated efficiently using the organic semiconductor materials described herein.

Generally, the present teachings provide semiconducting compounds that include one or more divalent bithiophene sulfonamide moieties. Such divalent bithiophene sulfonamide moieties can be represented by formula (I):

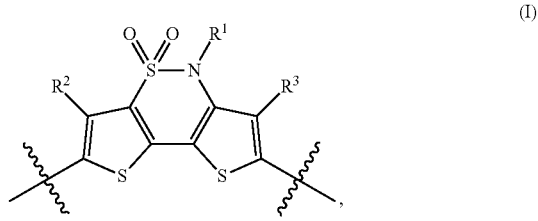

herein $R^1$, $R^2$, and $R^3$ are as defined herein.

In some embodiments, the present compound is a polymer having one or more repeating units $M_1$ each of which includes at least one bithiophene sulfonamide moiety, and where the polymer has a degree of polymerization (n) ranging from at least 3. In certain embodiments, the polymer is a homopolymer including only repeating units $M_1$. In other embodiments, the polymer also includes at least one other repeating unit $M_2$ that does not include any bithiophene sulfonamide moiety. For example, such $M_2$ unit can be selected from:

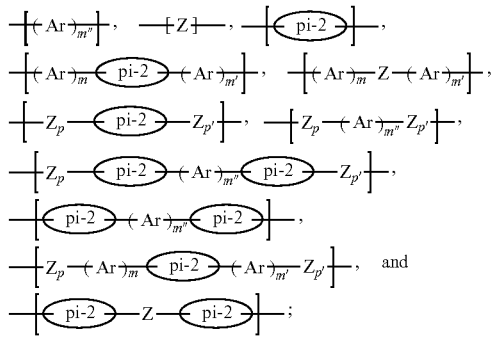

wherein pi-2, Ar, Z, m, m', m'', p, and p' are as defined herein.

In some embodiments, the present compound is a molecular compound including at least one bithiophene sulfonamide moiety and one or more linear and/or cyclic conjugated moieties, such that the compound as a whole provides a pi-extended conjugated system.

The present teachings also provide methods of preparing such compounds and semiconductor materials based on such compounds, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

FIG. 4a shows optical spectra of polymers P4 and P11 in $CHCl_3$ solutions (5 mg/mL). FIG. 4b shows optical absorption spectra of polymers P4 and P11 as films. Polymer films were deposited on a glass substrate by spin coating from $CHCl_3$ solutions.

FIG. 6a shows an optical spectrum of polymer P14 in a $CHCl_3$ solution (5 mg/mL). FIG. 6b shows a cyclic voltammogram of polymer P14.

FIG. 7a shows the current-voltage (JV) scan of the device. FIG. 7b shows the external quantum efficiency (EQE) curve of the device.

DETAILED DESCRIPTION

Figure 1:
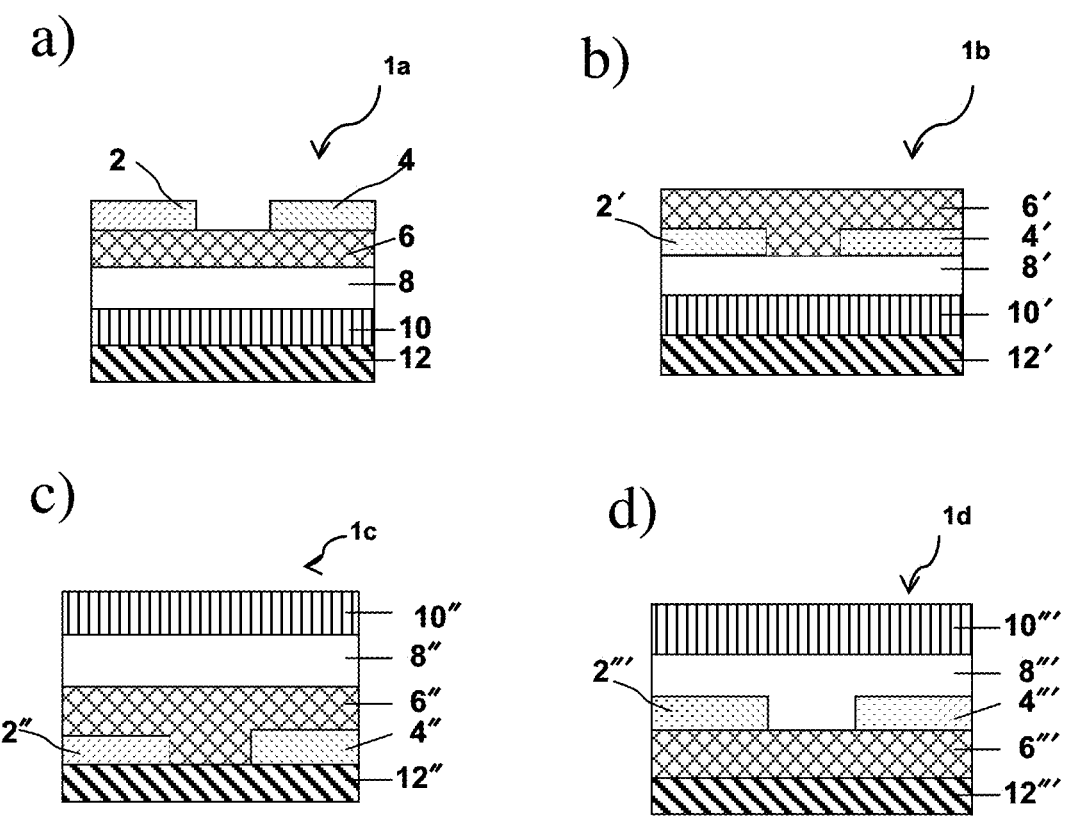
FIG. 1 illustrates four different configurations of thin film transistors: bottom-gate top contact (a), bottom-gate bottom-contact (b), top-gate bottom-contact (c), and top-gate top-contact (d); each of which can be used to incorporate compounds of the present teachings.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ $cm^2/Vs$. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ $cm^2/Vs$. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 0.60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from incident light to electrical power. The PCE of a solar cell can be calculated by dividing the maximum power point ($P_m$) by the input light irradiance (E, in $W/m^2$) under standard test conditions (STC) and the surface area of the solar cell ($A_c$ in $m^2$). STC typically refers to a temperature of 25° C. and an irradiance of 1000 $W/m^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "polymeric compound" (or "polymer") refers to a molecule including a plurality of one or more repeating units connected by covalent chemical bonds. A polymeric compound can be represented by the general formula:

wherein M is the repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units

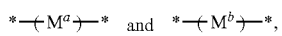

where $M^a$ and $M^b$ represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

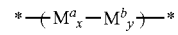

can be used to represent a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_n$) and/or weight average molecular weight ($M_w$) depending on the measuring technique(s)).

As used herein, "heteroatom" refers to an atom of any element other than carbon or hydrogen and includes, for example, nitrogen, oxygen, silicon, sulfur, phosphorus, and selenium.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_zH_{2z+1-t}X^0_t$, where $X^0$, at each occurrence, is F, Cl, Br or I, z is an integer in the range of 1 to 40, and t is an integer in the range of 1 to 81, provided that t is less than or equal to 2z+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. In embodiments where the cyclic moiety is a "polycyclic moiety," the "polycyclic moiety" can include two or more rings fused to each other (i.e., sharing a common bond) and/or connected to each other via a spiro atom. The cyclic moiety can be a cycloalkyl group, a heterocycloalkyl group, an aryl group, or a heteroaryl group (i.e., can include only saturated bonds, or can include one or more unsaturated bonds regardless of aromaticity), and can be optionally substituted as described herein. In embodiments where the cyclic moiety is a "monocyclic moiety," the "monocyclic moiety" can include a 3-20 membered carbocyclic or heterocyclic ring. A monocyclic moiety can include a $C_{6-20}$ aryl group (e.g., $C_{6-14}$ aryl group) or a 5-20 membered heteroaryl group (e.g., 5-14 membered heteroaryl group), each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 20 carbon atoms, for example, 3 to 14 carbon atoms (i.e., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5] decanyl groups, as well as their homologs, isomers, and the like. In some embodiments, cycloalkyl groups can be substituted as described herein.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 20 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 22 carbon atoms in its ring system (e.g., $C_{6-14}$ aryl group), which can include multiple fused rings. In some embodiments, a polycyclic aryl group can have from 8 to 22 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is as defined herein. An example of an arylalkyl group is a benzyl group (—CH$_2$—C$_6$H$_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, 5 to 22 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

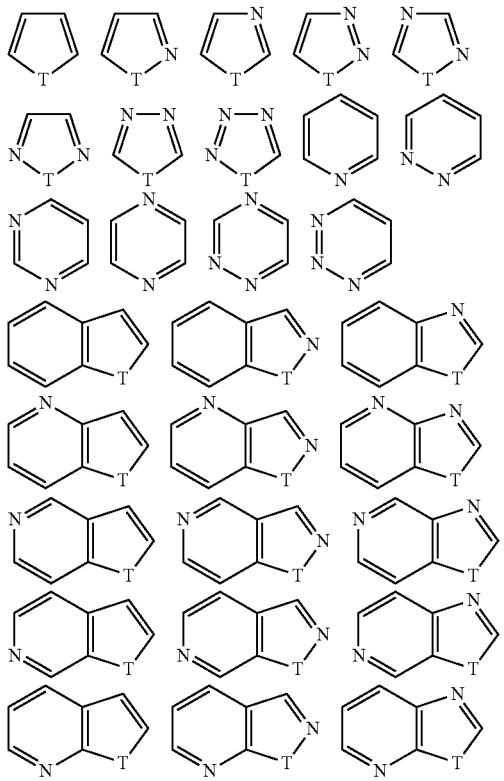

where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group), a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group).

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —NO$_2$, —CN, —NC, —S(R$^o$)$_2^+$, —N(R$^o$)$_3^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, —CON(R$^o$)$_2$, $C_{1-40}$ haloalkyl groups, $C_{6-14}$ aryl groups, and 5-14 membered electron-poor heteroaryl groups; where R$^o$ is a $C_{1-20}$ alkyl group, a $C_{2-20}$ alkenyl group, a $C_{2-20}$ alkynyl group, a $C_{1-20}$ haloalkyl group, a $C_{1-20}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein. For example, each of the $C_{1-20}$ alkyl group, the $C_{2-20}$ alkenyl group, the $C_{2-20}$ alkynyl group, the $C_{1-20}$ haloalkyl group, the $C_{1-20}$ alkoxy group, the $C_{6-14}$ aryl group, the $C_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —NO$_2$, —CN, —NC, —S(R$^o$)$_2^+$, —N(R$^o$)$_3^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, and —CON(R$^o$)$_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —OR⁰, —NH₂, —NHR⁰, —N(R⁰)₂, and 5-14 membered electron-rich heteroaryl groups, where $R^0$ is a $C_{1-20}$ alkyl group, a $C_{2-20}$ alkenyl group, a $C_{2-20}$ alkynyl group, a $C_{6-14}$ aryl group, or a $C_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents of monomers A and B are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that compounds of the present teachings encompass all possible regioisomers in pure form and mixtures thereof. It may be possible to separate such isomers, for example, using standard separation procedures known to those skilled in the art, for example, column chromatography, thin-layer chromatography, simulated moving-bed chromatography, and high-performance liquid chromatography. However, mixtures of regioisomers can be used similarly to the uses of each individual regioisomer of the present teachings.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

Throughout the specification, structures may or may not be presented with chemical names. Where any question arises as to nomenclature, the structure prevails.

The present teachings relate to molecular and polymeric compounds that can be used as organic semiconductor materials. The present compounds can have good solubility in various common organic solvents and good stability in air. When incorporated into optical, electronic or optoelectronic devices including, but not limited to, organic photovoltaic or solar cells, organic light emitting diodes, and organic field effect transistors, the present compounds can confer various desirable performance properties.

More specifically, the present teachings provide semiconducting compounds that include one or more optionally substituted bithiophene sulfonamide moieties. The optionally substituted bithiophene sulfonamide moieties can be represented by formula (I):

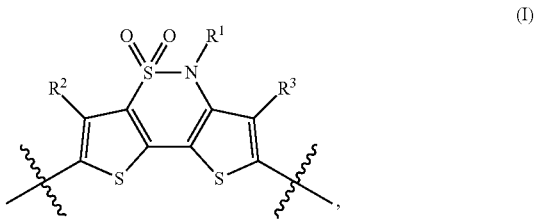

wherein $R^1$, $R^2$, and $R^3$ independently are H or a substituent as described herein.

For example, in various embodiments, each of $R^1$, $R^2$, and $R^3$ independently can be H or a substituent which can impart improved desirable properties to the compound as a whole. For example, certain substituents including one or more electron-withdrawing or electron-donating moieties can modulate the electronic properties of the compound, while substituents that include one or more aliphatic chains can improve the solubility of the compound in organic solvents.

Generally, $R^1$ can be selected from H, a $C_{1-40}$ alkyl group, a $C_{2-40}$ alkenyl group, a $C_{2-40}$ alkynyl group, a $C_{1-40}$ haloalkyl group, and an organic group comprising 1-4 cyclic moieties wherein:

a) each of the $C_{1-40}$ alkyl group, the $C_{2-40}$ alkenyl group, the $C_{2-40}$ alkynyl group, and the $C_{1-40}$ haloalkyl group optionally can be substituted with 1-10 substituents independently selected from a halogen, —CN, $NO_2$, OH, —$NH_2$, —NH($C_{1-40}$ alkyl), —N($C_{1-40}$ alkyl)$_2$, —S(O)$_2$OH, —CHO, —C(O)—$C_{1-40}$ alkyl, —C(O)OH, —C(O)—O$C_{1-40}$ alkyl, —C(O)$NH_2$, —C(O)NH—$C_{1-40}$ alkyl, —C(O)N($C_{1-40}$ alkyl)$_2$, —O$C_{1-40}$ alkyl, —$SiH_3$, —$SiH_2$($C_{1-40}$ alkyl), —$SiH_2$($C_{1-40}$ alkyl), —Si($C_{1-40}$ alkyl)$_3$, —Si($C_{1-40}$ alkyl)$_2$(—O—Si($C_{1-40}$ alkyl)$_3$), —Si($C_{1-40}$ alkyl)(-O—Si($C_{1-40}$ alkyl)$_3$)$_2$, —Si(—O—Si($C_{1-40}$ alkyl)$_3$)$_3$, —O—$SiH_3$, —O—SiH($C_{1-40}$ alkyl)$_2$, —O—$SiH_2$($C_{1-40}$ alkyl), —O—Si($C_{1-40}$ alkyl)$_3$, —O—Si($C_{1-40}$ alkyl)$_2$(—O—Si($C_{1-40}$ alkyl)$_3$), and —O—Si($C_{1-40}$ alkyl)(-O—Si($C_{1-40}$ alkyl)$_3$)$_2$;

b) each of the $C_{1-40}$ alkyl group, the $C_{2-40}$ alkenyl group, the $C_{2-40}$ alkynyl group, and the $C_{1-40}$ haloalkyl group can be covalently bonded to the sulfonamide nitrogen atom via an optional linker; and c) the 1-4 cyclic moieties in the organic group can be the same or different, and the 1-4 cyclic moieties can be bonded covalently to each other or the sulfonamide nitrogen atom via an optional linker, and optionally can be substituted with 1-5 substituents independently selected from a halogen, —CN, oxo, $NO_2$, OH, =C(CN)$_2$, —$NH_2$, —NH($C_{1-40}$ alkyl), —N($C_{1-40}$ alkyl)$_2$, —S(O)$_2$OH, —CHO, —C(O)OH, —C(O)—$C_{1-40}$ alkyl, —C(O)—O$C_{1-40}$ alkyl, —C(O)$NH_2$, —C(O)NH—$C_{1-40}$ alkyl, —C(O)N($C_{1-40}$ alkyl)$_2$, —$SiH_3$, —SiH($C_{1-40}$ alkyl)$_2$, —$SiH_2$($C_{1-40}$ alkyl), —Si($C_{1-40}$ alkyl)$_3$, —O—$C_{1-40}$ alkyl, a $C_{1-40}$ alkyl group, a $C_{2-40}$ alkenyl group, a $C_{2-40}$ alkynyl group, and a $C_{1-40}$ haloalkyl group; wherein each of the $C_{1-40}$ alkyl group, the $C_{2-40}$ alkenyl group, the $C_{2-40}$ alkynyl group, and the $C_{1-40}$ haloalkyl group optionally can be substituted with 1-5 substituents independently selected from a halogen, —CN, $NO_2$, OH, —$NH_2$, —NH($C_{1-6}$ alkyl), —N($C_{1-6}$ alkyl)$_2$, —S(O)$_2$OH, —CHO, —C(O)—$C_{1-6}$ alkyl, —C(O)OH, —C(O)—O$C_{1-6}$ alkyl, —C(O)$NH_2$, —C(O)NH—$C_{1-6}$ alkyl, —C(O)N($C_{1-6}$ alkyl)$_2$, —O$C_{1-6}$ alkyl, —$SiH_3$, —SiH($C_{1-40}$ alkyl)$_2$, —$SiH_2$($C_{1-40}$ alkyl), —Si($C_{1-40}$ alkyl)$_3$, —Si($C_{1-40}$ alkyl)$_2$(—O—Si($C_{1-40}$ alkyl)$_3$), —Si($C_{1-40}$ alkyl)(-O—Si($C_{1-40}$ alkyl)$_3$)$_2$, —Si(—O—Si($C_{1-40}$ alkyl)$_3$)$_3$, —O—$SiH_3$, —O—SiH($C_{1-40}$ alkyl)$_2$, —O—$SiH_2$($C_{1-40}$ alkyl), —O—Si($C_{1-40}$ alkyl)$_3$, —O—Si($C_{1-40}$ alkyl)$_2$(—O—Si($C_{1-40}$ alkyl)$_3$), and —O—Si($C_{1-40}$ alkyl)(-O—Si($C_{1-40}$ alkyl)$_3$)$_2$; and $R^2$ and $R^3$ independently can be selected from H, F, Cl, —CN, a $C_{1-40}$ alkyl group, a $C_{2-40}$ alkenyl group, a $C_{2-40}$ alkynyl group, a $C_{1-40}$ haloalkyl group, a $C_{1-40}$ alkoxy group, and a $C_{1-40}$ thioalkyl group, where the $C_{1-40}$ alkyl group, the $C_{2-40}$ alkenyl group, the $C_{2-40}$ alkynyl group, the $C_{1-40}$ haloalkyl group, the $C_{1-40}$ alkoxy group, and the $C_{1-40}$ thioalkyl group can be optionally substituted as described herein.

To illustrate, in certain embodiments, $R^1$ can be selected from H, a $C_{1-40}$ alkyl group, a $C_{2-40}$ alkenyl group, a $C_{2-40}$ alkynyl group, and a $C_{1-40}$ haloalkyl group, each of which optionally can be substituted with 1-10 substituents independently selected from a halogen, —CN, $NO_2$, OH, —$NH_2$, —NH($C_{1-40}$ alkyl), —N($C_{1-40}$ alkyl)$_2$, —S(O)$_2$OH, —CHO, —C(O)—$C_{1-40}$ alkyl, —C(O)OH, —C(O)—O$C_{1-40}$ alkyl, —C(O)$NH_2$, —C(O)NH—$C_{1-40}$ alkyl, —C(O)N($C_{1-40}$ alkyl)$_2$, —O$C_{1-40}$ alkyl, —$SiH_3$, —SiH($C_{1-40}$ alkyl)$_2$, —$SiH_2$($C_{1-40}$ alkyl), —Si($C_{1-40}$ alkyl)$_3$, —Si($C_{1-40}$ alkyl)$_2$(—O—Si($C_{1-40}$ alkyl)$_3$), —Si($C_{1-40}$ alkyl)(-O—Si($C_{1-40}$ alkyl)$_3$)$_2$, —Si(—O—Si($C_{1-40}$ alkyl)$_3$)$_3$, —O—$SiH_3$, —O—SiH($C_{1-40}$ alkyl)$_2$, —O—$SiH_2$($C_{1-40}$ alkyl), —O—Si($C_{1-40}$ alkyl)$_3$, —O—Si($C_{1-40}$ alkyl)$_2$(—O—Si($C_{1-40}$ alkyl)$_3$), and —O—Si($C_{1-40}$ alkyl)(-O—Si($C_{1-40}$ alkyl)$_3$)$_2$. In preferred embodiments, $R^1$ can be a linear or branched aliphatic group having at least 3 carbon atoms, more preferably, a linear or branched aliphatic group having at least 6 carbon atoms, and most preferably, a linear or branched aliphatic group having at least 8 carbon atoms.

To illustrate further, in particular embodiments, $R^1$ can be a linear $C_{6-40}$ alkyl, alkenyl, alkynyl or halolalkyl group optionally substituted with 1-10 substituents independently selected from a halogen, —CN, $NO_2$, OH, —$NH_2$, —NH($C_{1-40}$ alkyl), —N($C_{1-40}$ alkyl)$_2$, —S(O)$_2$OH, —CHO, —C(O)—$C_{1-40}$ alkyl, —C(O)OH, —C(O)—O$C_{1-40}$ alkyl, —C(O)$NH_2$, —C(O)NH—$C_{1-40}$ alkyl, —C(O)N($C_{1-40}$ alkyl)$_2$, —O$C_{1-40}$ alkyl, —$SiH_3$, —SiH($C_{1-40}$ alkyl)$_2$, —$SiH_2$($C_{1-40}$ alkyl), —Si($C_{1-40}$ alkyl)$_3$, —Si($C_{1-40}$ alkyl)$_2$(—O—Si($C_{1-40}$ alkyl)$_3$), —Si($C_{1-40}$ alkyl)(-O—Si($C_{1-40}$ alkyl)$_3$)$_2$, —Si(—O—Si($C_{1-40}$ alkyl)$_3$)$_3$, —O—$SiH_3$, —O—SiH($C_{1-40}$ alkyl)$_2$, —O—$SiH_2$($C_{1-40}$ alkyl), —O—Si($C_{1-40}$ alkyl)$_3$, —O—Si($C_{1-40}$ alkyl)$_2$(—O—Si($C_{1-40}$ alkyl)$_3$), and —O—Si($C_{1-40}$ alkyl)(-O—Si($C_{1-40}$ alkyl)$_3$)$_2$. In certain embodiments, $R^1$ can be a branched $C_{6-40}$ alkyl, alkenyl, alkynl or halolalkyl group having the formula —CHR'$_2$, where each R' independently can be a $C_{1-20}$ alkyl group, a $C_{1-20}$ haloalkyl group, a $C_{2-20}$ alkenyl group, or a $C_{2-20}$ alkynyl group, each of which optionally can be substituted with 1-10 substituents independently selected from a halogen, —CN, $NO_2$, OH, —$NH_2$, —NH($C_{1-40}$ alkyl), —N($C_{1-40}$ alkyl)$_2$, —S(O)$_2$OH, —CHO, —C(O)—$C_{1-40}$ alkyl, —C(O)OH, —C(O)—O$C_{1-40}$ alkyl, —C(O)$NH_2$, —C(O)NH—$C_{1-40}$ alkyl, —C(O)N($C_{1-40}$ alkyl)$_2$, —O$C_{1-40}$ alkyl, —$SiH_3$, —SiH($C_{1-40}$ alkyl)$_2$, —$SiH_2$($C_{1-40}$ alkyl), —Si($C_{1-40}$ alkyl)$_3$, —Si($C_{1-40}$ alkyl)$_2$(—O—Si($C_{1-40}$ alkyl)$_3$), —Si($C_{1-40}$ alkyl)(-O—Si($C_{1-40}$ alkyl)$_3$)$_2$, —Si(—O—Si($C_{1-40}$ alkyl)$_3$)$_3$, —O—$SiH_3$, —O—SiH($C_{1-40}$ alkyl)$_2$, —O—$SiH_2$($C_{1-40}$ alkyl), —O—Si($C_{1-40}$ alkyl)$_3$, —O—Si($C_{1-40}$ alkyl)$_2$(—O—Si($C_{1-40}$ alkyl)$_3$), and —O—Si($C_{1-40}$ alkyl)(-O—Si($C_{1-40}$ alkyl)$_3$)$_2$. In certain embodiments, $R^1$ can be a branched $C_{6-40}$ alkyl, alkenyl, alkynl or halolalkyl group having the formula —$CH_2$—CHR'$_2$, where R' is as defined herein.

In other embodiments, $R^1$ can be an organic group comprising one or more cyclic moieties. For example, $R^1$, at each occurrence, independently can be selected from -L'-$Cy^1$, -L'-$Cy^1$-L'-$Cy^2$, -L'-$Cy^1$-L'-$Cy^2$-$Cy^2$, -L'-$Cy^1$-$Cy^1$, -L'-$Cy^1$-$Cy^1$-L'-$Cy^2$, -L'-$Cy^1$-$Cy^1$-L'-$Cy^2$-$Cy^2$, -L'-$Cy^1$-L'-R', -L'-$Cy^1$-L'-$Cy^2$-L'-R', -L'-$Cy^1$-L'-$Cy^2$-$Cy^2$-L'-R', -L'-$Cy^1$-$Cy^1$-L'-R', and -L'-$Cy^1$-$Cy^1$-L'-$Cy^2$-L'-R'; wherein:

$Cy^1$ and $Cy^2$ independently are selected from a $C_{6-14}$ aryl group, a 5-14 membered heteroaryl group, a $C_{3-14}$ cycloalkyl group, and a 3-14 membered cycloheteroalkyl group, each of which optionally can be substituted with 1-5 substituents independently selected from a halogen, —CN, oxo, =C(CN)$_2$, a $C_{1-6}$ alkyl group, a $C_{1-6}$ alkoxy group, and a $C_{1-6}$ haloalkyl group;

L', at each occurrence, independently is a covalent bond or a divalent linker selected from —O—, —S—, —S(O)$_2$—, —C(O)—, —$SiH_2$—, —$SiHCH_3$—, —Si($CH_3$)$_2$—, a divalent $C_{1-40}$ alkyl group, a divalent $C_{2-40}$ alkenyl group, and a divalent $C_{1-40}$ haloalkyl group; and R' is as defined herein.

In some embodiments, the present compound is a polymer having one or more repeating units $M_1$, where each $M_1$ includes at least one optionally substituted bithiophene sulfonamide moiety represented by formula (I), and where the polymer has a degree of polymerization (n) ranging from at least 3.

Other than bithiophene sulfonamide moieties, repeating units $M_1$ optionally can include one or more spacers (Sp) which can be either non-cyclic (Z) or cyclic, particularly monocyclic (Ar) or polycyclic (pi-2), which together with the bithiophene sulfonamide moieties provide a pi-extended conjugated group. For example, $M_1$ can have a formula selected from:

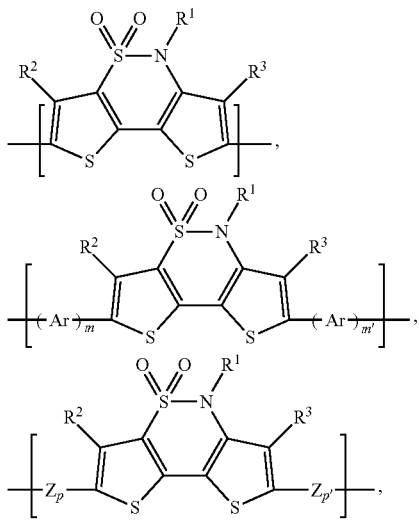

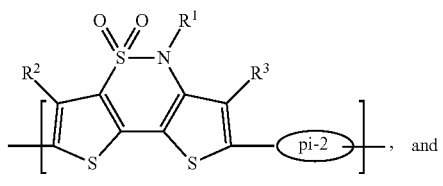

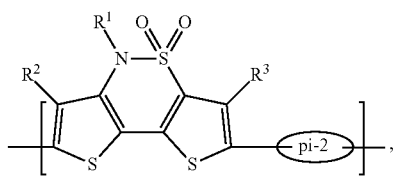

wherein:

m and m' independently are 0, 1, 2, 3, 4, 5 or 6, provided that at least one of m and m' is not 0;

p and p' independently are 0 and 1, provided that at least one of p and p' is 1; and $R^1$, $R^2$, $R^3$, Ar, Z, and pi-2 are as defined herein.

In certain embodiments, the repeating unit $M_1$ can include more than one bithiophene sulfonamide moieties. For example, $M_1$ can have a formula selected from:

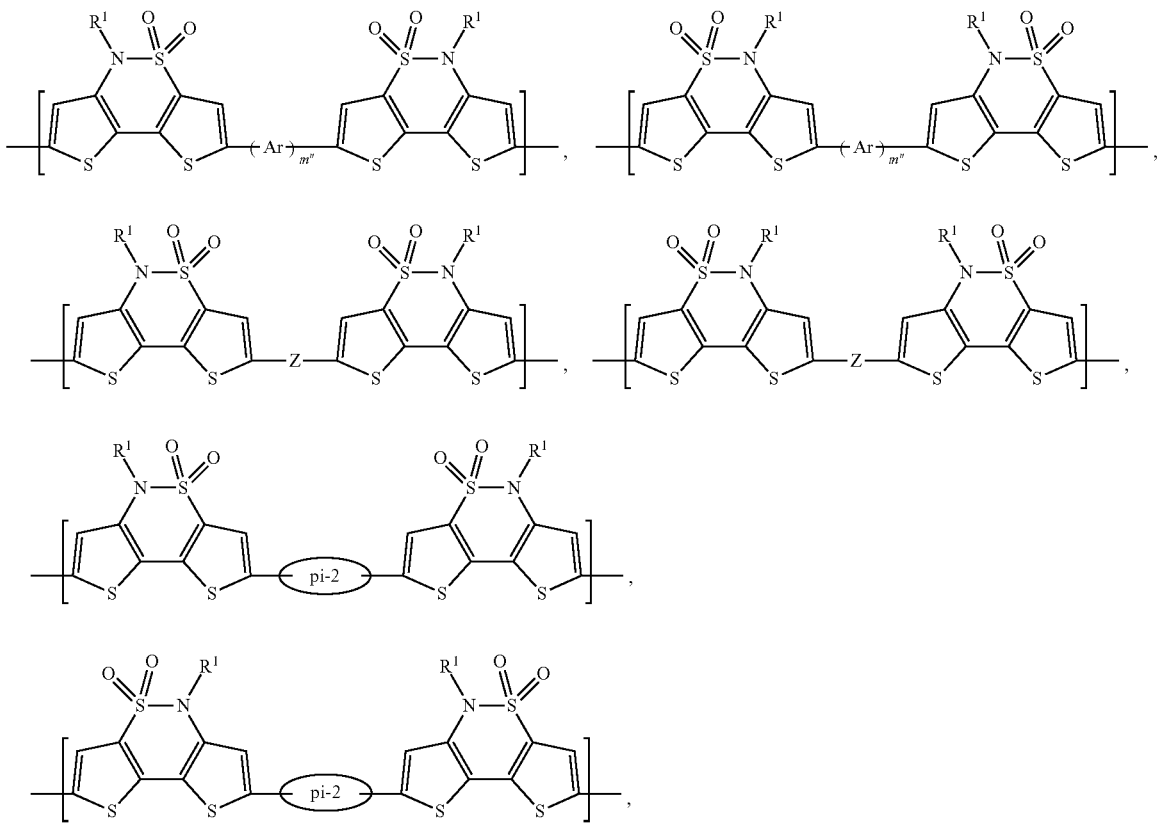

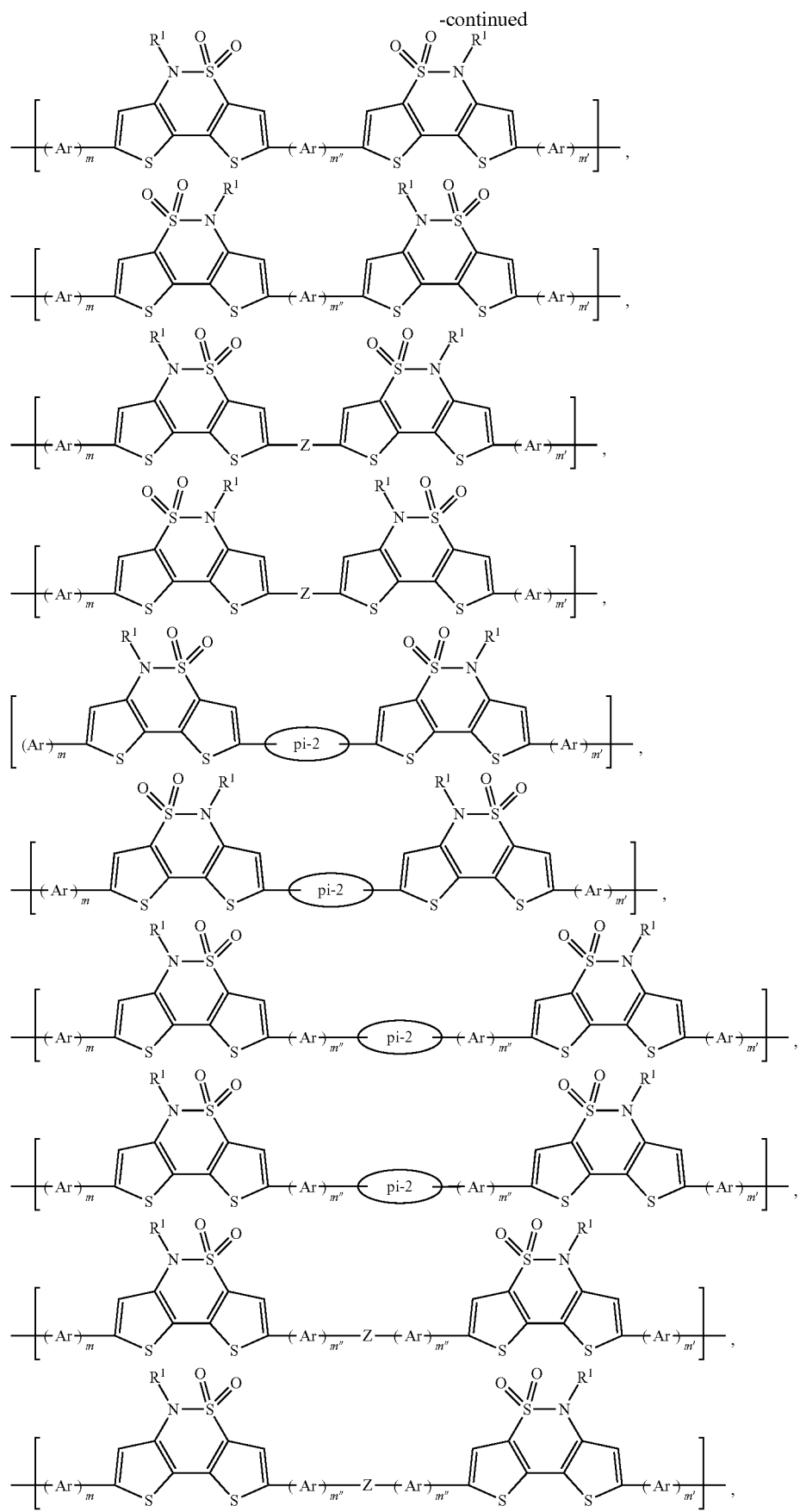

-continued

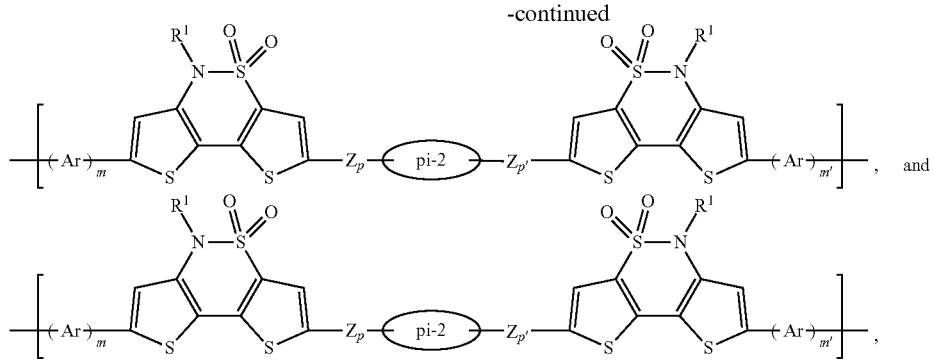

wherein:
m and m' independently are 0, 1, 2, 3, 4, 5 or 6, provided that at least one of m and m' is not 0;
m" is 1, 2, 3, 4, 5 or 6;
p and p' independently are 0 and 1, provided that at least one of p and p' is 1; and
$R^1$, Ar, Z, and pi-2 are as defined herein. One or both of the bithiophene sulfonamide moieties in any of the above representative repeating units $M_1$ also can bear $R^2$ and/or $R^3$ groups that are selected from the substituents described herein.

In various embodiments, the noncyclic spacer Z, can be a conjugated noncyclic linker comprising one or more double or triple bonds. For example, Z can be a divalent ethenyl group (i.e., having one double bond), a divalent ethynyl group (i.e., having one tripe bond), a $C_{4-40}$ alkenyl or alkynyl group that includes two or more conjugated double or triple bonds, or some other linear or branched conjugated systems that can include heteroatoms such as Si, N, P, and the like. In certain embodiments, Z can be selected from:

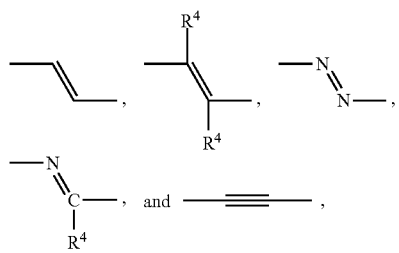

wherein each $R^4$ independently is selected from F, Cl, CN, R, OR, SR, C(O)R, OC(O)R, and C(O)OR, where R is selected from a $C_{1-40}$ alkyl group, a $C_{1-40}$ haloalkyl group, a $C_{2-40}$ alkenyl group, and a $C_{2-40}$ alkynyl group. In particular embodiments, Z can be selected from:

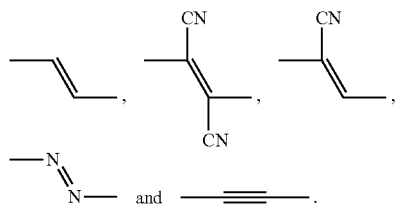

The monocyclic spacer Ar, at each occurrence, independently, can be an optionally substituted monocyclic conjugated group, more specifically, an optionally substituted 5- or 6-membered (hetero)aryl group. For example, Ar can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which optionally can be substituted with 1-4 $R^5$ groups independently selected from a halogen, CN, a $C_{1-40}$ alkyl group, a $C_{1-40}$ haloalkyl group, a $C_{1-40}$ alkoxy group, and a $C_{1-40}$ alkylthio group.

By way of example, each Ar in $(Ar)_m$, $(Ar)_{m'}$, and/or $(Ar)_{m''}$ that is present (i.e., when m, m', and/or m" is 1, 2, 3, 4, 5 or 6) can be represented by:

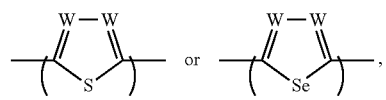

where each W independently can be selected from N, CH, and $CR^4$, wherein $R^4$ can be selected from F, Cl, —CN, R, OR, SR, C(O)R, OC(O)R, and C(O)OR, and where R is selected from a $C_{1-40}$ alkyl group, a $C_{1-40}$ haloalkyl group, a $C_{2-40}$ alkenyl group, and a $C_{2-40}$ alkynyl group. To illustrate further, $(Ar)_m$, $(Ar)_{m'}$, or $(Ar)_{m''}$ when present can be selected from:

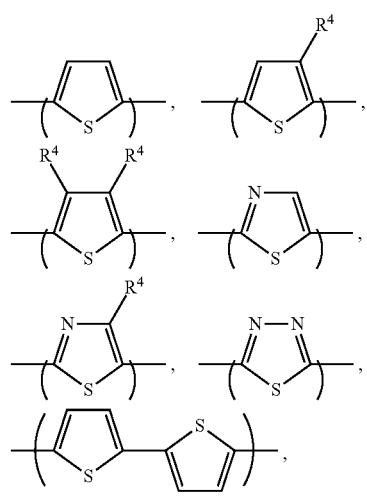

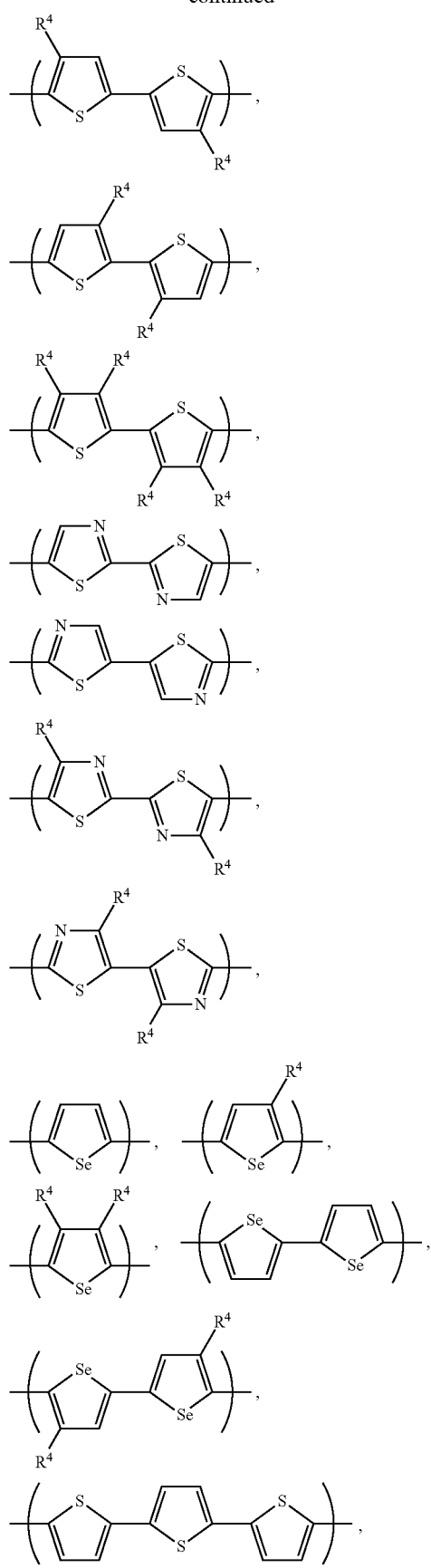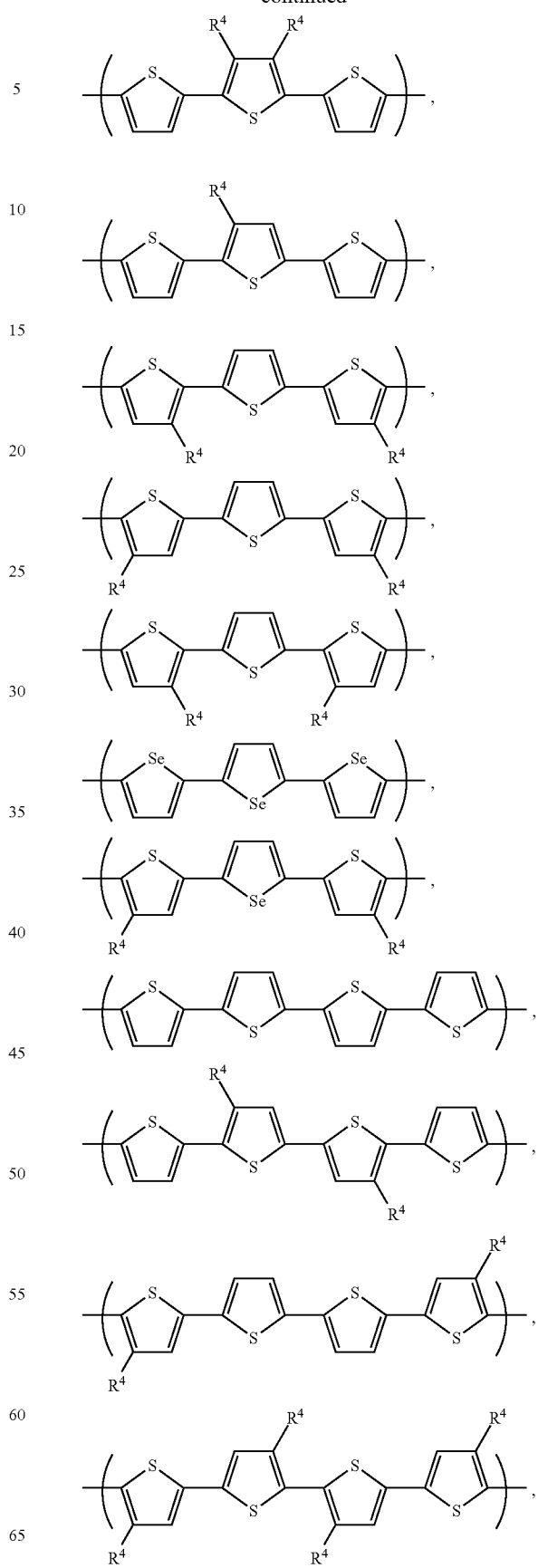

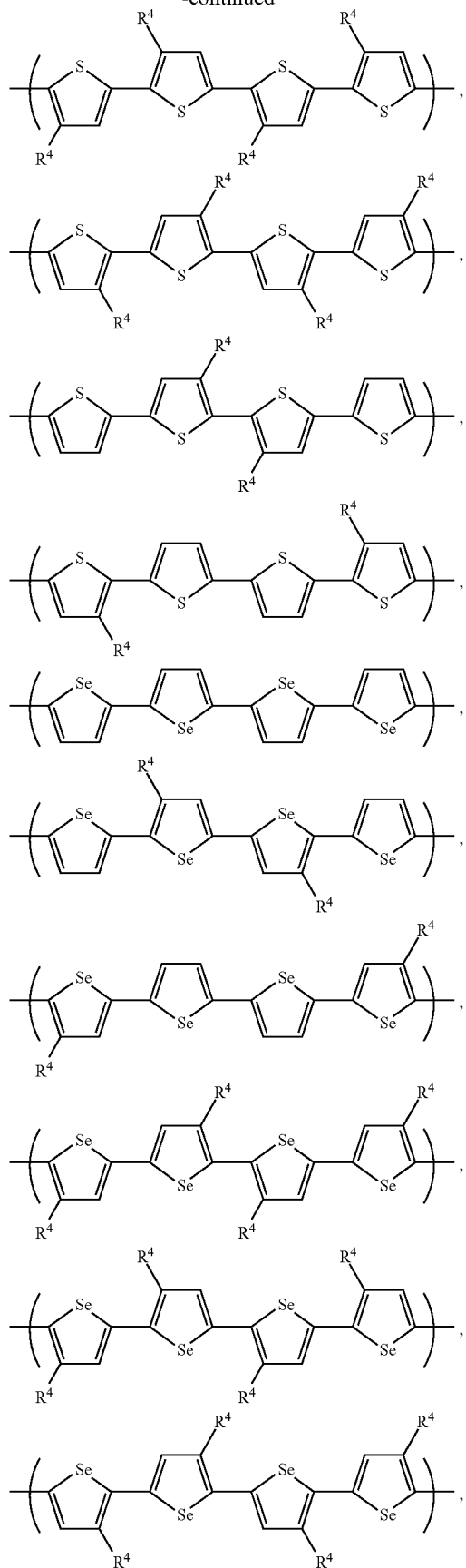

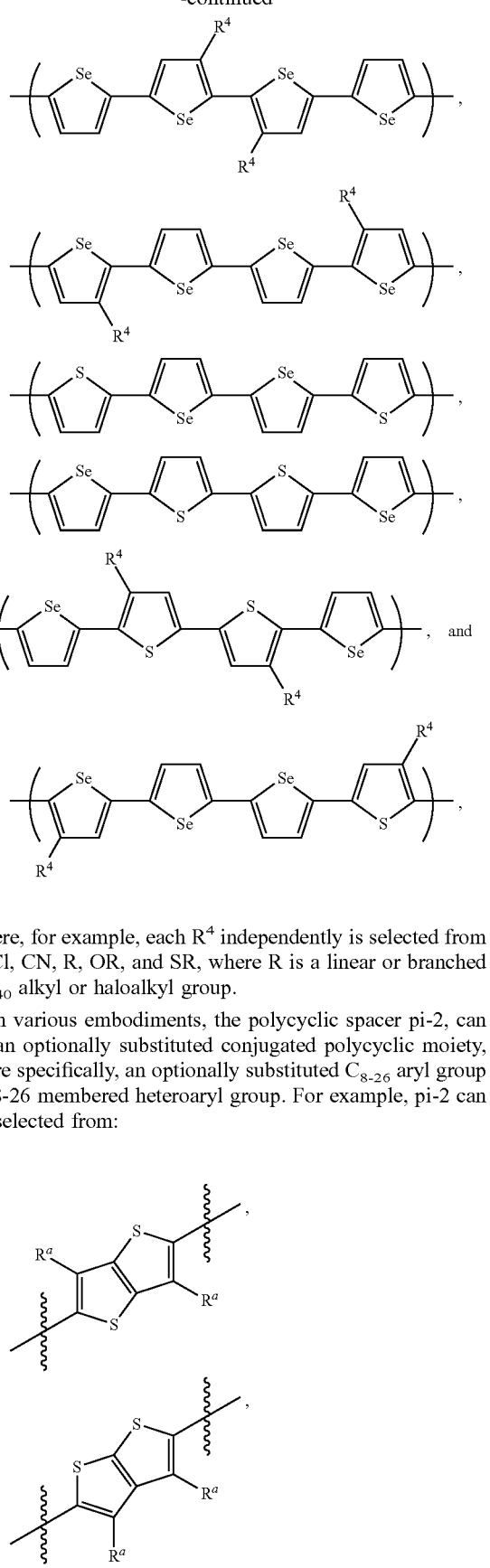

where, for example, each $R^4$ independently is selected from F, Cl, CN, R, OR, and SR, where R is a linear or branched $C_{1-40}$ alkyl or haloalkyl group.

In various embodiments, the polycyclic spacer pi-2, can be an optionally substituted conjugated polycyclic moiety, more specifically, an optionally substituted $C_{8-26}$ aryl group or 8-26 membered heteroaryl group. For example, pi-2 can be selected from:

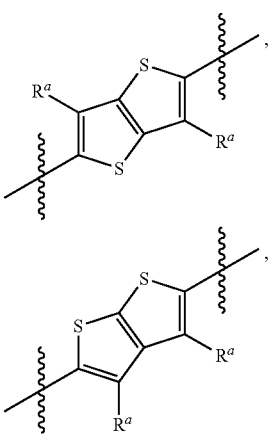

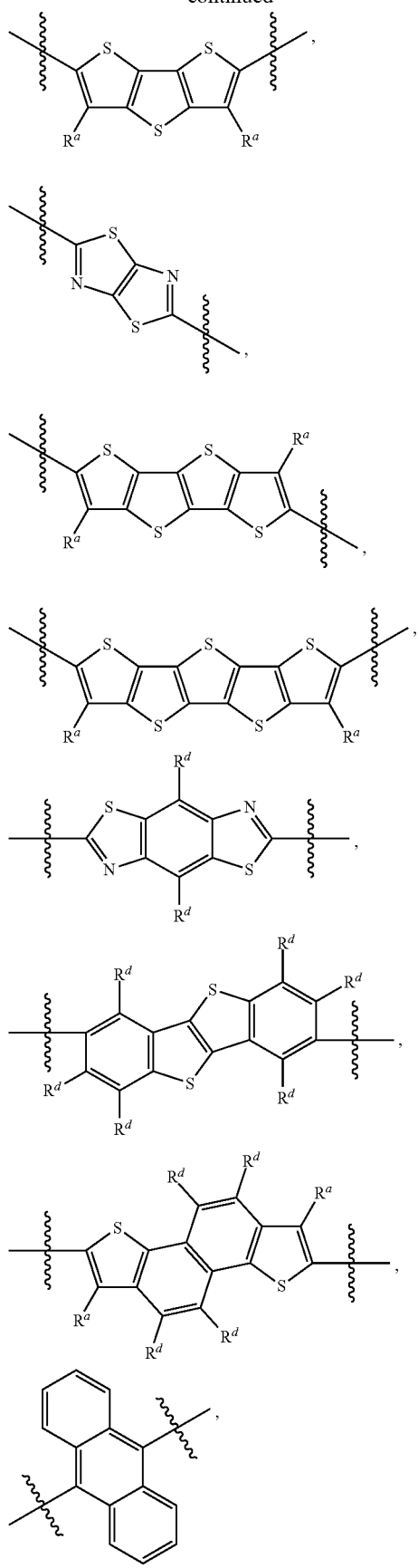
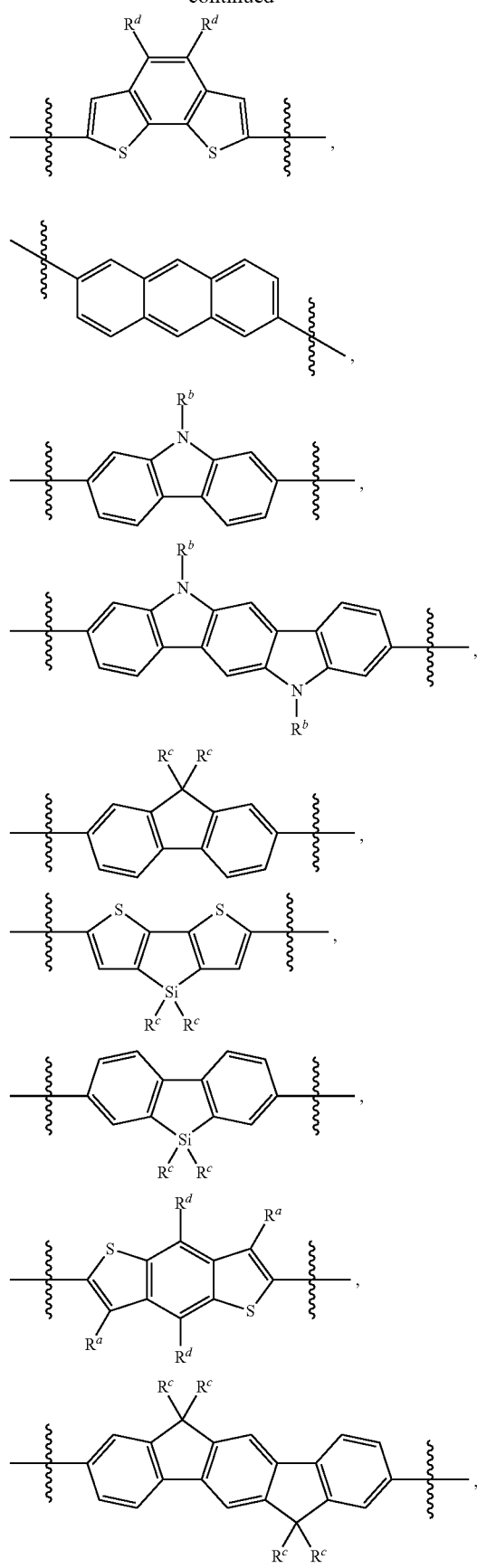

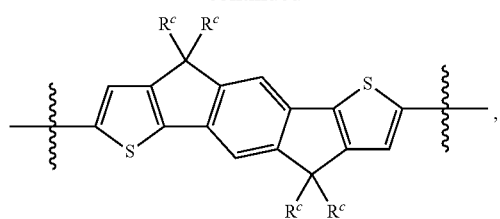
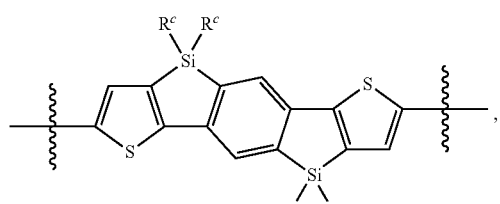
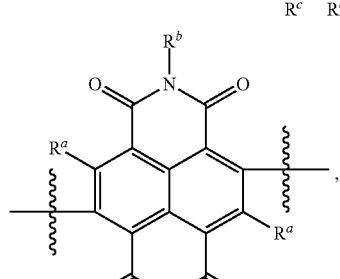
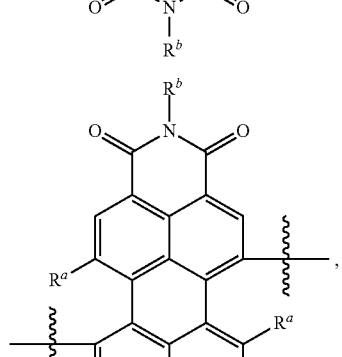
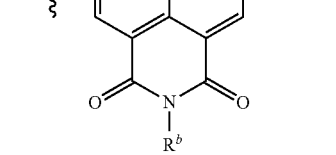
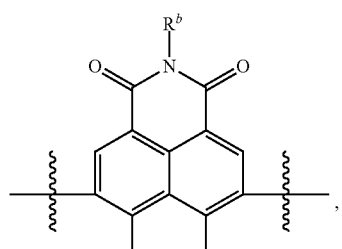
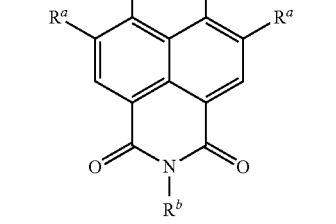
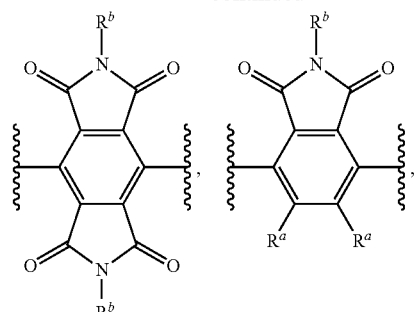
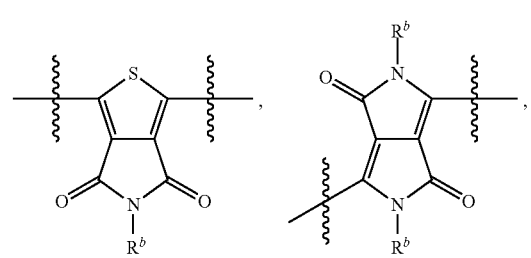
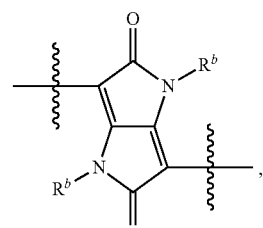
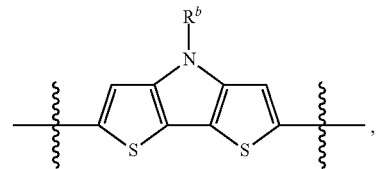
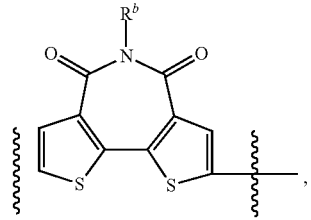
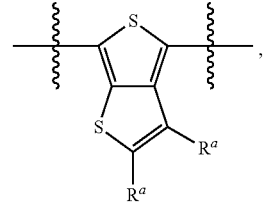
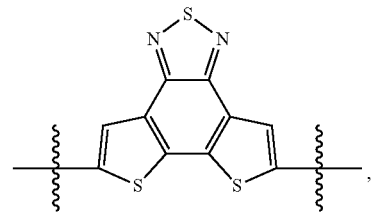

-continued
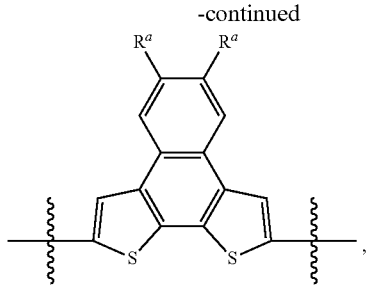
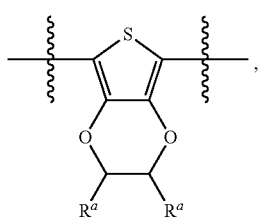
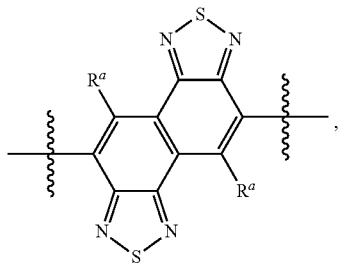
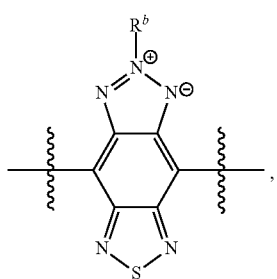
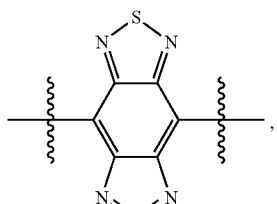
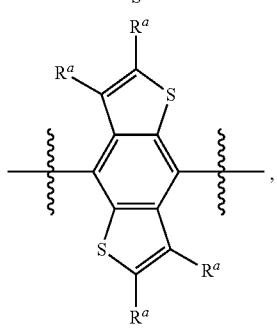
-continued
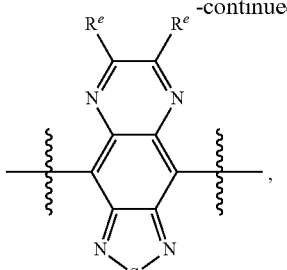
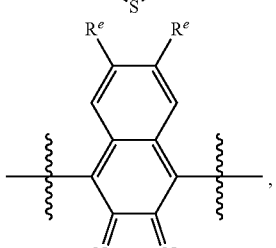
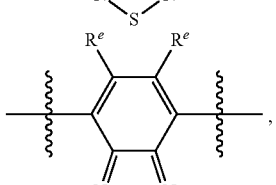
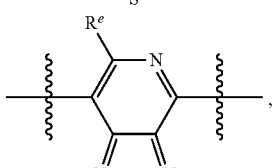
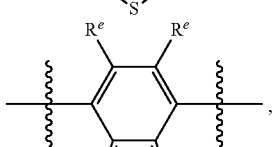
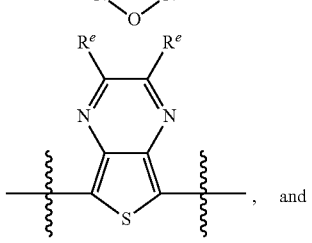, and
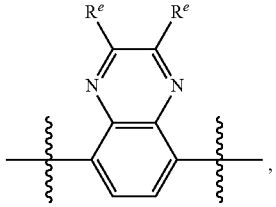
wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-R$^f$;
$R^e$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

In preferred embodiments, the present polymer can include a repeating unit $M_1$ having a formula selected from the group consisting of:

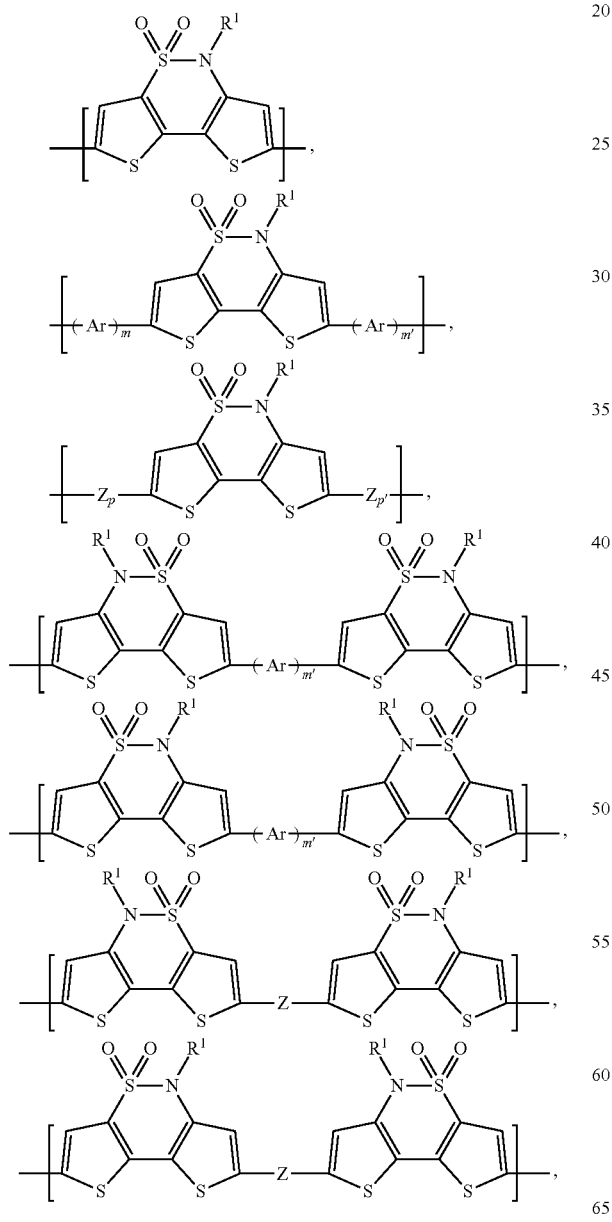

where Ar, $R^1$, Z, m, m', m", p and p' are as defined herein.

Exemplary embodiments of $M_1$ include:

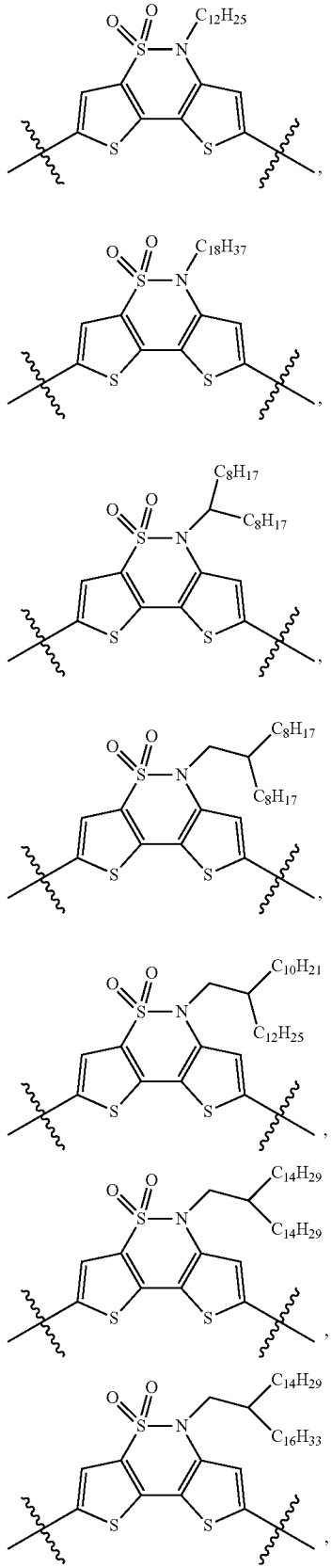

-continued

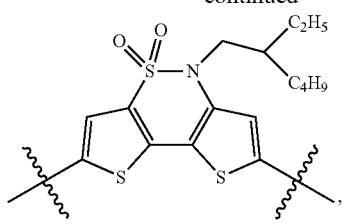

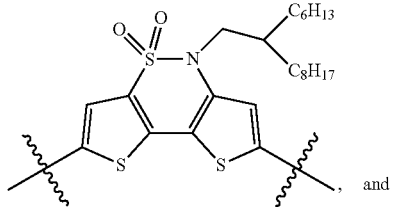, and

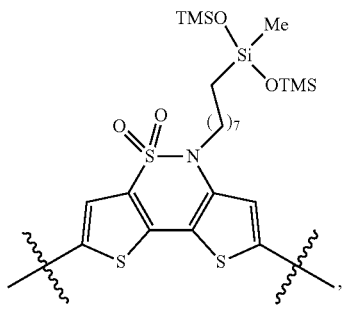

where OTMS is —OSi(CH$_3$)$_3$, and Me is CH$_3$.

In certain embodiments, the present polymer can be a homopolymer including only identical repeating units M$_1$. In other embodiments, the polymer can be a copolymer including two or more different repeating units M$_1$. In yet other embodiments, the polymer can be a copolymer including at least one repeating unit M$_1$ and at least one other repeating unit M$_2$ that does not include any bithiophene sulfonamide moiety. Such M$_2$ units can include one or more non-cyclic (Z), monocyclic (Ar), and/or polycyclic (pi-2) conjugated linkers, which together provide a pi-extended conjugated group. For example, M$_2$ can be selected from:

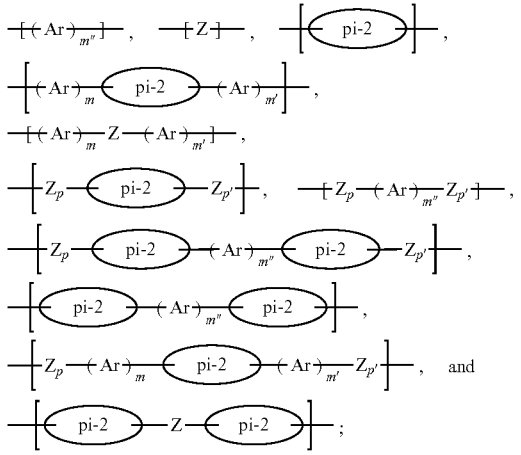

wherein pi-2, Ar, Z, m, m', m", p, and p' are as defined herein.

To illustrate, in certain embodiments, M$_2$ can have the formula:

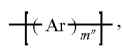, where Ar and m" are as defined herein. For example, M$_2$ can be selected from the group consisting of:

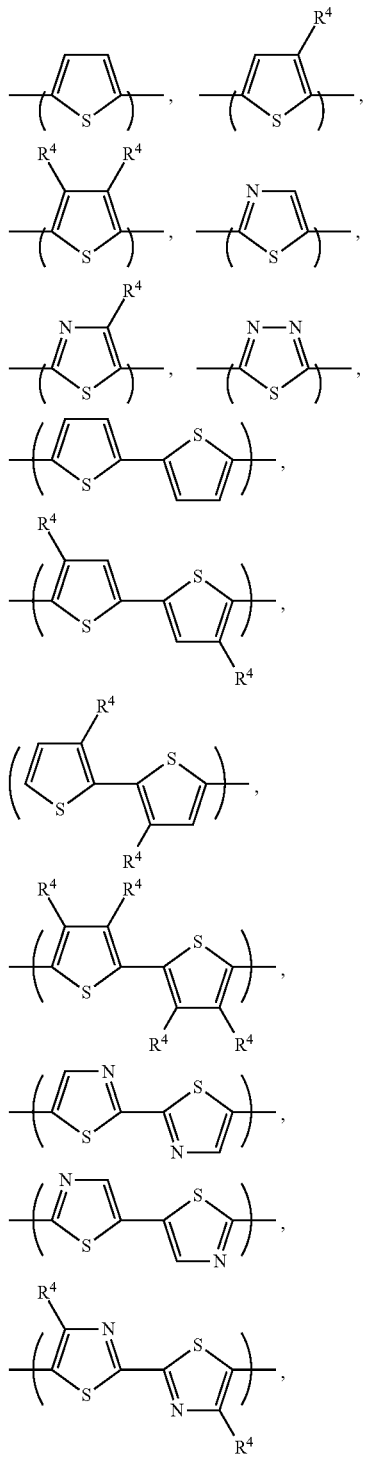

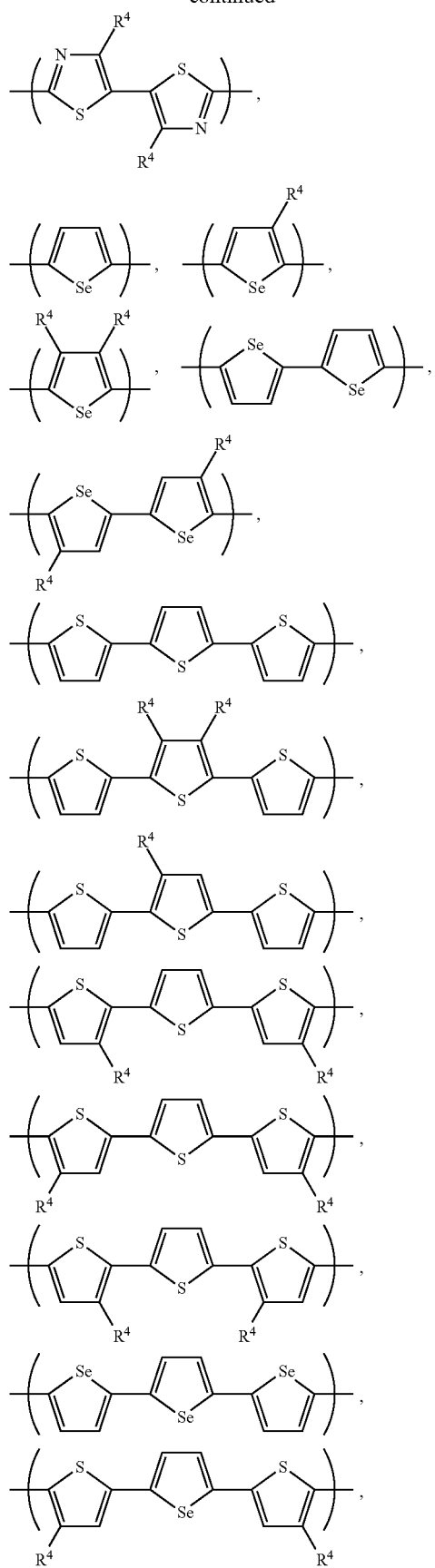
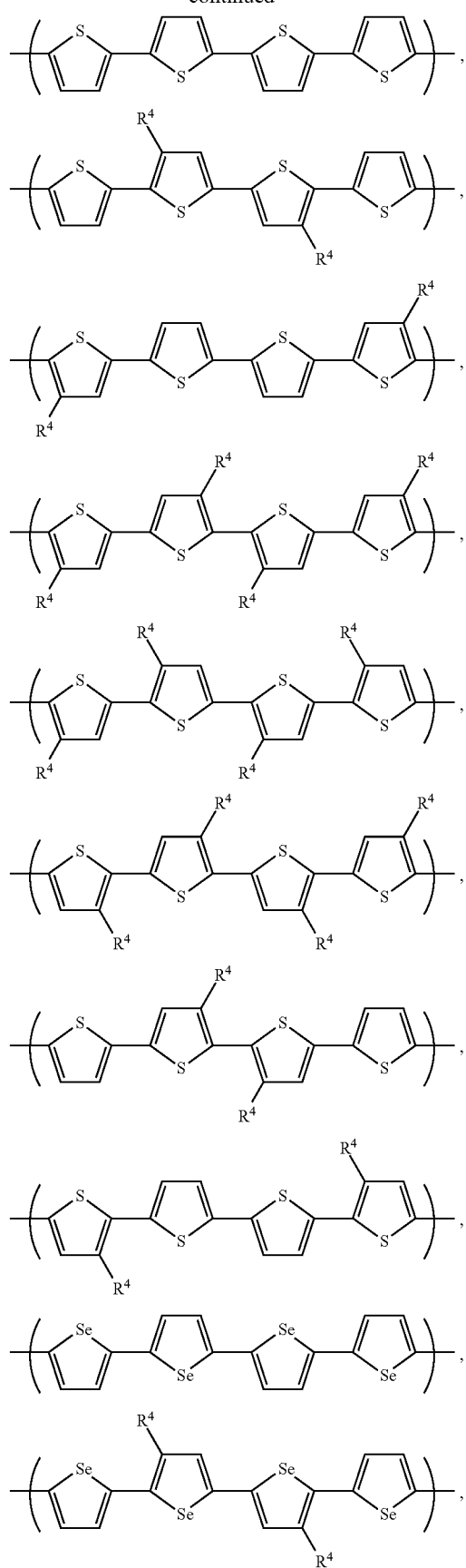

-continued
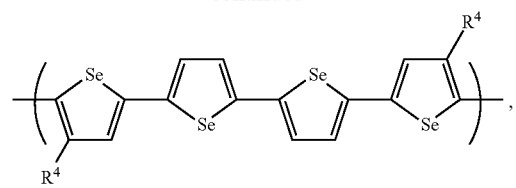
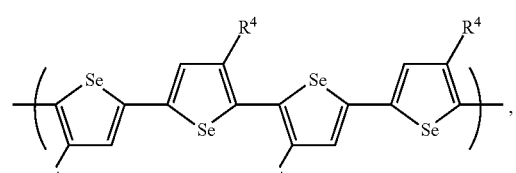
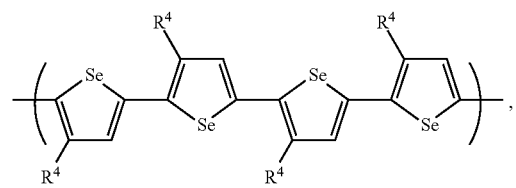
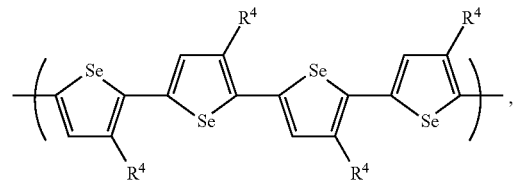
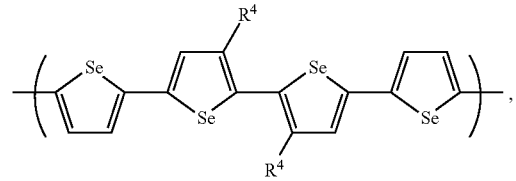
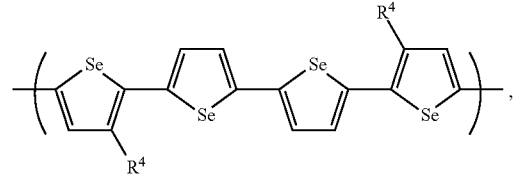
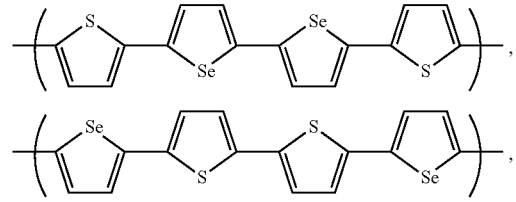
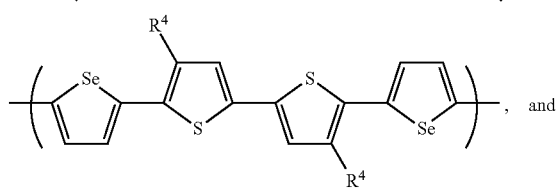, and
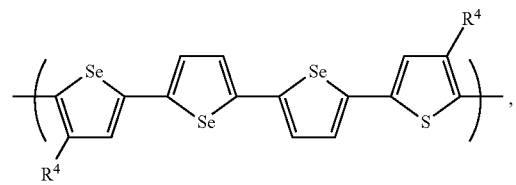
where $R^4$ is as defined herein. For example, each $R^4$ independently can be selected from F, Cl, CN, R, OR, and SR, where R is a linear or branched $C_{1-40}$ alkyl or haloalkyl group.
In other embodiments, $M_2$ can have the formula:
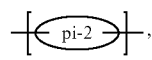
where pi-2 can be selected from:
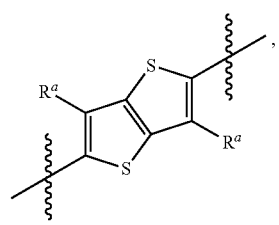
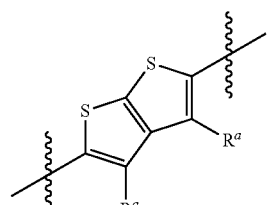
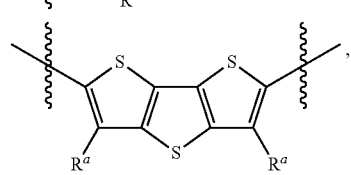
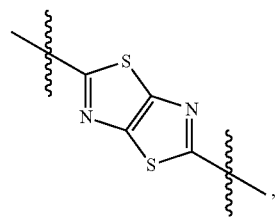
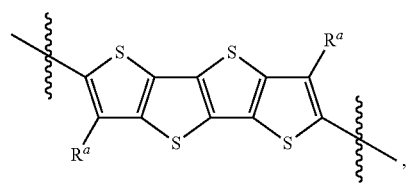
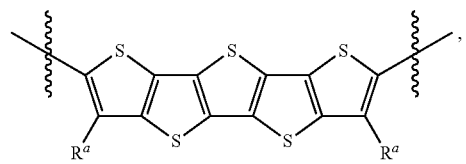
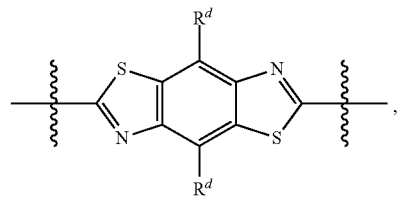

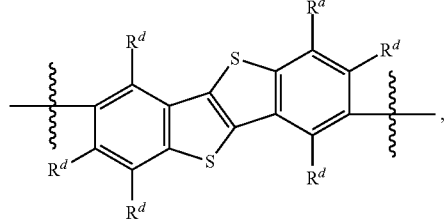
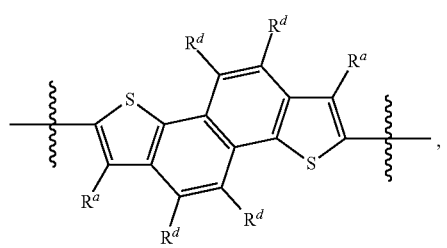
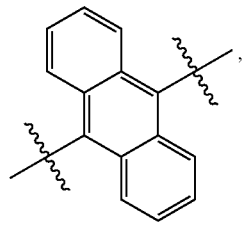
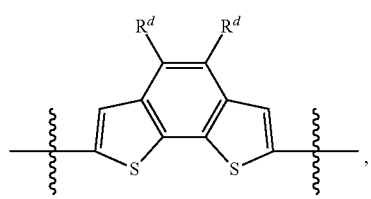
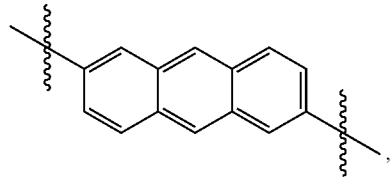
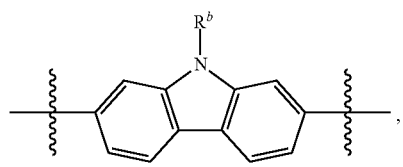
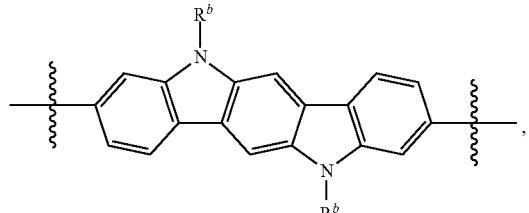
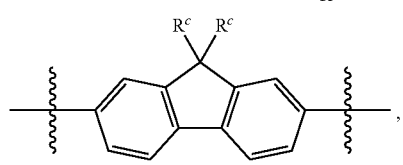
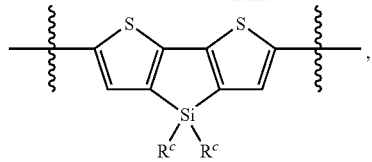
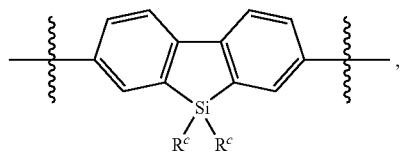
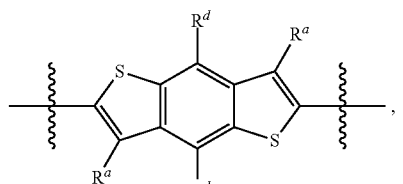
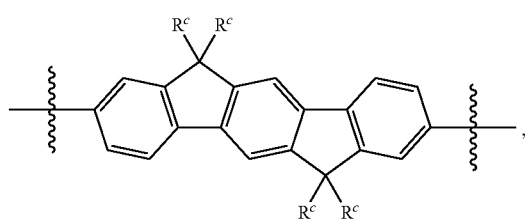
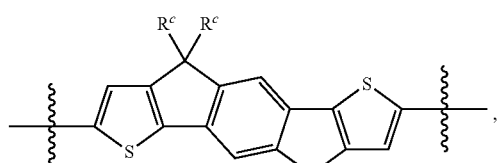
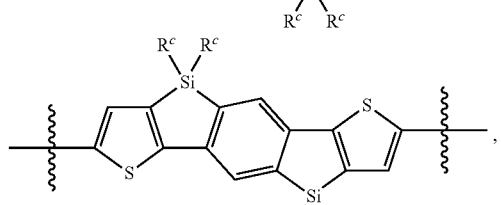
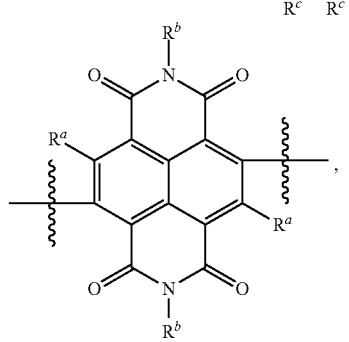

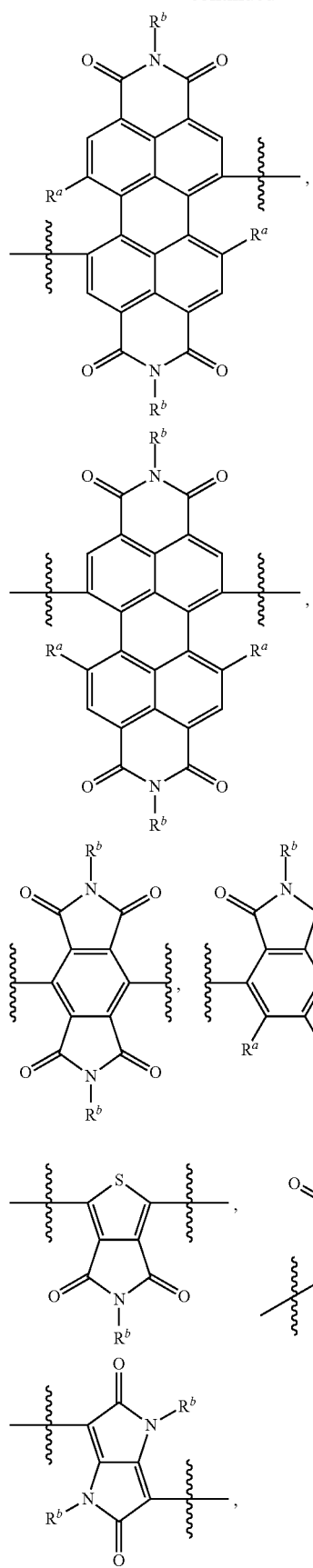
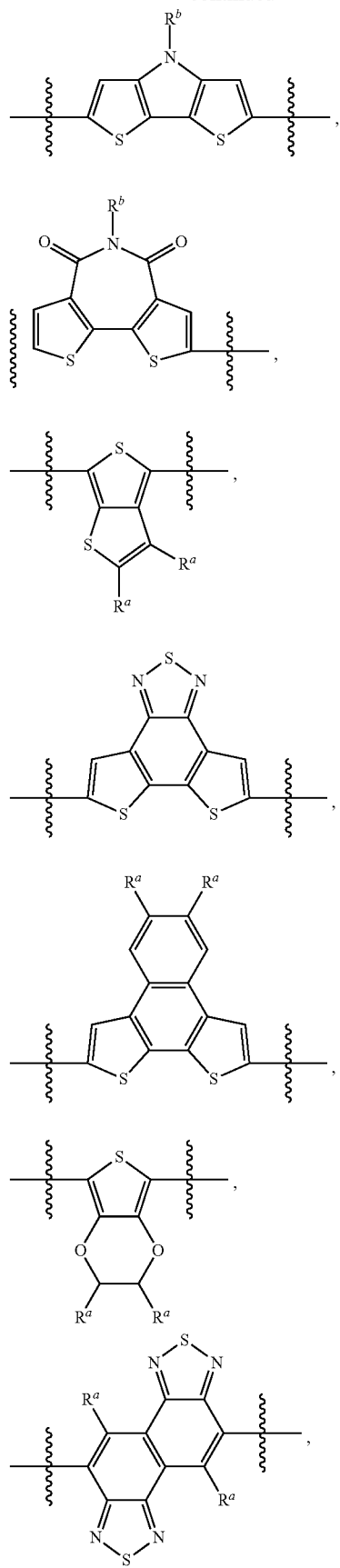

-continued

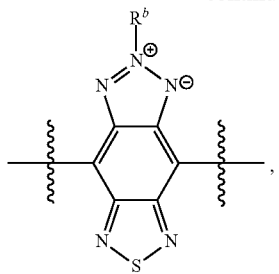,

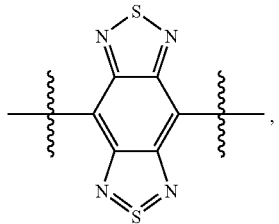,

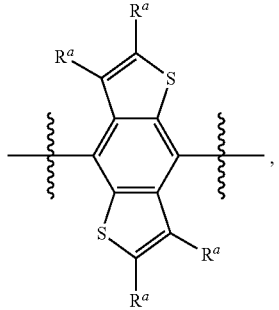,

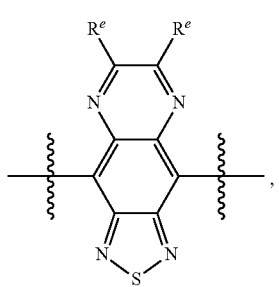,

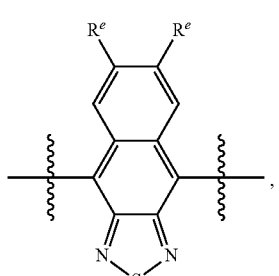,

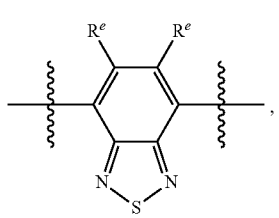,

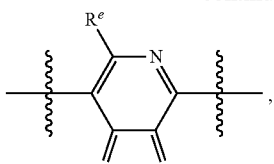,

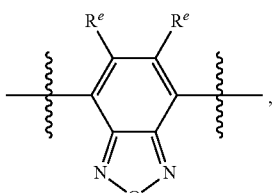,

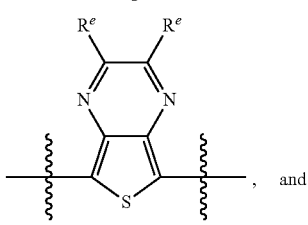, and

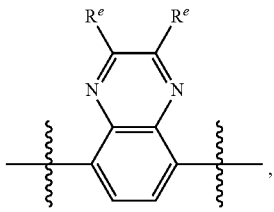, wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

In yet other embodiments, $M_2$ can have the formula:

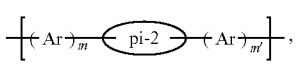, wherein Ar, pi-2, m and m' are as defined herein. Preferably, $(Ar)_m$ and $(Ar)_{m'}$ are selected from:

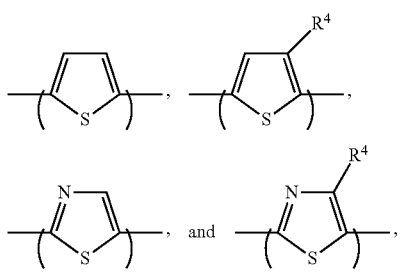
where R⁴ is as defined herein, and pi-2 is selected from:
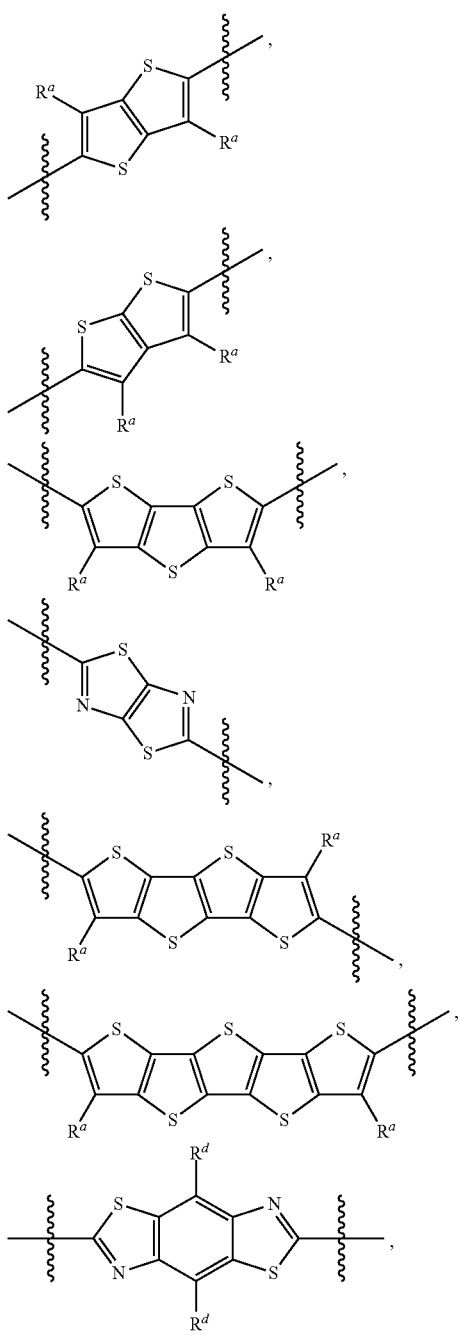
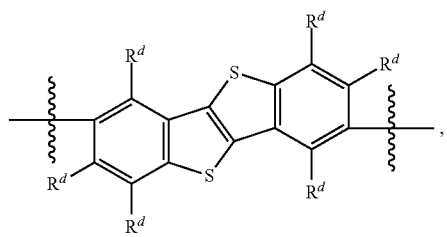
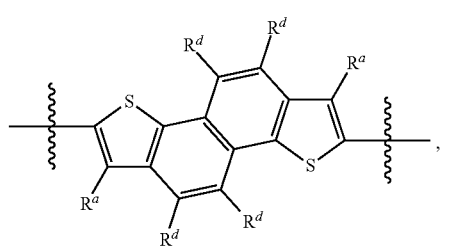
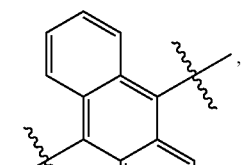
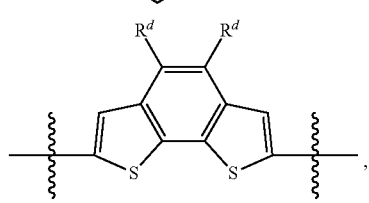
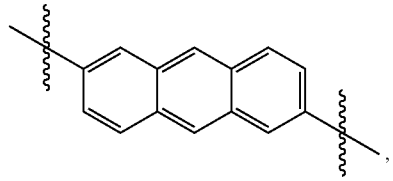
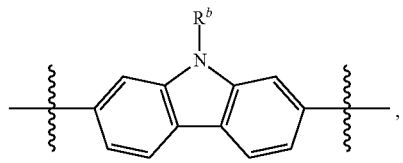
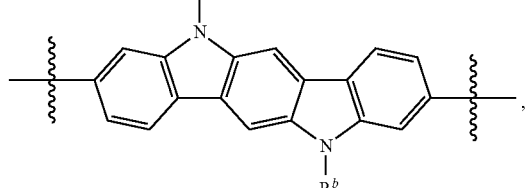
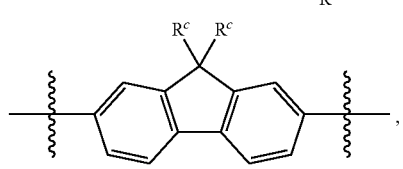

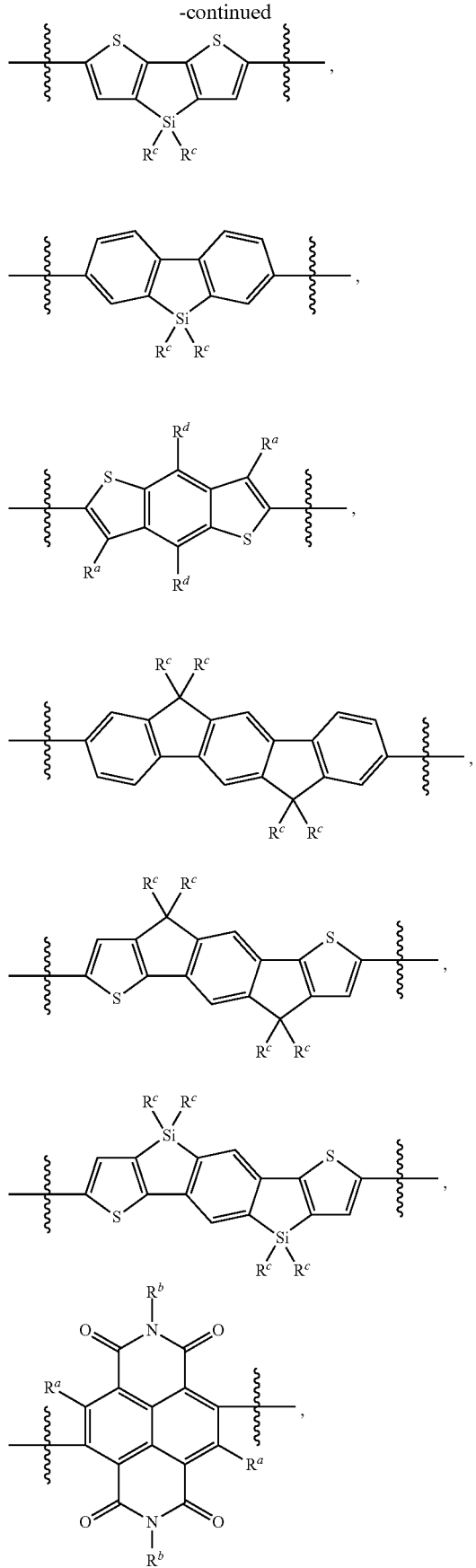
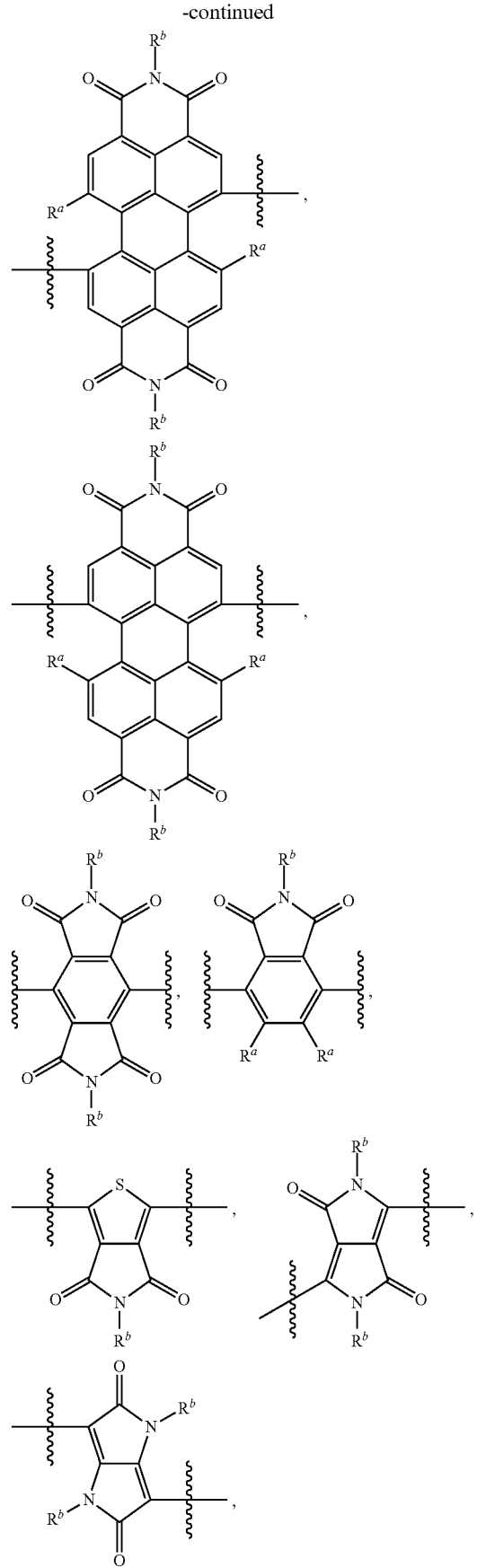

-continued
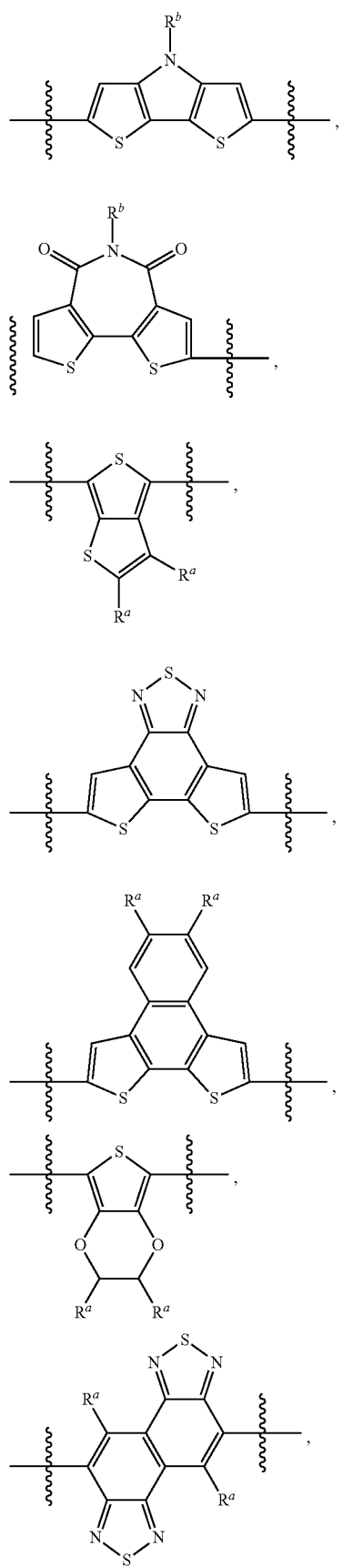
-continued
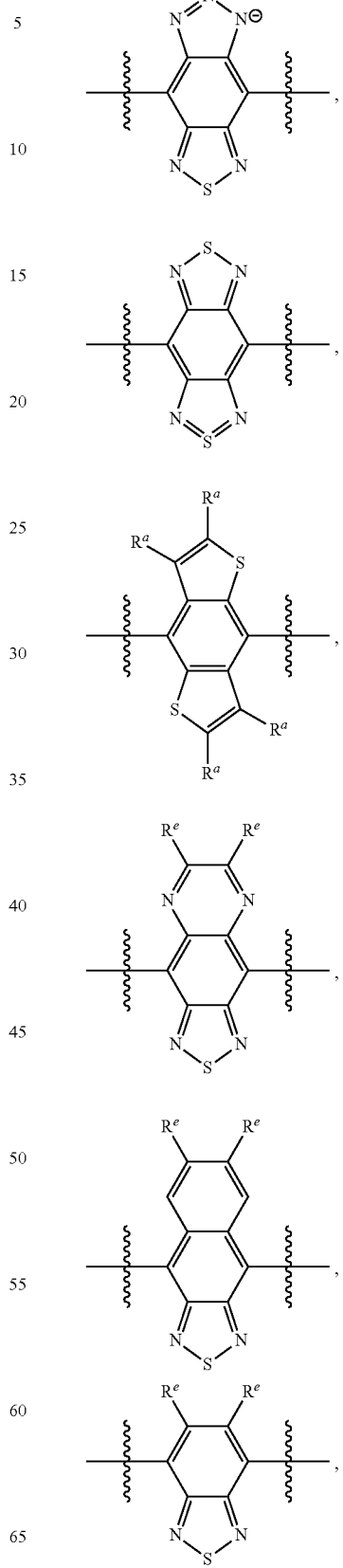

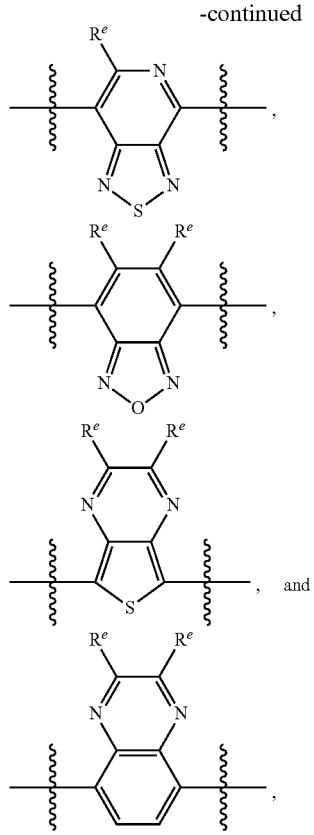

wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

In other embodiments, $M_2$ can have a formula selected from:

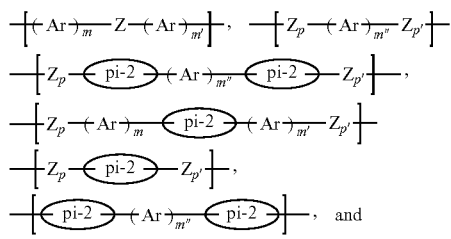

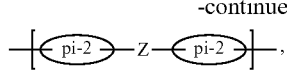

wherein m, m' and m" independently are 1, 2, 3 or 4; and Ar, pi-2 and Z are as defined herein. In such embodiments, $M_2$ can be selected from the group consisting of:

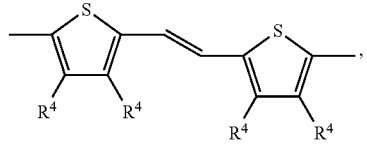

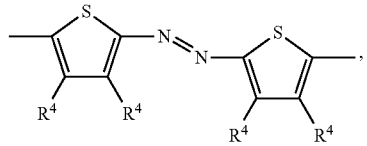

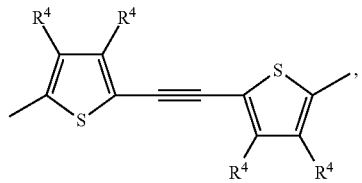

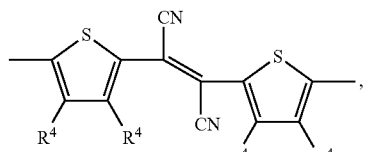

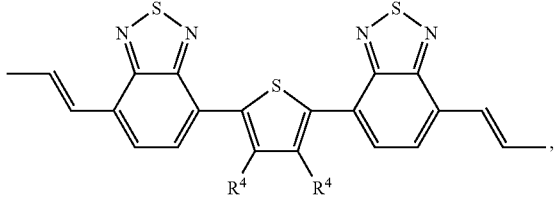

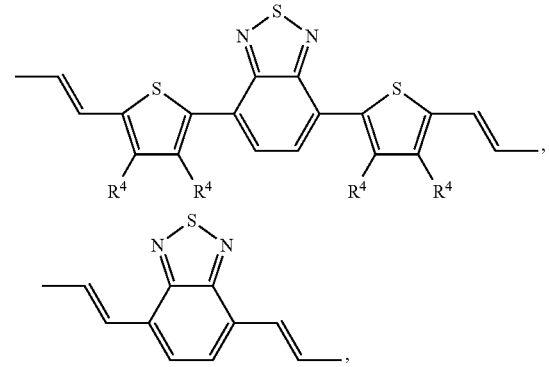

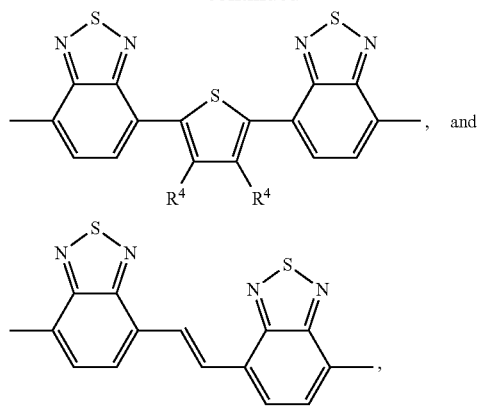, and

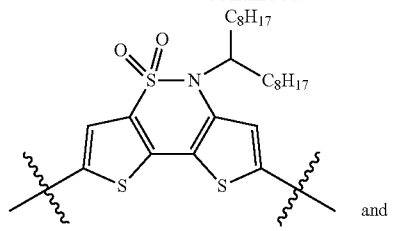 and wherein R⁴ is as defined herein.

In preferred embodiments, the present polymers are copolymers of $M_1$ and at least one $M_2$, where $M_2$ is selected from:

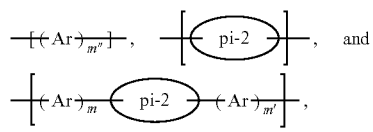, and

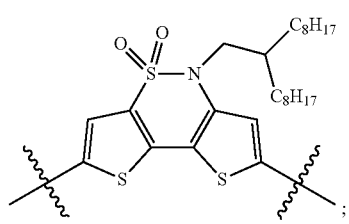;

where pi-2, Ar, m, m', and m" are as defined herein.

Certain embodiments of the present copolymers can be represented by a formula selected from the group consisting of:

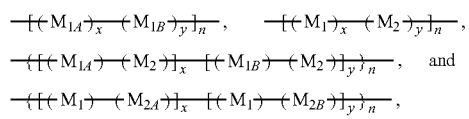 and

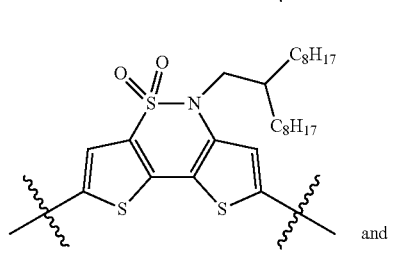 and where $M_{1A}$ and $M_{1B}$ represent different repeating units having the formula $M_1$, and $M_{2A}$ and $M_{2B}$ represent different repeating units having the formula $M_2$, x and y are real numbers representing molar ratios, and n is the degree of polymerization. To illustrate, $M_{1A}$ and $M_{1B}$ can be:

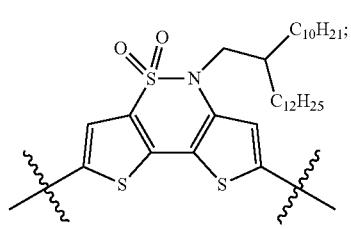

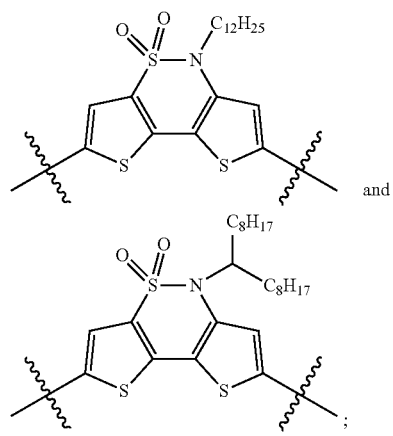

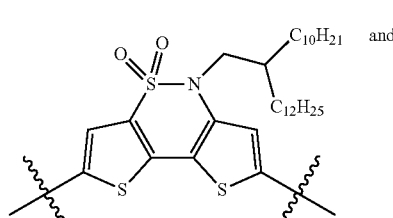

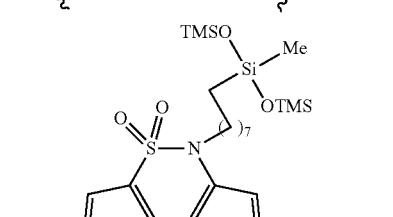 and

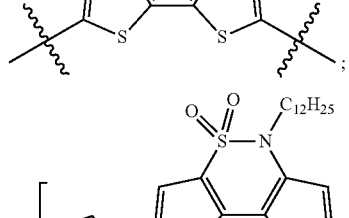;

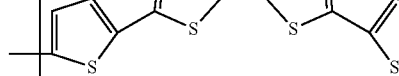 and

-continued

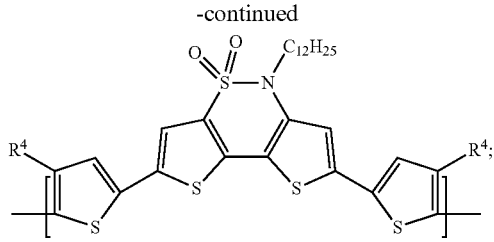

where R⁴ is as defined herein.

A particular embodiment of the present compound can be a copolymer having the repeating units $M_{1A}$ and $M_{1B}$:

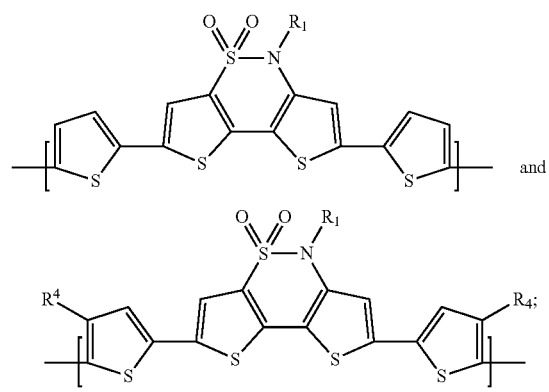

where $R^1$ and $R^4$ are as defined herein; particularly, $R^1$ is a linear or branched $C_{6-40}$ alkyl group, and $R^4$ is a linear or branched $C_{1-40}$ alkyl or haloalkyl group.

To illustrate further, $M_{2A}$ and $M_{2B}$ can be:

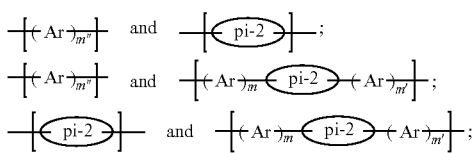

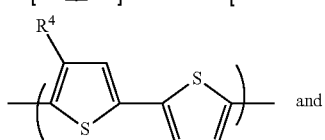

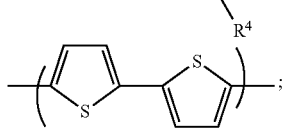

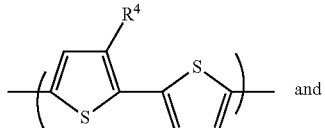

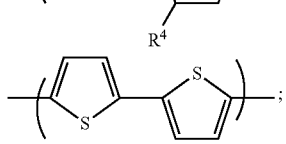

or two repeating units represented by:

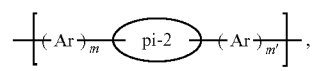

where both $(Ar)_m$ and $(Ar)_{m'}$ are

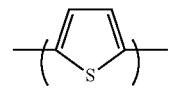

in $M_{2A}$, and both $(Ar)_m$ and $(Ar)_{m'}$ are

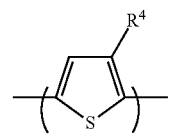

in $M_{2B}$, and pi-2 is as defined herein and can be identical or different in $M_{2A}$ and $M_{2B}$.

Exemplary polymers according to the present teachings include:

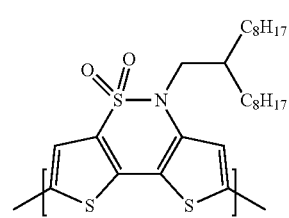

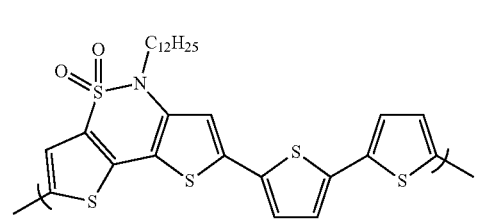

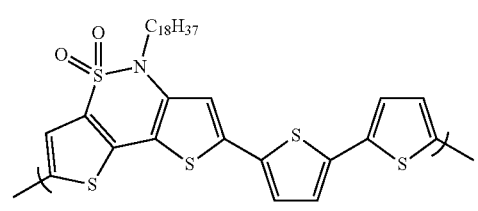

-continued

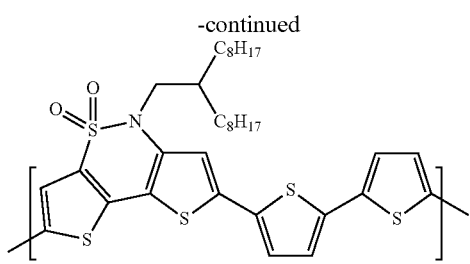

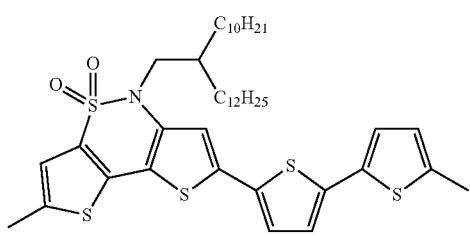

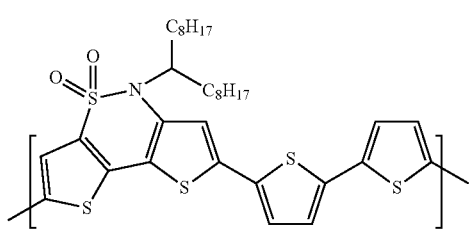

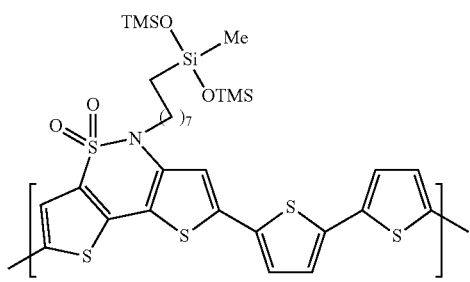

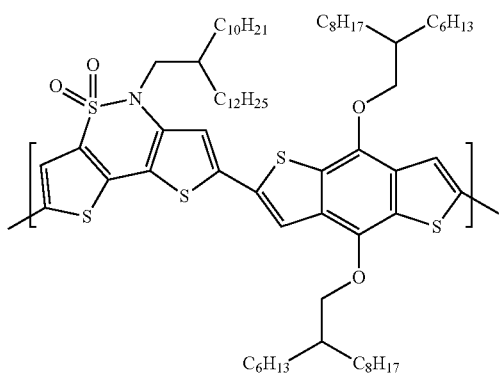

-continued

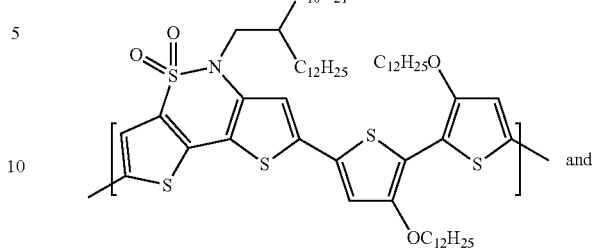

and

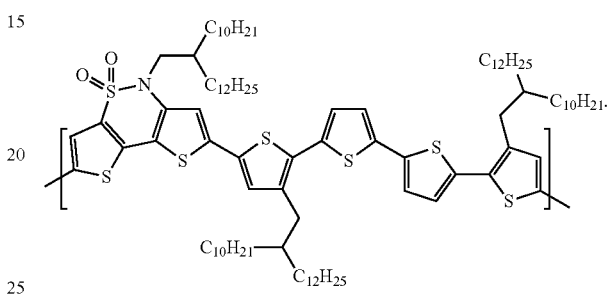

For the various polymers described above, the degree of polymerization (n) can be an integer between 3 and 1,000. In some embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100. Embodiments of the present compounds including two or more different repeating units can have such repeating units repeating in a random or alternating manner, and the mole fraction of the two units can be between about 0.05 and about 0.95. For example, the respective mole fractions (x and y) of the two units can be between about 0.1 and about 0.9, between about 0.2 and about 0.8, between about 0.3 and about 0.7, between about 0.4 and about 0.6, or between about 0.45 and about 0.55. In certain embodiments, the present polymers can include the same mole fraction of the first unit as the second unit (i.e., x=y=0.5).

In some embodiments, the present compound can be a molecular compound including at least one bithiophene sulfonamide moiety and one or more linear and/or cyclic conjugated moieties, such that the compound as a whole provides a pi-extended conjugated system.

To illustrate, exemplary small-molecule semiconducting compounds including at least one bithiophene sulfonamide moiety and monomers for preparing the polymers described herein can be represented by the following formulae:

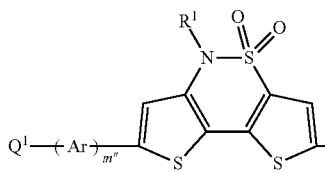

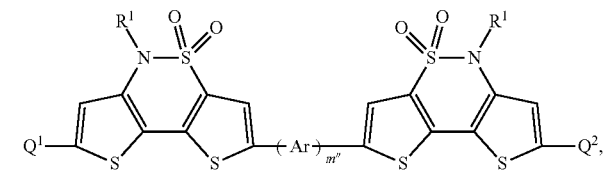

-continued
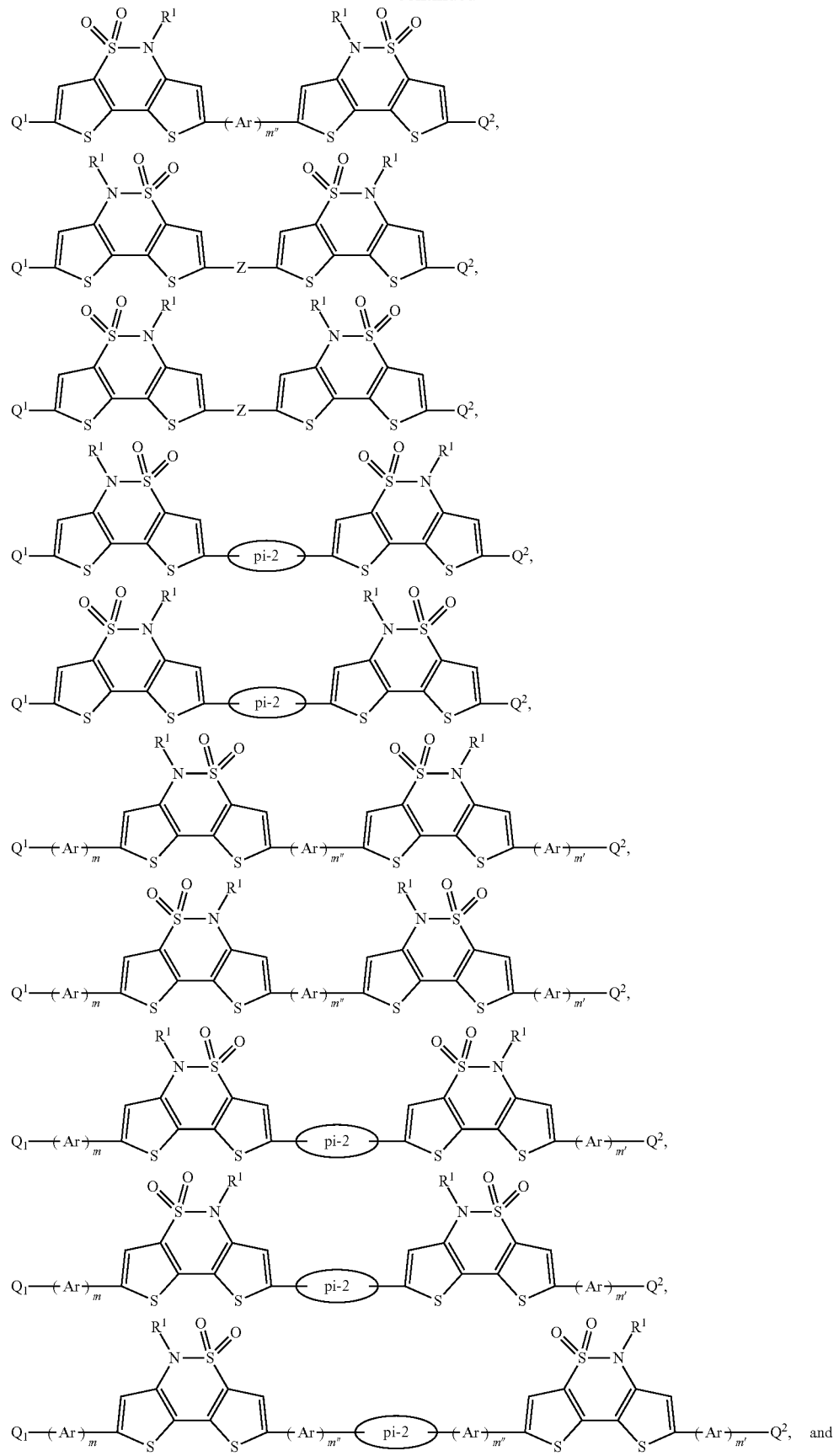

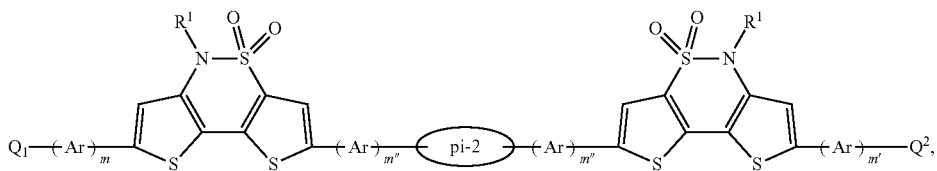

where $Q^1$ can be $X^1$ or $T^1$, $Q^2$ can be $X^2$ or $T^2$, where $X^1$ and $X^2$ can be identical or different reactive groups such as a halide, an organotin group, a boronate, or a polymerizable group, $T^1$ and $T^2$ can be identical or different terminal groups selected from H, R, and C(O)R, where R is a $C_{1-40}$ alkyl or haloalkyl group; and pi-2, Ar, Z, m, m', m", p, and p' are as defined herein.

Certain embodiments of molecular semiconducting compounds according to the present teachings can be represented by a formula selected from:

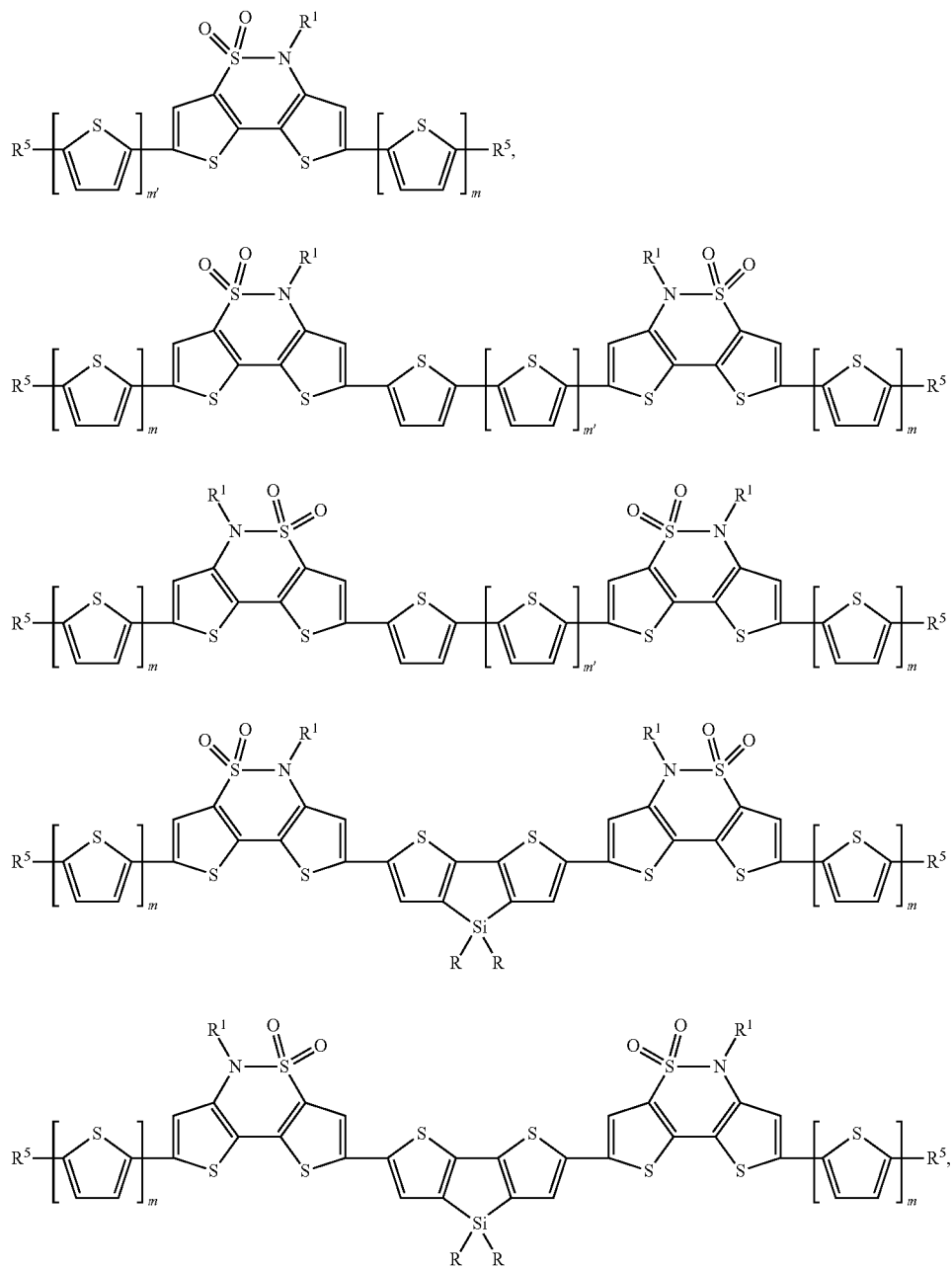

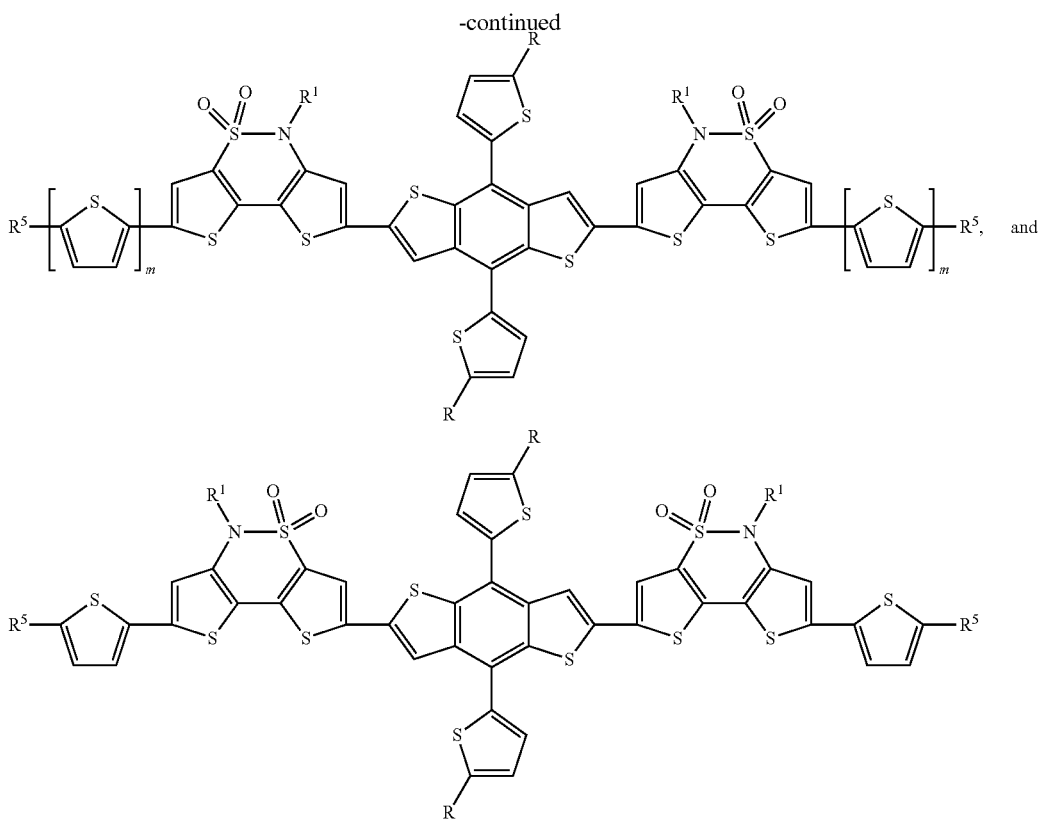

where $R^5$ is H or R; and $R^1$, R, m and m' are as defined herein.

Specific exemplary molecular semiconducting compounds according to the present teachings include:

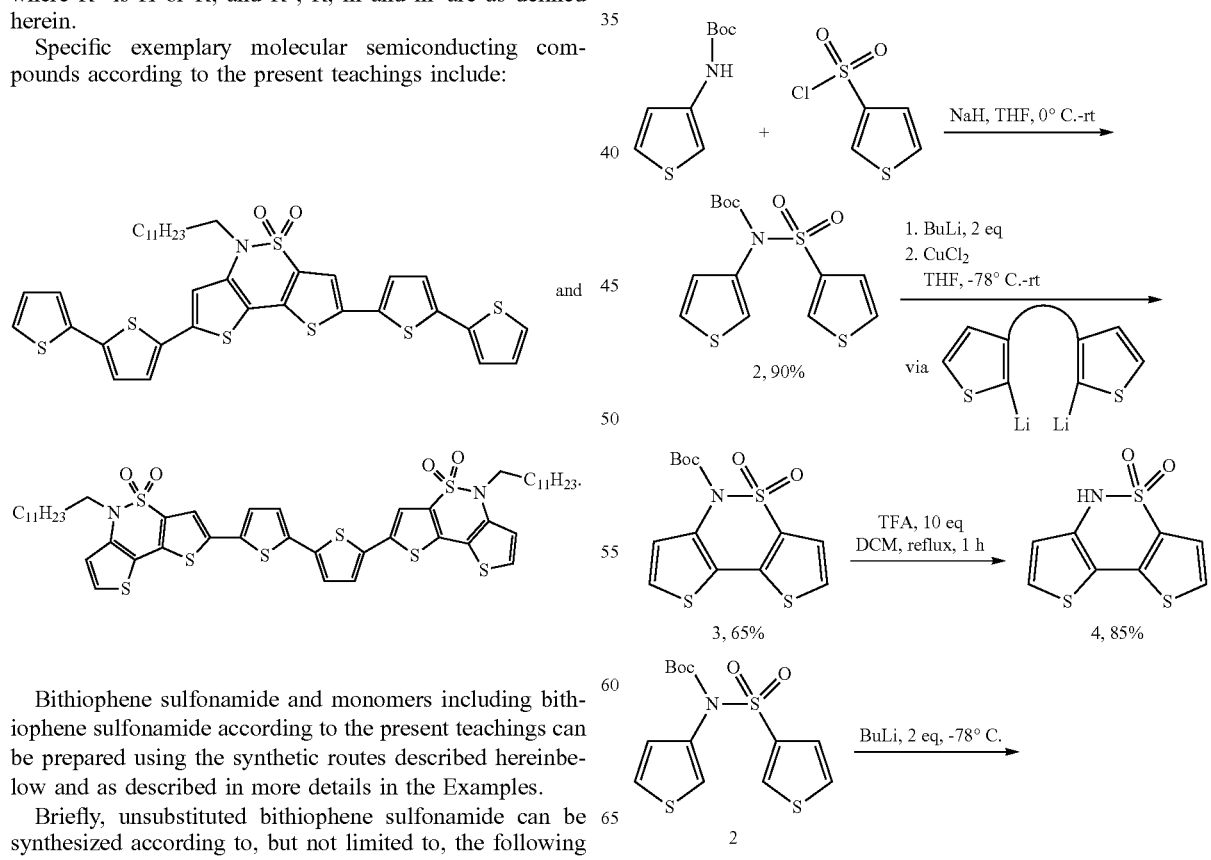

Bithiophene sulfonamide and monomers including bithiophene sulfonamide according to the present teachings can be prepared using the synthetic routes described hereinbelow and as described in more details in the Examples.

Briefly, unsubstituted bithiophene sulfonamide can be synthesized according to, but not limited to, the following routes.

-continued

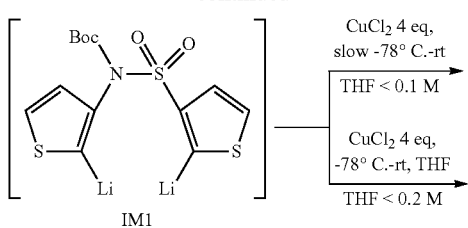

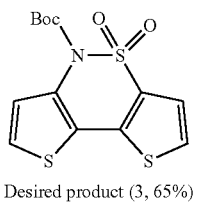

Desired product (3, 65%)

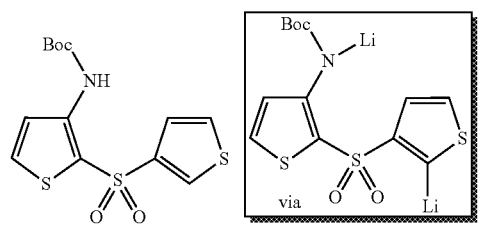

Product of [1,3] RSO₂ migration (3', 30-50%)

N-alkyl substituted bithiophene sulfonamides and its dibrominated derivatives can be synthesized as follows:

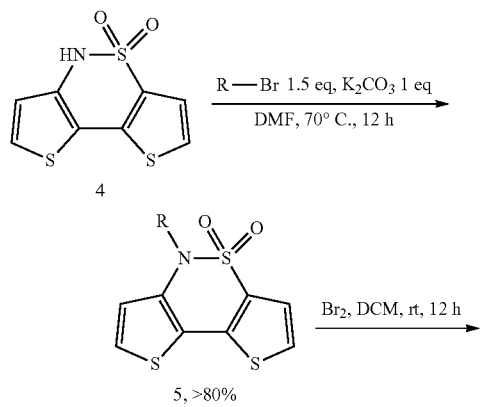

-continued

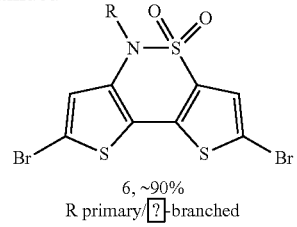

6, ~90%
R primary/[?]-branched

The brominated or metallated (see infra) bithiophene sulfonamide derivatives then can be used as an $M_1$ unit for copolymerization with an $M_2$ unit having complementary reactive groups. Or, the brominated or metallated bithiophene sulfonamide can be reacted with one or more Sp groups having complementary reactive groups to provide a pi-extended semiconducting compound. Suitable complementary reactive groups used in various coupling or polymerization reactions are well known in the art. In particular, Stille coupling or Suzuki coupling reactions can be used as described in Yamamoto, *J. Organomet. Chem.*, 653: 195-199 (2002); Walton et al., *Polymer Chemistry* (Fred J. Davis ed. 2004), p. 158-187; and Galbrecht et al., *Macromolecular Rapid Communications*, 28(4): 387-394 (2007).

The homopolymerization of $M_1$ and the copolymerization of $M_1$ and $M_2$ can be achieved via various reactions known to those skilled in the art including, but not limited to, those outlined below. It should be understood that the polymerizable groups (e.g., $SnR_3$, $BR_2$, $MgX$, $ZnX$, and Br, where X is a halogen and R is an alkyl group) can be reversed between $M_1$ and $M_2$.

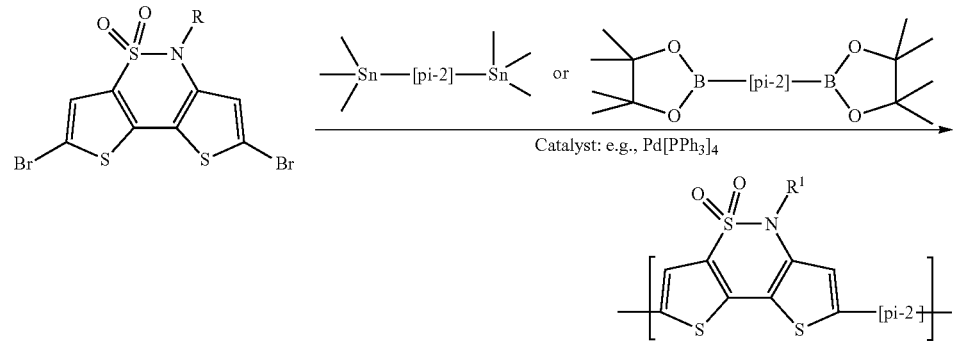

To illustrate, a copolymer of a repeating unit $M_1$ comprising only a bithiophene sulfonamide moiety and a repeating unit $M_2$ comprising only a pi-2 moiety can be prepared as follows:

The reactions above can be used analogously to couple a dibrominated bithiophene sulfonamide derivative to one or more Sp groups having complementary reactive groups to provide a more extended $M_1$ unit such as:

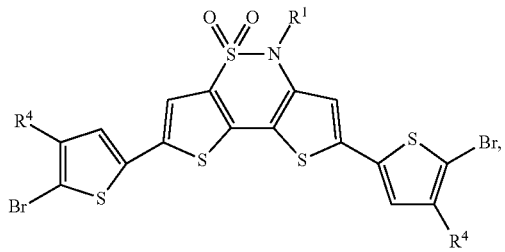

which then can be used to copolymerize with a repeating unit $M_2$ (e.g., a repeating unit $M_2$ comprising only a pi-2 moiety) as shown below, where $R^4$ is a 2-decyldodecyl group:

coupled to one or more linear and/or cyclic conjugated moieties having complementary reactive groups to provide molecular semiconducting compounds according to the present teachings. For example, two representative procedures are illustrated below:

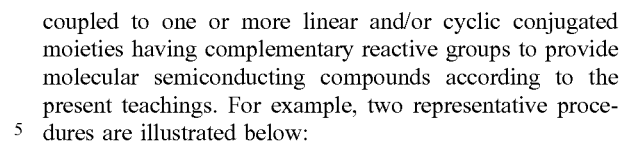

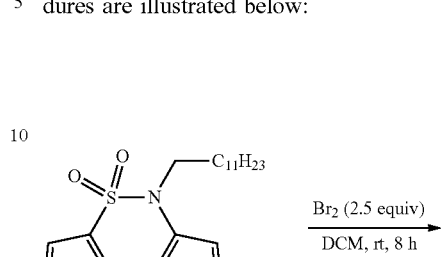

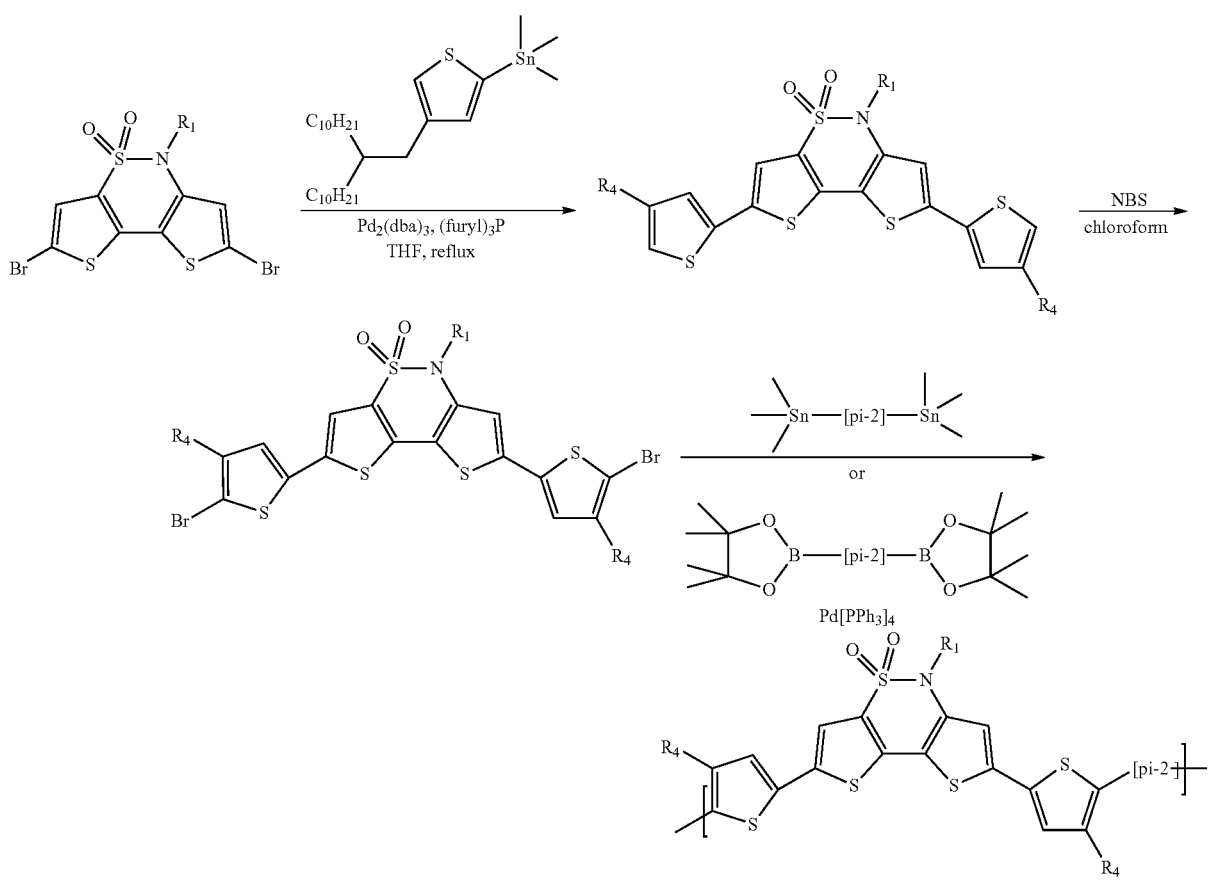

Without wishing to be bound by any particular theory, it is believed that polymers of the present teachings that have a regioregular polymeric backbone can lead to higher molecular weights, a more π-conjugated structure and, consequently better charge transport efficiencies. Accordingly, in preparing the present polymers, the present teachings can include isolating a particular average molecular weight fractions, and/or enriching and/or isolating a particular stereoisomer of $M_1$ and/or $M_2$ that has two or more stereoisomers.

Using analogous procedures, either a monobrominated or dibrominated bithiophene sulfonamide derivative can be -continued

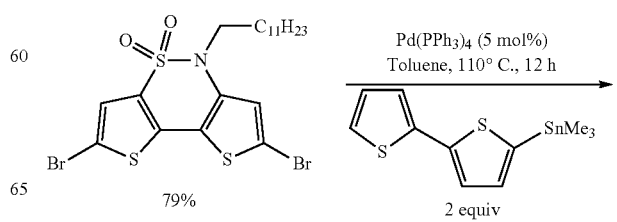

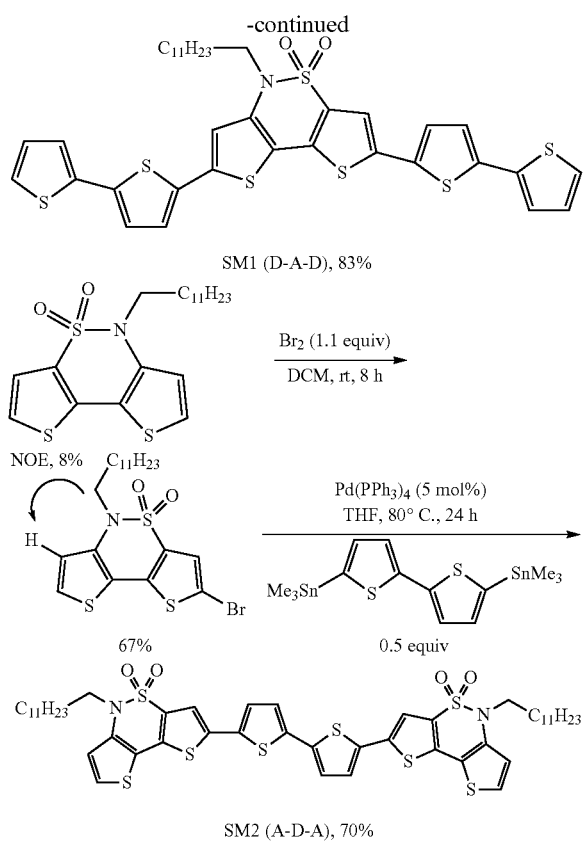

SM1 (D-A-D), 83%

SM2 (A-D-A), 70%

The semiconducting compounds disclosed herein can be stable in ambient conditions ("ambient stable") and soluble in common solvents. As used herein, a compound can be considered electrically "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a compound according to the present teachings can be described as ambient stable if its carrier mobility or redox potential does not vary more than 20% or more than 10% from its initial value after exposure to ambient conditions, including, air, humidity and temperature, over a 3 day, 5 day, or 10 day period. In addition, a compound can be considered ambient stable if the optical absorption of the corresponding film does not vary more than 20% (preferably, does not vary more than 10%) from its initial value after exposure to ambient conditions, including air, humidity and temperature, over a 3 day, 5 day, or 10 day period.

OTFTs based on the present compounds can have long-term operability and continued high-performance in ambient conditions. For example, OTFTs based on certain embodiments of the present compounds can maintain satisfactory device performance in highly humid environment. Certain embodiments of the present compounds also can exhibit excellent thermal stability over a wide range of annealing temperatures. Photovoltaic devices can maintain satisfactory power conversion efficiencies over an extended period of time.

As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. The present compounds can have room temperature solubilities in conventional organic solvents such as xylene, dichlorobenzene (DCB), and other chlorinated hydrocarbons (CHCs) as high as 60 g/L.

The present compounds can be fabricated into various articles of manufacture using solution processing techniques in addition to other more expensive processes such as vapor deposition. Various solution processing techniques have been used with organic electronics. Common solution processing techniques include, for example, spin coating, drop-casting, zone casting, dip coating, blade coating, or spraying. Another example of solution processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Compounds of the present teachings can be used to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconductor activity, ambipolar activity, light absorption, and light emission.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatibilizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as thin film semiconductors, field effect transistors (e.g., thin film transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices. For example, articles of manufacture such as the various devices described herein can include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., *PNAS,* 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Particularly, polymers of the present teachings can exhibit broad optical absorption and/or a tuned redox properties and bulk carrier mobilities, making them desirable for such applications. For example, the polymers described herein can be used as a donor (p-type) semiconductor in a photovoltaic design, which includes an adjacent n-type semiconductor material that forms a p-n junction. The polymers can be in the form of a thin film semiconductor, which can be deposited on a substrate to form a composite. Exploitation of polymers of the present teachings in such devices is within the knowledge of a skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 1 illustrates the four common types of OFET structures: (a) bottom-gate top-contact structure, (b) bottom-gate bottom-contact structure, (c) top-gate bottom-contact structure, and (d) top-gate top-contact structure. As shown in FIG. 1, an OFET can include a dielectric layer (e.g., shown as 8, 8', 8", and 8'" in FIGS. 1*a*, 1*b*, 1*c*, and 1*d*, respectively), a semiconductor/channel layer (e.g., shown as 6, 6', 6", and 6'" in FIGS. 1*a*, 1*b*, 1*c*, and 1*d*, respectively), a gate contact (e.g., shown as 10, 10', 10", and 10'" in FIGS. 1*a*, 1*b*, 1*c*, and 1*d*, respectively), a substrate (e.g., shown as 12, 12', 12", and 12'" in FIGS. 1*a*, 1*b*, 1*c*, and 1*d*, respectively), and source and drain contacts (e.g., shown as 2, 2', 2", 2'", 4, 4', 4", and 4'" in FIGS. 1*a*, 1*b*, 1*c*, and 1*d*, respectively).

In certain embodiments, OTFT devices can be fabricated with the present semiconducting compounds on doped silicon substrates, using $SiO_2$ as the dielectric, in top-contact geometries. In particular embodiments, the active semiconductor layer which incorporates at least a semiconducting compound of the present teachings can be deposited at room temperature or at an elevated temperature. In other embodiments, the active semiconductor layer which incorporates at least one semiconducting compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a semiconducting compound of the present teachings can be deposited at room temperature or at an elevated temperature. In other embodiments, the active semiconducting layer which incorporates at least a semiconducting compound of the present teachings can be applied by spin-coating or printing as described herein. Gate and source/drain contacts can be made of Au, other metals, or conducting polymers and deposited by vapor-deposition and/or printing.

Figure 2:
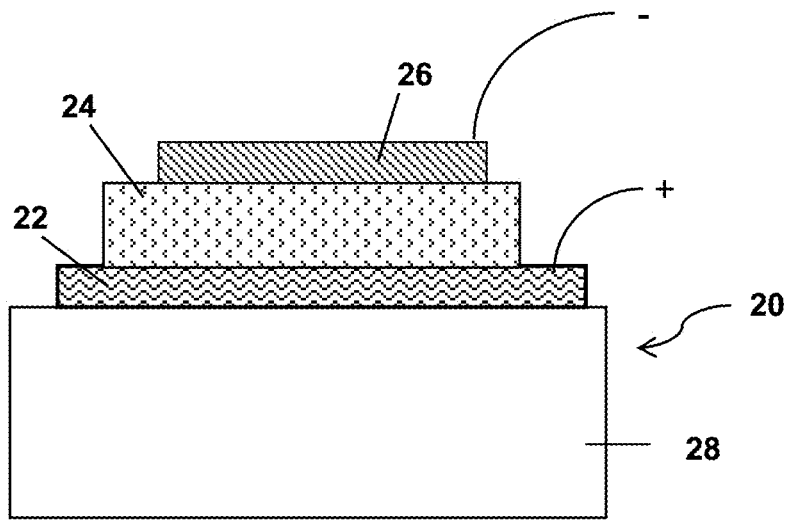
FIG. 2 illustrates a representative structure of a bulk-heterojunction organic photovoltaic device (also known as a solar cell), which can incorporate one or more compounds of the present teachings as the donor and/or acceptor materials.
Figure 3:
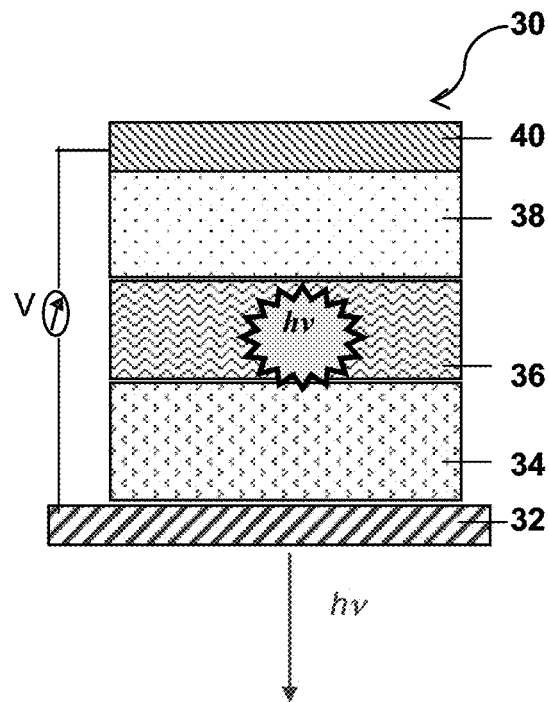
FIG. 3 illustrates a representative structure of an organic light-emitting device, which can incorporate one or more compounds of the present teachings as electron-transporting and/or emissive and/or hole-transporting materials.

Similarly, another aspect of the present teachings relates to methods of fabricating an organic light-emitting transistor, an organic light-emitting diode (OLED), or an organic photovoltaic device that incorporates one or more semiconductor materials of the present teachings. FIG. 2 illustrates a representative structure of a bulk-heterojunction organic photovoltaic device (also known as solar cell) which can incorporate one or more semiconducting compounds of the present teachings as the donor material. As shown, a representative solar cell generally includes a substrate 20 (e.g., glass), an anode 22 (e.g., ITO), a cathode 26 (e.g., aluminium or calcium), and an active layer 24 between the anode and the cathode which can incorporate one or more semiconducting compounds of the present teachings as the electron donor (p-channel) materials. FIG. 3 illustrates a representative structure of an OLED which can incorporate one or more semiconducting compounds of the present teachings as electron-transporting and/or emissive and/or hole-transporting materials. As shown, an OLED generally includes a substrate 30 (not shown), a transparent anode 32

(e.g., ITO), a cathode 40 (e.g., metal), and one or more organic layers which can incorporate one or more semiconducting compounds of the present teachings as hole-transporting (n-channel) (layer 34 as shown) and/or emissive (layer 36 as shown) and/or electron-transporting (p-channel) materials (layer 38 as shown).

The following examples are provided to illustrate further and to facilitate the understanding of the present teachings and are not in any way intended to limit the invention. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

All reagents were purchased from commercial sources and used without further purification unless otherwise noted. Conventional Schlenk techniques were used and reactions were carried out under $N_2$ unless otherwise noted.

Characterization data are provided in some cases by $^1$H-NMR, optical absorption spectroscopy, and cyclic voltammetry. NMR spectra were recorded on an Inova 500 NMR spectrometer ($^1$H, 500 MHz). UV-vis spectra were recorded on a Cary 50 UV-vis spectrophotometer. Cyclic voltammetry measurement was carried out under nitrogen at a scan rate of 50 mV/s using a BAS-CV-50W voltammetric analyzer. A platinum disk working electrode, a platinum wire counter electrode and a silver wire reference electrode were employed and Fc/Fc$^+$ (0.54 V vs SCE) was used as reference for all measurements.

Example 1

Synthesis of Bithiophene Sulfonamide (BTSA) Monomeric Units

Example 1A

Synthesis of Unsubstituted Bithiophene Sulfonamide

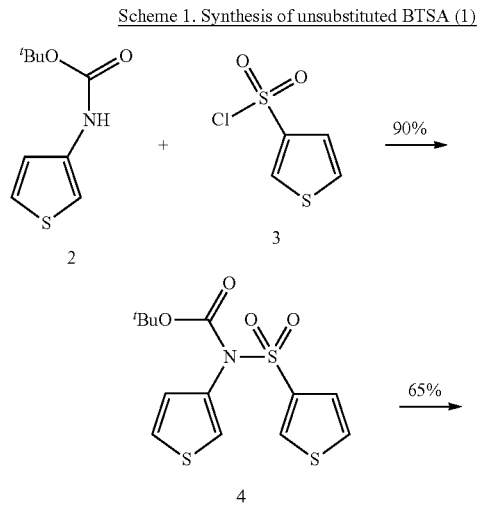

Scheme 1. Synthesis of unsubstituted BTSA (1)

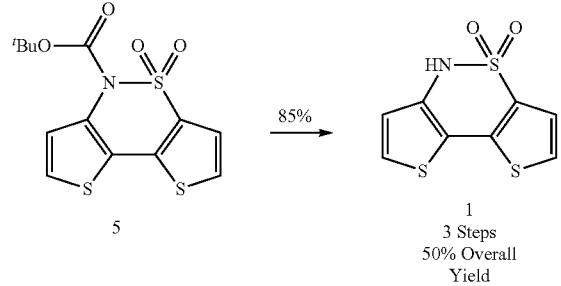

1
3 Steps
50% Overall Yield

Scheme 1 above shows a 3-step procedure for preparing bithiophene sulfonamide (1) starting from commercially available tert-butyl thiophen-3-ylcarbamate (2) and thiophene-3-sulfonyl chloride (3). The overall yield of the product 1 is about 50%. Details of the synthesis as well as the characterization of the various intermediates and final compound are given below.

Step 1—Preparation of tert-butyl thiophen-3-yl(thiophen-3-ylsulfonyl)carbamate (4)

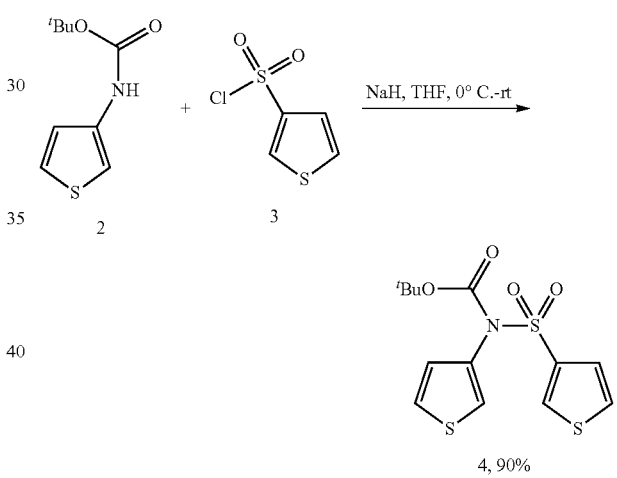

4, 90%

A 50 ml Schlenk flask was charged with a magnetic stirrer bar and 95% NaH (365 mg, 15.2 mmol, 1.02 equiv) under a nitrogen atmosphere (glove box). The flask was capped with a rubber septum, then 10 ml of dry THF was added. The resulting slurry was cooled to 0° C. and a solution of tert-butyl thiophen-3-ylcarbamate (2) (3000 mg, 15 mmol, 1 equiv) in 10 ml of dry THF was added to the mixture via a syringe for 5 minutes. After the addition was complete, the mixture was allowed to warm up to room temperature and was stirred at room temperature for 1 hour. Then, the reaction mixture was cooled down again to 0° C. and a solution of thiophene-3-sulfonyl chloride (3) (2748 mg, 15 mmol, 1 equiv) in 10 ml of dry THF was added via a syringe for 10 minutes. After the addition was complete, the cooling bath was removed and the reaction mixture was stirred at room temperature overnight. After that, the mixture was poured into an excess of ammonium chloride and extracted with dichloromethane (2×100 ml). The combined organic layers were washed with water and brine and dried over $Na_2SO_4$. The solvent was removed under reduced pressure and the residue was recrystallized from $^i$PrOH affording the product 4 (4657 mg, 13.5 mmol) as a light yellow solid at 90% yield. $^1$H NMR (499 MHz, CDCl$_3$) δ 8.12 (dd, J=3.1, 1.3 Hz, 1H), 7.45 (dd, J=5.2, 1.3 Hz, 1H), 7.41 (dd, J=5.2, 3.1 Hz, 1H), 7.30 (dd, J=5.1, 3.2 Hz, 1H), 7.23 (dd, J=3.2, 1.4 Hz, 1H) 1.38 (s, 9H). $^{13}$C NMR (CDCl$_3$) δ 150.59, 138.66, 133.17, 133.01, 127.18, 127.15, 126.41, 124.93, 124.36, 84.65, 27.82. HRMS (ESI-TOF) m/z: [M+Na]$^+$ Calcd. for C$_{13}$H$_{15}$NNaO$_4$S$_3$ 368.0054. Found 368.0055.

Step 2—Preparation of tert-butyl 5H-dithieno[3,2-c: 2',3'-e][1,2]thiazine-5-carboxylate 4,4-dioxide (5)

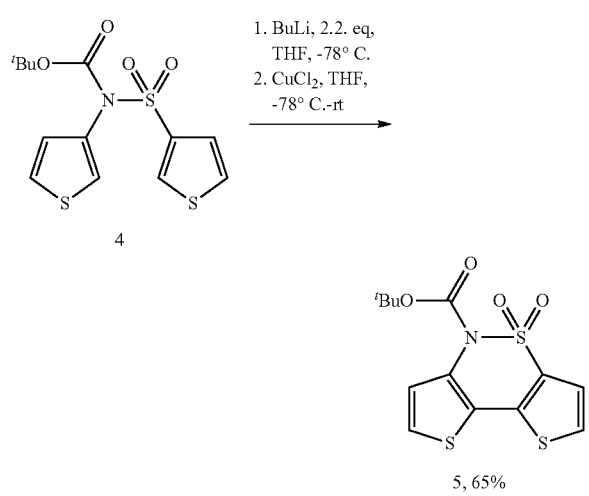

A 250 ml Schlenk flask was charged with a magnetic stirrer bar and compound 4 (2205 mg, 6.4 mmol, 1 equiv). The flask was evacuated and backfilled with N$_2$ 3 times. Then, 70 ml of dry THF was added to the flask. The resulting solution was cooled down to −78° C. A 2.6 M solution of BuLi in hexanes (5.3 ml, 14.1 mmol, 2.2 equiv) was added to the reaction mixture for 5 minutes. After the addition was complete, the reaction mixture was stirred for 30 min at −78° C. Then, anhydrous CuCl$_2$ (3500 mg, 4 equiv) was added to the reaction mixture in one portion using Schlenk technique. The reaction mixture was stirred at −78° C. for an additional hour and then was slowly warmed up (overnight) to room temperature. After that, the mixture was poured into an excess of ammonium chloride and extracted with DCM (3×100 ml). The combined organic layers were washed with water and brine and dried over Na$_2$SO$_4$. The solvent was removed under reduced pressure and the residue was dissolved in DCM (20 ml) and filtered through silica gel plug (washed 3 times with DCM). The solvent was removed under reduced pressure and the product 5 was used in the next step without additional purification. To obtain an analytically pure sample, the aforementioned residue was purified via column chromatography on silica gel, using a 5:1 hexane/ethyl acetate mixture as eluent to afford the compound 5 (1426 mg, 4.16 mmol) as a white solid at 65% yield. $^1$H NMR (499 MHz, CDCl$_3$) δ 7.42 (d, J=5.3 Hz, 1H), 7.31-7.34 (m, 2H), 7.25 (d, J=5.5 Hz, 1H), 1.61 (s, 9H). $^{13}$C NMR (101 MHz, CDCl$_3$) δ 148.88, 136.88, 134.36, 130.94, 124.77, 124.60, 124.34, 122.98, 118.92, 86.52, 28.09. HRMS (ESI-TOF) m/z: [M+Na]$^+$ Calcd. for C$_{13}$H$_{13}$NNaO$_4$S$_3$ 365.9899. Found 365.9899.

Step 3—Preparation of 5H-dithieno[3,2-c:2',3'-e][1,2]thiazine 4,4-dioxide (1)

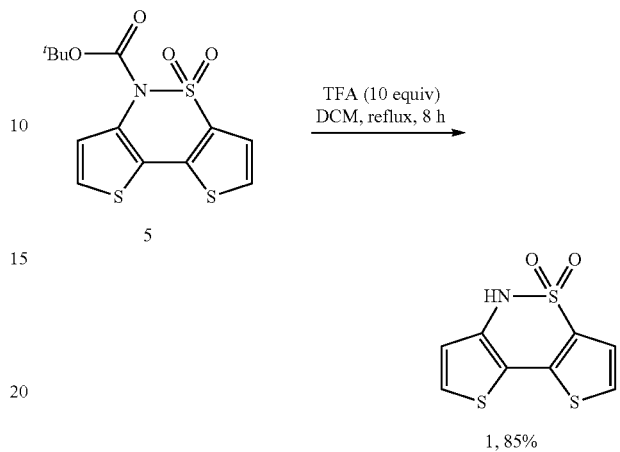

A 100 ml flask was charged with magnetic stirrer bar and substrate 5 (1750 mg, 5.1 mmol, 1 equiv). Then, DCM (50 ml) was added to the flask. The resulted solution was cooled to 0° C. and trifluoroacetic acid (TFA, 5700 mg, 50 mmol, 10 equiv) was added slowly via syringe for 5 min. After the addition completed the mixture was refluxed for 8 h. Then, the mixture was cooled to rt and the yellow solid precipitated during the reaction was filtered, washed 5 times with DCM and finally with hexane. The material was collected into Petri dish and dried in vacuo at 60° C. for 1 h to afford the product 1 (1054 mg, 4.34 mmol) as a white solid at 85% yield. $^1$H NMR (499 MHz, DMSO-d6) δ 11.87 (bs, 1H), 7.72-7.69 (m, 2H), 7.46 (d, J=5.3 Hz, 1H), 6.95 (d, J=5.3 Hz, 1H). $^{13}$C NMR (101 MHz, DMSO-d6) δ 137.43, 136.90, 128.43, 127.69, 126.01, 121.60, 120.55, 113.41. HRMS (ESI-TOF) m/z: [M+Na]$^+$ Calcd. for C$_8$H$_5$NNaO$_2$S$_3$ 265.9380. Found 265.9375.

Example 1B

Synthesis of N-alkyl substituted BTSA

Scheme 2. Synthesis of N-alkyl substituted BTSA derivatives (6a-d)

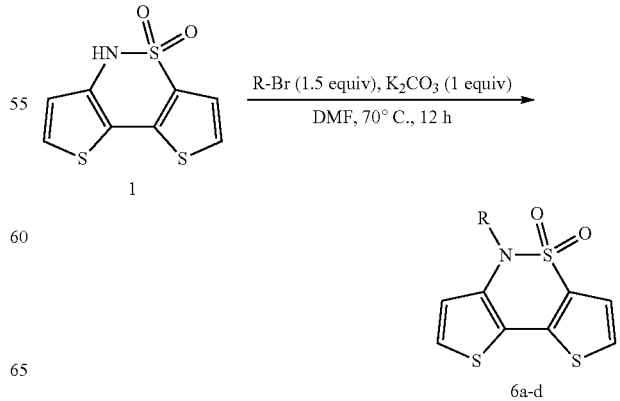

N-alkyl substituted BTSA derivatives (e.g., compounds 6a-d) can be synthesized according to the general procedure shown in Scheme 2 above. Details of the synthesis as well as the characterization of the various intermediates and final compounds are given below. A 10 ml Schlenk flask was charged with a magnetic stirrer bar, sulfonamide 1 (123 mg, 0.5 mmol) and finely grounded $K_2CO_3$ (69 mg, 0.5 mmol, 1 equiv). The flask was evacuated and backfilled with $N_2$ 3 times and 5 ml of dry DMF was added. The mixture was stirred at 70° C. for 1 h after that corresponding alkyl bromide (1.5 equiv) was added via a syringe. For the syntheses of 6c and 6d, corresponding alkyl bromides were synthesized according to Scheme 2a below. The reaction mixture was kept stirring at 70° C. for 12 h. Then, the mixture was cooled down and the solvent DMF was removed under reduced pressure. The residue was purified via column chromatography on silica gel, using a 1:1 hexane/DCM mixture as the eluent.

$J=7.0$ Hz, 6H). $^{13}$C NMR (126 MHz, $CDCl_3$) δ 138.60, 136.77, 128.39, 125.42, 123.88, 121.61, 119.81, 116.12, 51.47, 36.80, 31.89, 31.04, 29.76, 29.64, 29.62, 29.60, 29.57, 29.56, 29.40, 29.32, 29.30, 26.18, 22.65, 14.08. Some signals may overlap.

Preparation of 5-(2-tetradecylhexadecyl)-5H-dithieno[3,2-c:2',3'-e][1,2]thiazine 4,4-dioxide (6c) and 5-(2-tetradecyloctadecyl)-5H-dithieno[3,2-c:2,3'-e][1,2]thiazine 4,4-dioxide (6d)

The alkyl bromides, 14-(2-bromoethyl)octacosane $(BrCH_2CH(C_{14}H_{29})_2$ (1A) and 15-(2-bromoethyl)triacontane $(BrCH_2CH(C_{14}H_{29})(C_{16}H_{33})$ (1B) used to prepare 6c and 6d were synthesized according to Scheme 2a below.

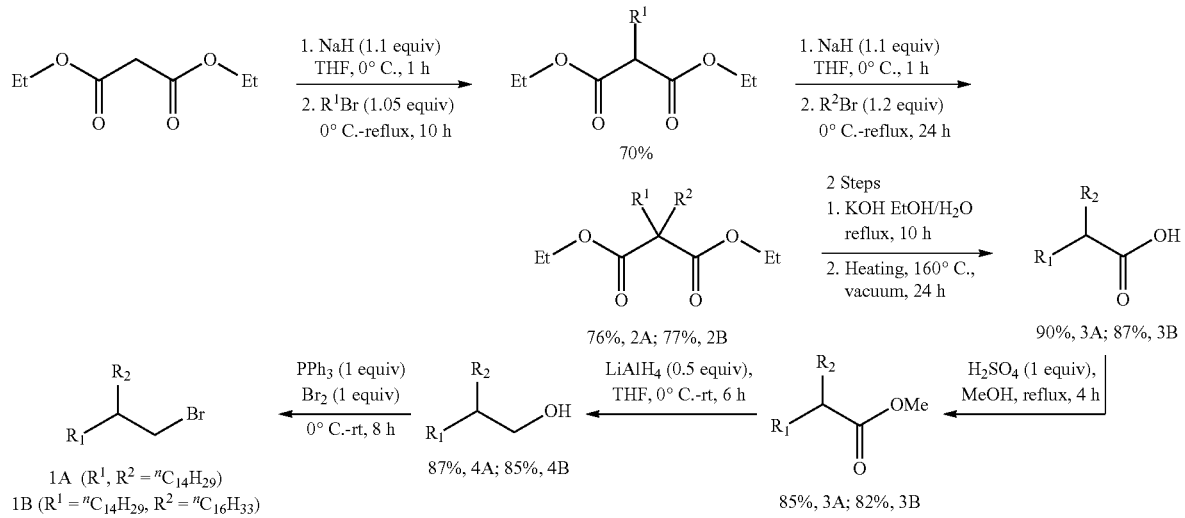

Scheme 2a. Synthesis of alkyl bromides 1A and 1B

Characterization of 5-dodecyl-5H-dithieno[3,2-c:2',3'-e][1,2]thiazine 4,4-dioxide (6a)

The product 6a (201.29 mg, 0.49 mmol) was isolated as a colorless viscous oil at 98% yield. $^1$H NMR (499 MHz, $CDCl_3$) δ 7.39 (d, J=5.4 Hz, 1H), 7.38 (d, J=5.4 Hz, 1H), 7.30 (d, J=5.2 Hz, 1H), 7.00 (d, J=5.4 Hz, 1H), 3.94 (t, J=7.5 Hz, 2H), 1.69-1.71 (m, 2H), 1.15-1.36 (m, 18H), 0.89 (t, J=6.9 Hz, 3H). $^{13}$C NMR (101 MHz, $CDCl_3$) δ 138.68, 136.97, 128.11, 125.66, 123.88, 121.54, 119.44, 115.62, 47.90, 31.88, 29.57, 29.44, 29.40, 29.31, 29.22, 29.03, 26.52, 22.66, 14.10. Some signals may overlap.

Characterization of 5-(2-decyltetradecyl)-5H-dithieno[3,2-c:2',3'-e][1,2]thiazine 4,4-dioxide (6b)

The product 6b (201.29 mg, 0.49 mmol) was isolated as a colorless viscous oil at 69% yield. 1H NMR (499 MHz, $CDCl_3$) δ 7.39 (d, J=5.3 Hz, 1H), 7.37 (d, J=5.4 Hz, 1H), 7.30 (d, J=5.4 Hz, 1H), 7.00 (d, J=5.4 Hz, 1H), 3.85 (d, J=7.5 Hz, 2H), 1.61-1.73 (m, 1H), 1.04-1.40 (m, 40H), 0.89 (t, Characterization of 14-(2-bromoethyl)octacosane $(BrCH_2CH(C_{14}H_{29})_2$ (1A)

The product 1A was obtained as a white solid. $^1$H NMR (499 MHz, $CDCl_3$) δ 3.44 (d, J=4.8 Hz, 2H), 1.55-1.64 (m, 1H), 1.20-1.40 (m, 52H), 0.88 (t, J=6.9 Hz, 6H). $^{13}$C NMR (126 MHz, $CDCl_3$) δ 39.72, 39.49, 32.54, 31.91, 29.76, 29.68, 29.67, 29.65, 29.61, 29.57, 29.35, 26.54, 22.68, 14.10. Some signals may overlap.

Characterization of 15-(2-Bromoethyl)triacontane $(BrCH_2CH(C_{14}H_{29})(C_{16}H_{33})$ (1B)

The product 1B was obtained as a white solid. 1H NMR (499 MHz, $CDCl_3$) δ 3.44 (d, J=4.8 Hz, 2H), 1.56-1.62 (m, 1H), 1.20-1.40 (m, 56H), 0.88 (t, J=6.9 Hz, 6H). $^{13}$C NMR (126 MHz, $CDCl_3$) δ 39.67, 39.48, 32.53, 31.90, 29.75, 29.67, 29.66, 29.64, 29.60, 29.56, 29.34, 26.53, 22.66, 14.08. Some signals may overlap.

Characterization of 5-(2-tetradecylhexadecyl)-5H-dithieno[3,2-c:2',3'-e][1,2]thiazine 4,4-dioxide (6c)

The product 6c (199 mg, 0.3 mmol) was isolated as a colorless viscous oil at 60% yield. $^1$H NMR (499 MHz, CDCl$_3$) δ 7.37 (m 2H), 7.29 (d, J=5.3 Hz, 1H), 6.99 (d, J=5.4 Hz, 1H), 3.85 (d, J=7.5 Hz, 2H), 1.61-1.71 (m, 1H), 0.98-1.36 (m, 52H), 0.88 (t, J=6.8 Hz, 6H). $^{13}$C NMR (126 MHz, CDCl$_3$) δ 138.60, 136.77, 128.39, 125.43, 123.89, 121.60, 119.81, 116.11, 51.46, 36.79, 31.90, 31.03, 29.77, 29.68, 29.66, 29.64, 29.62, 29.59, 29.41, 29.34, 26.18, 22.67, 14.09. Some signals may overlap.

Characterization of 5-(2-tetradecyloctadecyl)-5H-dithieno[3,2-c:2',3'-e][1,2]thiazine 4,4-dioxide (6d)

The product 6d (305 mg, 0.44 mmol) was isolated as a colorless viscous oil at 88% yield. $^1$H NMR (499 MHz, CDCl$_3$) δ 7.37 (m, 2H), 7.29 (d, J=5.3 Hz, 1H), 6.99 (d, J=5.4 Hz, 1H), 3.84 (d, J=7.4 Hz, 2H), 1.61-1.69 (m, 1H), 1.07-1.34 (m, 56H), 0.88 (t, J=6.8 Hz, 7H). $^{13}$C NMR (126 MHz, CDCl$_3$) δ 138.59, 136.77, 128.39, 125.43, 123.89, 121.61, 119.81, 116.12, 51.46, 36.79, 31.90, 31.03, 29.77, 29.68, 29.65, 29.63, 29.62, 29.58, 29.41, 29.34, 26.18, 22.66, 14.09. Some signals may overlap.

Preparation of 5-(heptadecan-9-yl)-5H-dithieno[3,2-c:2',3'-e][1,2]thiazine 4,4-dioxide (6)

The compound 6e was synthesized according to Scheme 2b below.

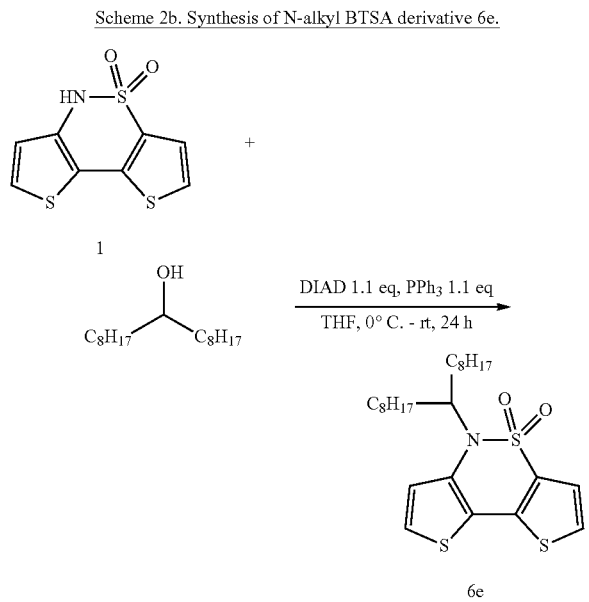

Specifically, a 10 ml Schlenk flask was charged with a magnetic stirrer bar, sulfonamide 1 (123 mg, 0.5 mmol), heptadecan-9-ol (153.9 mg, 0.6 mmol, 1.2 equiv) and triphenylphosphine (157.2, 0.6 mmol, 1.2 equiv). The flask was evacuated and backfilled with N$_2$ 3 times and 10 ml of dry THF was added. The mixture was cooled down to 0° C. Then, a solution of diisopropyl azodicarboxylate (DIAD, 123 mg 0.6 mmol, 1.2 equiv) in 2 ml of THF was slowly added (over 1 h) to the reaction mixture. The reaction mixture was stirred at 0° C. for 2 h, after which it was allowed to warm up to room temperature and stirred at this temperature for 12 h. Then, the mixture was diluted with H$_2$O and extracted with diethyl ether, then dried over Na$_2$SO$_4$. The solvent was removed under reduced pressure and the residue was purified via column chromatography on silica gel using a 1:1 hexane/DCM mixture as the eluent to afford the product 6e (127 mg, 0.27 mmol) as a colorless viscous oil at 53% yield. $^1$H NMR (499 MHz, CDCl$_3$) δ 7.30-7.34 (m, 2H), 7.29 (d, J=5.3 Hz, 1H), 7.09 (d, J=5.4 Hz, 1H), 4.23-4.33 (m, 1H), 1.60-1.79 (m, 2H), 1.47-1.58 (m, 2H), 1.01-1.30 (m, 24H), 0.84 (t, J=7.1 Hz, 6H). $^{13}$C NMR (101 MHz, CDCl$_3$) δ 136.37, 130.14, 124.56, 124.34, 122.01, 121.66, 34.41, 31.79, 29.26, 29.02, 26.26, 22.59, 14.07. Some signals may overlap.

Example 1C

Synthesis of N-alkyl BTSA dibromides

Dibrominated BTSA derivatives are useful building blocks for preparing both BTSA-based polymers and pi-extended molecular semiconductors having at least one BTSA group. Such dibromides can be synthesized according to the general procedure shown in Scheme 3 below.

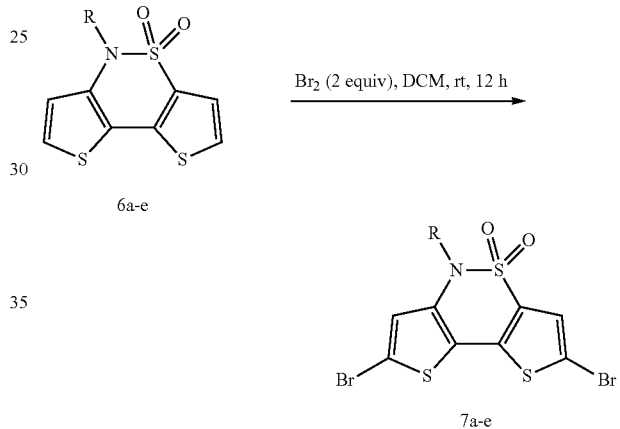

Using this procedure, dibromides 7a-e were prepared as follows. To a solution of the corresponding N-alkyl BTSA derivatives 6 (0.5 mmol) in 30 ml of DCM, a solution of Br$_2$ (190 mg, 1.2 mmol, 2.4 equiv) in 1 ml of DCM was added via a syringe over 1 min. After the addition was complete, anhydrous FeCl$_3$ (1 mg, 1 mol %) was added to the mixture. The flask was wrapped with aluminum foil to protect the reaction mixture from light, and the reaction mixture was stirred at room temperature overnight. Then, the reaction mixture was washed with a saturated aqueous solution of Na$_2$S$_2$O$_3$, then brine, and dried over Na$_2$SO$_4$. The solvent was removed under reduced pressure and the residue was purified via column chromatography on silica gel using a 2:1 hexane/DCM mixture as the eluent.

Characterization of 2,7-dibromo-5-dodecyl-5H-dithieno[3,2-c:2',3'-e][1,2]thiazine 4,4-dioxide (7a)

The product 7a (224 mg, 0.39 mmol) was isolated as a white solid at 79% yield. $^1$H NMR (499 MHz, CDCl$_3$) δ 7.34 (s, 1H), 6.99 (s, 1H), 3.87 (t, J=7.5 Hz, 2H), 1.65-1.70 (m, 2H), 1.20-1.30 (m, 18H), 0.89 (t, J=6.9 Hz, 3H). $^{13}$C NMR (126 MHz, CDCl$_3$) δ 138.24, 136.65, 128.26, 123.74, 122.38, 116.12, 114.75, 111.83, 48.27, 31.87, 29.57, 29.43, 29.38, 29.30, 29.23, 28.97, 26.44, 22.65, 14.09. Some signals may overlap.

Characterization of 2,7-dibromo-5-(2-decyltetradecyl)-5H-dithieno[3,2-c:2',3'-e][1,2]thiazine 4,4-dioxide (7b)

The product 7b (331 mg, 0.45 mmol) was isolated as a colorless viscous oil at 90% yield. $^1$H NMR (499 MHz, CDCl$_3$) δ 7.33 (s, 1H), 6.98 (s, 1H), 3.79 (d, J=7.5 Hz, 2H), 1.60-1.71 (m, 1H), 1.07-1.40 (m, 40H), 0.90 (t, J=6.9 Hz, 6H). $^{13}$C NMR (126 MHz, CDCl$_3$) δ 138.25, 136.47, 128.54, 123.81, 122.76, 116.61, 114.61, 111.94, 51.85, 36.87, 31.93, 30.96, 29.82, 29.70, 29.66, 29.64, 29.62, 29.47, 29.37, 29.35, 26.11, 22.70, 14.13. Some signals may overlap.

Characterization of 2,7-dibromo-5-(2-tetradecylhexadecyl)-5H-dithieno[3,2-c:2',3'-e][1,2]thiazine 4,4-dioxide (7c)

The product 7c (366 mg, 0.45 mmol) was isolated as a colorless viscous oil at 89% yield. $^1$H NMR (499 MHz, CDCl$_3$) δ 7.32 (s, 1H), 6.97 (s, 1H), 3.78 (d, J=7.5 Hz, 2H), 1.59-1.71 (s, 1H), 1.07-1.40 (m, 52H), 0.88 (t, J=6.9 Hz, 6H). $^{13}$C NMR (126 MHz, CDCl$_3$) δ 138.23, 136.44, 128.53, 123.79, 122.73, 116.58, 114.58, 111.91, 51.82, 36.84, 31.91, 30.94, 29.79, 29.69, 29.68, 29.64, 29.62, 29.44, 29.35, 26.09, 22.67, 14.10. Some signals may overlap.

Characterization of 2,7-dibromo-5-(2-tetradecyloctadecyl)-5H-dithieno[3,2-c:2',3'-e][1,2]thiazine 4,4-dioxide (7d)

The product 7d (374 mg, 0.44 mmol) was isolated as a colorless viscous oil at 89% yield. $^1$H NMR (499 MHz, CDCl$_3$) δ 7.30 (s, 1H), 6.95 (s, 1H), 3.76 (d, J=7.5 Hz, 1H), 1.59-1.71 (s, 1H), 1.07-1.40 (m, 56H), 0.87 (t, J=6.9 Hz, 6H). $^{13}$C NMR (126 MHz, CDCl$_3$) δ 138.22, 136.45, 128.52, 123.78, 122.73, 116.59, 114.58, 111.92, 51.82, 36.83, 31.90, 31.55, 30.93, 29.79, 29.68, 29.67, 29.64, 29.62, 29.44, 29.34, 26.09, 22.66, 22.62, 14.09. Some signals may overlap. HRMS (ESI-TOF) m/z: [M+H]$^+$ Calcd. for C$_{40}$H$_{68}$Br$_2$NO$_2$S$_3$ 848.2746. Found 848.2773.

Characterization of 2,7-dibromo-5-(heptadecan-9-yl)-5H-dithieno[3,2-c:2',3'-e][1,2]thiazine 4,4-dioxide (7e)

The product 7e (249 mg, 0.39 mmol) was isolated as a colorless viscous oil at 78% yield. $^1$H NMR (499 MHz, CDCl$_3$) δ 7.31 (s, 1H), 7.10 (s, 1H), 4.20-4.30 (bs, 1H), 1.50-1.79 (m, 4H), 1.06-1.34 (m, 24H), 0.88 (t, J=7.1 Hz, 6H). $^{13}$C NMR (126 MHz, cdcl$_3$) δ 136.03, 130.21, 124.72, 123.92, 113.77, 112.47, 34.38, 31.84, 29.32, 29.07, 28.97, 26.31, 22.64, 14.12. Some signals may overlap.

Preparation of 2,7-dibromo-5-(8-(1,1,1,3,5,5,5-heptamethyltrisiloxan-3-yl)octyl)-5H-dithieno[3,2-c:2',3'-e][1,2]thiazine 4,4-dioxide (7f)

The compound 7f was synthesized according to Scheme 3a below.

Scheme 3a. Synthesis of N-alkyl BTSA dibromide (7f)

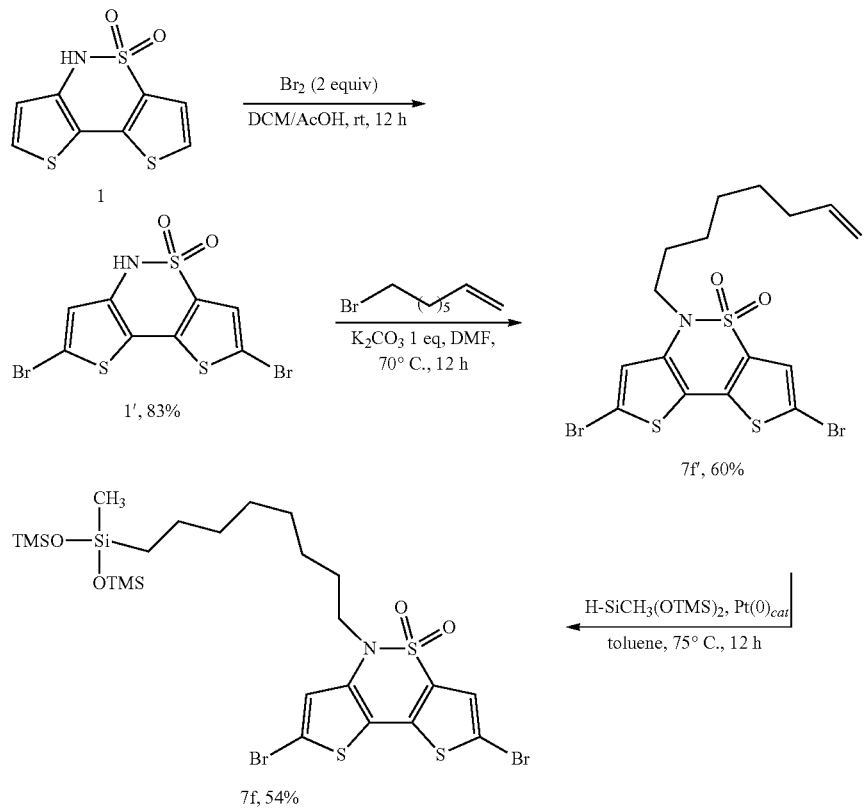

Step 1—Preparation of 2,7-dibromo-5H-dithieno[3,2-c:2',3'-e][1,2]thiazine 4,4-dioxide (1')

To a solution of BTSA 1 (243 mg, 1 mmol) in 30 ml of a 3:1 AcOH/DCM solvent mixture, a solution of $Br_2$ (480 mg, 3 mmol, 3 equiv) in 1 ml of DCM was added via a syringe over 1 min. The flask was wrapped with aluminum foil to protect the reaction mixture from light, and the reaction mixture was stirred at room temperature overnight. The yellow solid formed in the reaction mixture was filtered, then washed with DCM (5×10 ml) and hexane (2×10 ml). After drying for 2 h at 60° C. at low pressure, the compound 1' (328 mg, 0.83 mmol) was obtained as a yellow solid at 83% yield. $^1$H NMR (499 MHz, DMSO-d6) δ 7.70 (s, 1H), 7.12 (s, 1H). $^{13}$C NMR (101 MHz, DMSO-d6) δ 137.61, 136.72, 128.66, 124.48, 123.84, 114.97, 113.55, 111.87.

Step 2—Preparation of 2,7-dibromo-5-(oct-7-en-1-yl)-5H-dithieno[3,2-c:2',3'-e][1,2]thiazine 4,4-dioxide (7f')

A 10 ml Schlenk flask was charged with a magnetic stirrer bar, sulfonamide 1' (200 mg, 0.5 mmol) and finely grounded $K_2CO_3$ (69 mg, 0.5 mmol, 1 equiv). The flask was evacuated and backfilled with $N_2$ 3 times and 5 ml of dry DMF was added. The mixture was stirred at 70° C. for 1 h, after which 8-bromo-1-octene (144 mg, 1.5 equiv) was added via a syringe. The reaction mixture was kept stirring at 70° C. for 12 h. Then, the mixture was cooled down and DMF was removed under reduced pressure. The residue was purified via column chromatography on silica gel using a 1:1 hexane/DCM mixture as the eluent to afford the product 7f' (153 mg, 0.3 mmol) as a white solid at 60% yield. $^1$H NMR (499 MHz, $CDCl_3$) δ 7.32 (s, 1H), 6.97 (s, 1H), 5.65-5.88 (m, 1H), 4.81-5.05 (m, 2H), 3.86 (t, J=7.5 Hz, 2H), 2.00 (q, J=7.0 Hz, 2H), 1.62-1.70 (m, 2H), 1.24-1.39 (m, 6H). $^{13}$C NMR (126 MHz, $CDCl_3$) δ 138.75, 138.24, 136.67, 128.26, 123.76, 122.38, 116.13, 114.81, 114.43, 111.88, 48.23, 33.53, 29.21, 28.63, 28.45, 26.31.

Step 3—Preparation of 2,7-dibromo-5-(8-(1,1,1,3,5,5,5-heptamethyltrisiloxan-3-yl)octyl)-5H-dithieno[3,2-c:2',3'-e][1,2]thiazine 4,4-dioxide (7f)

A 10 ml Schlenk flask was charged with a magnetic stirrer bar and the compound 7f' (256 mg, 0.5 mmol). The flask was evacuated and backfilled with $N_2$ 3 times and 5 ml of dry toluene was added. After dissolving all of the compound 7f', 1,1,1,3,5,5,5-heptamethyltrisiloxane (222.5 mg, 270 μl, 1 mmol, 2 equiv) was added to the mixture, followed by 20 μl of a solution of Karstedt's catalyst in xylene (2% Pt(0)). The resulting mixture was stirred at 85° C. for 24 h. Then, the mixture was cooled down and the solvent was removed under reduced pressure. The residue was purified via column chromatography on silica gel using a 1:1 hexane/DCM mixture as the eluent to afford the product 7f (198 mg, 0.27 mmol) as a colorless oil at 54% yield. $^1$H NMR (499 MHz, $CDCl_3$) δ 7.32 (s, 1H), 6.98 (s, 1H), 3.79-3.90 (m, 2H), 1.61-1.72 (m, 2H), 1.18-1.32 (m, 10H), 0.39-0.47 (m, 2H), 0.08 (s, 18H), 0.01 (s, 3H). $^{13}$C NMR (126 MHz, $CDCl_3$) δ 138.26, 136.66, 128.27, 123.76, 122.39, 116.10, 114.77, 111.84, 48.29, 33.04, 29.30, 29.14, 28.97, 26.53, 23.01, 17.58, 1.87, −0.27.

Example 2

Synthesis of Polymeric Semiconductors

Example 2A

Synthesis of BTSA Bithiophene Copolymers

Various BTSA monomeric units were copolymerized with a bithiophene co-monomer using Stille polymerization reaction according to the general procedure shown in Scheme 4 below. Table 1 shows the resulting polymers.

Scheme 4. Synthesis of N-alkyl BTSA bithiophene copolymers P1-P10

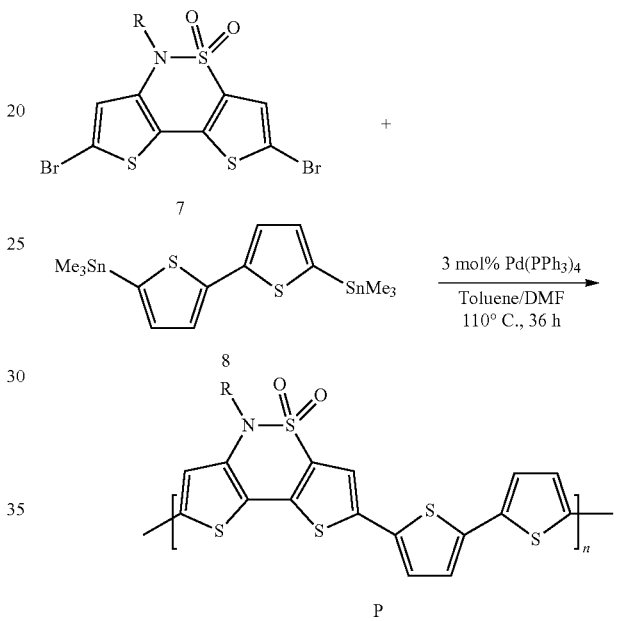

TABLE 1

| Starting Material, 7 | Alkyl Chain, $R^1$ | Product, P |
|---|---|---|
| 7a | $C_{10}H_{21}$ | P1 |
| 7b | $C_{12}H_{25}$, $C_{10}H_{21}$ | P2 |
| 7c | $C_{14}H_{29}$, $C_{14}H_{29}$ | P3 |
| 7d | $C_{16}H_{33}$, $C_{14}H_{29}$ | P4 |
| 7e | $C_8H_{17}$, $C_8H_{17}$ | P5 |

TABLE 1-continued

| Starting Material, 7 | Alkyl Chain, $R^1$ | Product, P |
|---|---|---|
| 7f | –(CH$_2$)$_6$–Si(CH$_3$)(OTMS)$_2$ | P6 |
| 7g | –CH$_2$CH(–)C$_{16}$H$_{33}$ | P7 |
| 7h | –CH$_2$CH(C$_4$H$_9$)(C$_2$H$_5$) | P8 |
| 7i | –CH$_2$CH(C$_8$H$_{17}$)(C$_6$H$_{13}$) | P9 |
| 7j | –CH$_2$CH(C$_{10}$H$_{21}$)(C$_8$H$_{17}$) | P10 |

An air-free flask was charged with the BTSA dibromide monomer 7 (0.15 mmol), 5,5'-bis(trimethylstannyl)-2,2'-bithiophene (8) (73.78 mg, 0.15 mmol), and tetrakis(triphenylphosphine)palladium(0) (5.2 mg, 0.0045 mmol, 3 mol %). The flask was evacuated and backfilled with N$_2$ 3 times, and 5.5 ml of dry toluene and 0.5 ml of dry DMF were added via a syringe. The sealed reaction flask was then placed into an oil bath that has been preheated to 110° C., and stirred at this temperature for 36 h. Then, 50 µL of bromobenzene was added as an end-capping agent, and the reaction mixture was stirred at 110° C. for another 12 h. After cooling to room temperature, the deeply colored mixture was dripped into 100 mL of methanol (containing 5 mL 12 N HCl) with vigorous stirring. After stirring for 2 h, the precipitate was poured into a thimble. After drying, the crude product was subjected to sequential Soxhlet extraction with methanol (2 h), acetone (10 h), hexane (12 h), DCM (3 h), CF (3 h), and CB (3 h). After extraction with the final solvent, the polymer solution was concentrated to approximately 20 mL, which was then poured into 100 mL of methanol with vigorous stirring. The polymer was collected by filtration and dried under reduced pressure to give a deeply colored solid as the product.

Characterization of Polymer P1

P1 ($R^1$=dodecyl): The major soluble fraction of the polymer was extracted using DCM (dichloromethane). After drying, the DCM fraction gave P1 as a purple-blue solid (42 mg) at 49% yield. Mn=3.3 kDa, Mw=5.0 kDa, PDI=1.51. Calculated for C$_{28}$H$_{33}$NO$_2$S$_5$(%): C, 58.60; H, 5.44; N, 2.44. Found (%): C, 58.02; H, 5.55; N, 2.15.

Characterization of Polymer P2

P2 ($R^1$=2-decyltetradecyl): The major soluble fraction of the polymer was extracted using CB (chlorobenzene). After drying, the CB fraction gave P2 as a metallic goldish film (40 mg) at 36% yield. Mn=11.5 kDa, Mw=30.3 kDa, PDI=2.63. Calculated for C$_{40}$H$_{55}$NO$_2$S$_5$(%): C, 64.73; H, 7.47; N, 1.89. Found (%): C, 63.90; H, 7.15; N, 1.99.

Characterization of Polymer P3

P3 ($R^1$=2-tetradecylhexadecyl): The major soluble fraction of the polymer was extracted using CF (chloroform). After drying, the CF fraction gave P3 as a metallic goldish film (109 mg) at 88% yield. Mn=20.3 kDa, Mw=157.3 kDa, PDI=7.5. Calculated for C$_{46}$H$_{67}$NO$_2$S$_5$(%): C, 66.86; H, 8.17; N, 1.69. Found (%): C, 66.76; H, 7.92; N, 1.73.

Characterization of Polymer P4

P4 ($R^1$=2-tetradecyloctadecyl): The major soluble fraction of the polymer was extracted using CB (chlorobenzene). After drying, the CB fraction gave P4 as a metallic goldish film (39 mg) at 30% yield. Mn=183.3 kDa, Mw=381.4 kDa, PDI=2.1. Calculated for C$_{48}$H$_{71}$NO$_2$S$_5$(%): C, 67.48; H, 8.38; N, 1.64. Found (%): C, 67.17; H, 8.04; N, 1.74.

Characterization of Polymer P5

P5 ($R^1$=1-octylnonyl): The major soluble fraction of the polymer was extracted using CB (chlorobenzene). After drying, the CB fraction gave P5 as a metallic goldish film (62 mg) at 64% yield. Mn=6.3 kDa, Mw=10.5 kDa, PDI=1.7. Calculated for C$_{33}$H$_{41}$NO$_2$S$_5$(%): C, 61.54; H, 6.42; N, 2.17. Found (%): C, 59.19; H, 6.17; N, 1.89.

Characterization of Polymer P6

P6 (R=(CH$_2$)$_8$SiCH$_3$(OSi(CH$_3$)$_3$)$_2$): The major soluble fraction of the polymer was extracted using CF (chloroform). After drying, the CF fraction gave P6 as a metallic goldish film (52 mg) at 47% yield. Calculated for C$_{31}$H$_{43}$NO$_4$S$_5$Si$_3$(%): C, 50.43; H, 5.87; N, 1.90. Found (%): C, 50.24; H, 5.91; N, 1.86.

Characterization of Polymer P7

P7 (R=octadecyl): The major soluble fraction of the polymer was extracted using CF (chloroform). After drying, the CF fraction gave P7 as a purple-blue solid (30 mg) at 32% yield. Mn=11.7 kDa, Mw=16.9 kDa, PDI=1.44.

Characterization of Polymer P8

P8 (R=2-ethylhexyl): The major soluble fraction of the polymer was extracted using CB (chlorobenzene). After drying, the CB fraction gave P8 as a purple-blue solid (16 mg) at a 20% yield. Mn=6.5 kDa, Mw=22.6 kDa, PDI=3.45.

Characterization of Polymer P9

P9 (R=2-hexyldecyl): The major soluble fraction of the polymer was extracted using CB (chlorobenzene). After drying, the CB fraction gave P9 as a metallic goldish film (45 mg) at 47% yield. Mn=14.3 kDa, Mw=23.1 kDa, PDI=1.6.

Characterization of Polymer P10

P10 (R=2-octyldodecyl): The major soluble fraction of the polymer was extracted using CB (chlorobenzene). After drying, the CB fraction gave P10 as a metallic goldish film (50 mg) at 49% yield. Mn=14.7 kDa, Mw=26.6 kDa, PDI=1.81.

Example 2B

Synthesis of Other BTSA-Based Copolymers

Additional BTSA-based polymers P11, P12, and P13 were synthesized using Stille polymerization reaction according to the procedure shown in Scheme 5 below.

Scheme 5. Synthesis of N-alkyl BTSA copolymers P11-P13

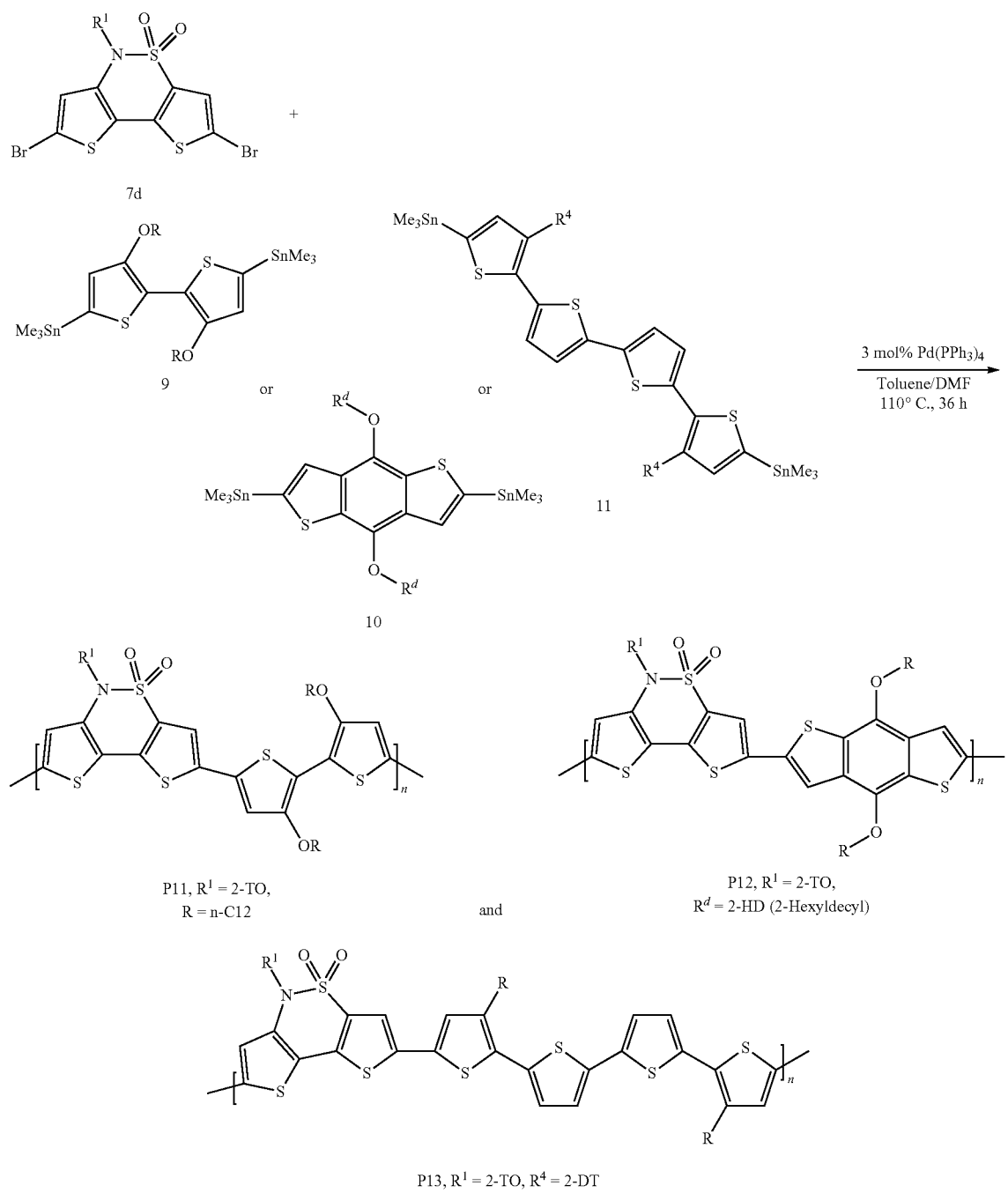

P11, R¹ = 2-TO, R = n-C12 and

P12, R¹ = 2-TO, R$^d$ = 2-HD (2-Hexyldecyl)

P13, R¹ = 2-TO, R⁴ = 2-DT

Synthesis and Characterization of Polymer P11

P11 (R¹=2-tetradecyloctadecyl, R=dodecyl): The polymer was synthesized using dialkoxybithiophene stannane 9. The major soluble fraction of the polymer was extracted using CF (chloroform). After drying, the CF fraction gave P11 as a metallic dark-blue film (161 mg) at 87% yield. Mn=44.4 kDa, Mw=71.3 kDa, PDI=1.6. Calculated for $C_{72}H_{119}NO_4S_5$(%): C, 70.71; H, 9.81; N, 1.15. Found (%): C, 70.62; H, 10.00; N, 1.16.

Synthesis and Characterization of Polymer P12

P12 (R¹=2-tetradecyloctadecyl, R=2-hexyldecyl): The polymer was synthesized using benzodithiophene stannane 10. The major soluble fraction of the polymer was extracted using H (hexane). After drying, the H fraction gave P12 as a red solid (191 mg) at 93% yield. Mn=22.4 kDa, Mw=39.2 kDa, PDI=1.7. Calculated for $C_{82}H_{135}NO_4S_5$(%): C, 72.46; H, 10.01; N, 1.03. Found (%): C, 72.52; H, 9.90; N, 1.13.

Synthesis and Characterization of Polymer P13

P13 ($R^1$=2-tetradecyloctadecyl, R=decyltetradecyl): The polymer was synthesized using tetrathiophene stannane 11. The major soluble fraction of the polymer was extracted using H (hexane). After drying, the H fraction gave P13 as a red solid (90 mg) at 35% yield.

Synthesis and Characterization of Polymer P14

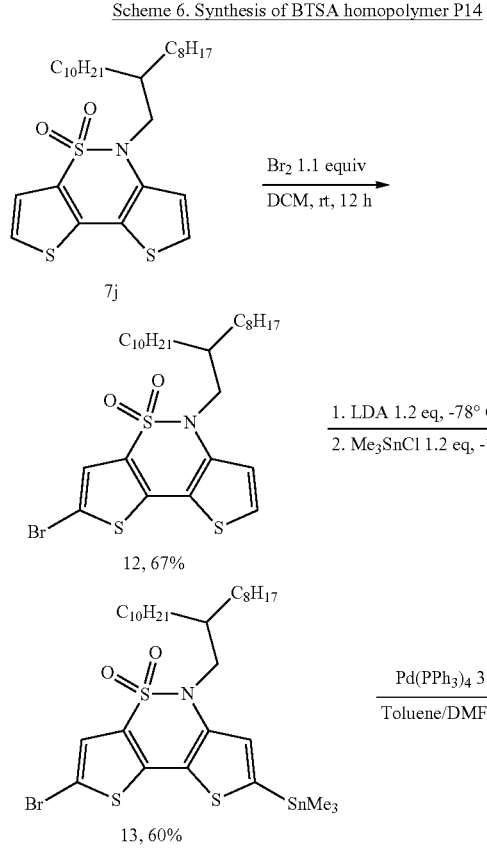

Referring to Scheme 6 above, the polymer P14 was synthesized using standard Stille polymerization procedure using the biheterofunctional monomer 13.

P14: The major soluble fraction of the polymer was extracted using H (hexane). After drying, the H fraction gave P14 as a metallic dark-blue film (60 mg) at 75% yield. Mn=14.5 kDa, Mw=45.3 kDa, PDI=3.1.

Synthesis and Characterization of Polymers P15, P16, and P17

Additional BTSA-based polymers P15, P16, and P17 were synthesized using Stille polymerization reaction according to the procedures shown in Scheme 7 below.

Scheme 7. Synthesis of N-alkyl BTSA copolymers P15-P17

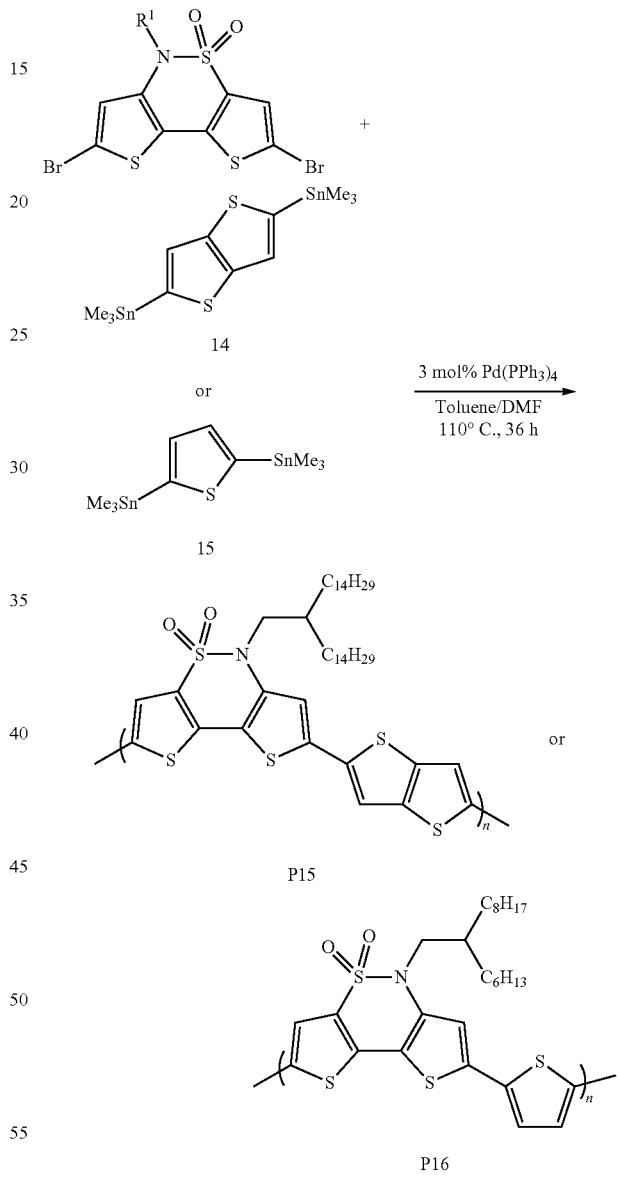

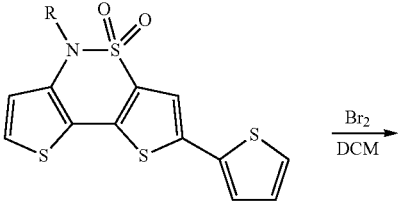

-continued

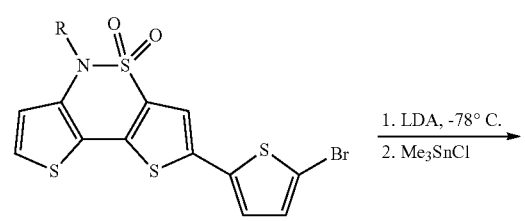

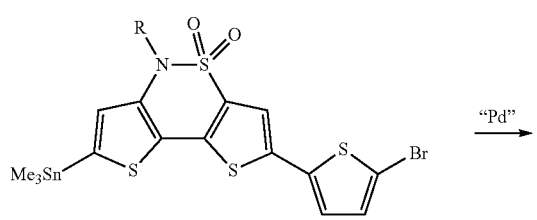

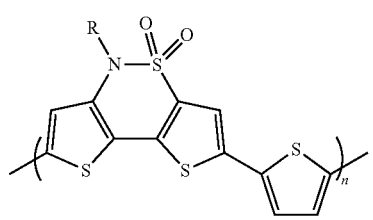

P17, R = 2-HexylDecyl (2-HD)
"Pd" = 3 mol% Pd(PPh$_3$)$_4$
Toluene/DMF, 110° C., 36 h

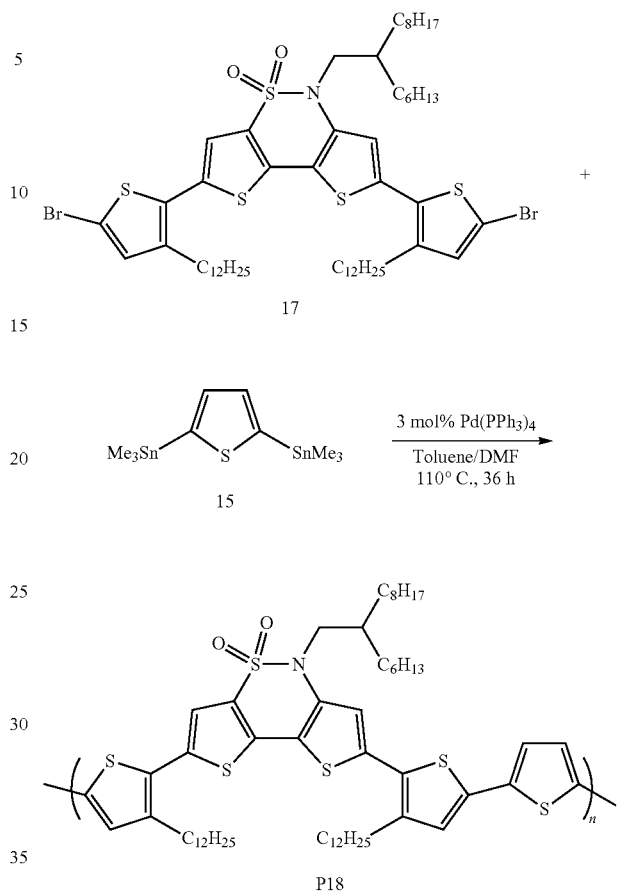

Scheme 8. Synthesis of N-alkyl BTSA trithiophene copolymer P18

P15: Referring to Scheme 7A, polymer P15 was synthesized using thienothiophene stannane 14. The major soluble fraction of the polymer was extracted using chloroform. After drying, the chloroform fraction gave P15 as a metallic dark-blue film (78 mg) at 65% yield. Mn=18.5 kDa, Mw=48.1 kDa, PDI=2.6. Calculated for $C_{44}H_{65}NO_2S_5$(%): C, 66.03; H, 9.19; N, 1.75. Found (%): C, 66.06; H, 8.06; N, 1.72.

P16: With continued reference to Scheme 7A, polymer P16 was synthesized using thiophene stannane 15. The major soluble fraction of the polymer was extracted using chloroform. After drying, the chloroform fraction gave P16 as a metallic dark-brown film (88 mg) at 86% yield. Mn=11.4 kDa, Mw=52.7 kDa, PDI=4.6.

P17: Referring to Scheme 7B, regioregular polymer P17 was synthesized using biheterofunctional monomer 16. The major soluble fraction of the polymer was extracted using CF (chloroform). After drying, the CF fraction gave P17 as a metallic dark-brown film (87 mg) at 87% yield. Mn=14.1 kDa, Mw=47.9 kDa, PDI=3.4.

Synthesis and Characterization of Polymer P18

Referring to Scheme 8 below, polymer P18 was synthesized using standard Stille polymerization procedure.

P18: The polymer was synthesized using dibromo monomer 17 and thiophene stannane 15. The major soluble fraction of the polymer was extracted using chloroform. After drying, the chloroform fraction gave P17 as a dark-brown powder (133 mg) at 79% yield. Mn=52.9 kDa, Mw=391.5 kDa, PDI=7.4.

Example 2C

Optical and Electrochemical Properties of BTSA-Based Polymers

Figure 4A:
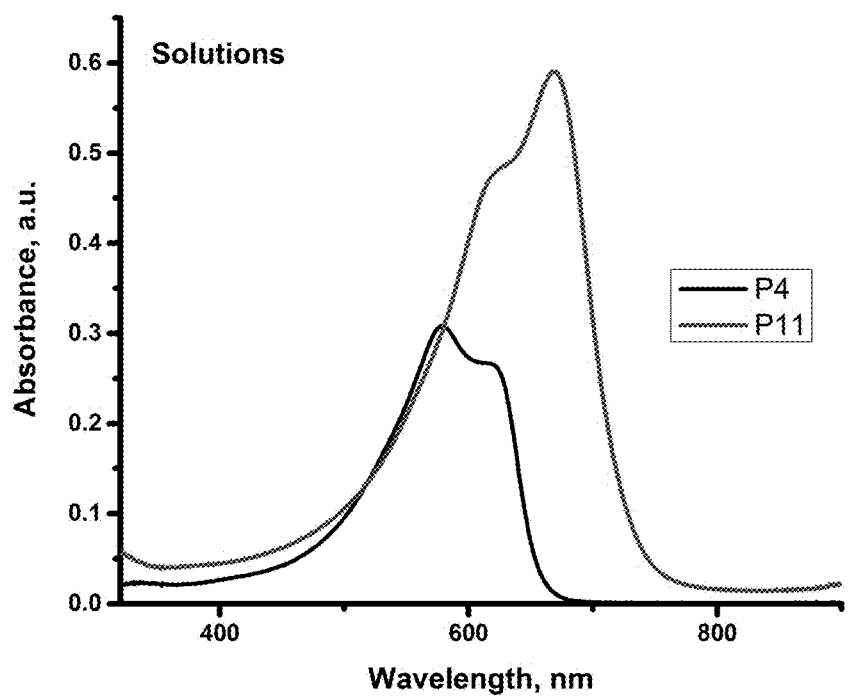
FIGS. 4a-b show optical absorption spectra of two polymers according to the present teachings.
Figure 4B:
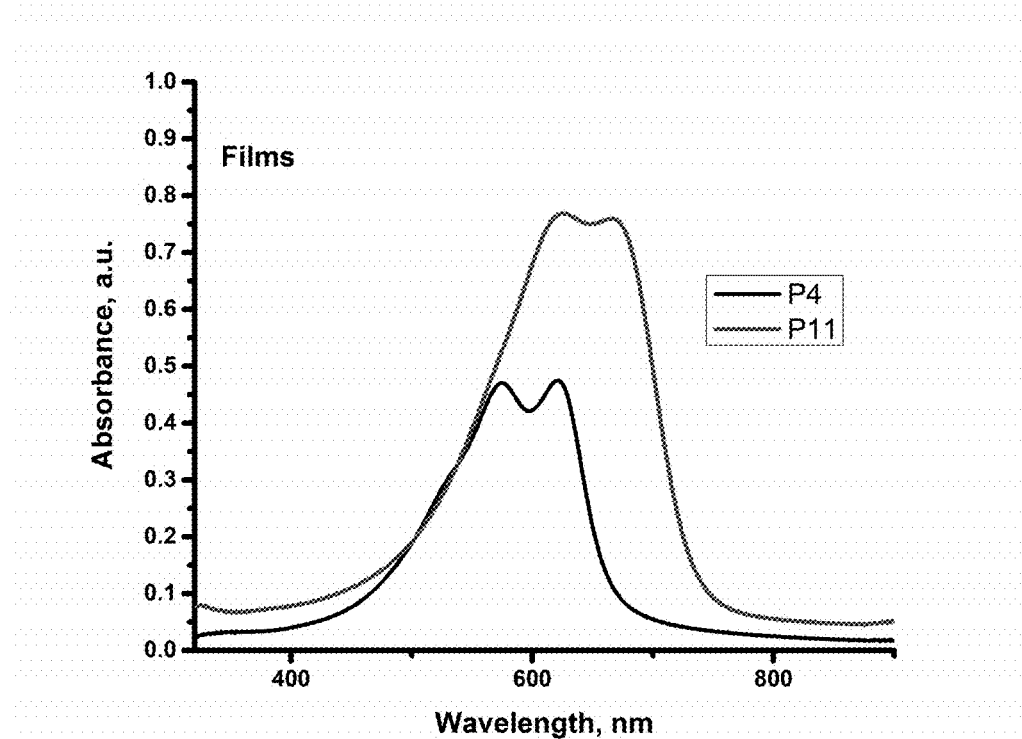
Figure 5:
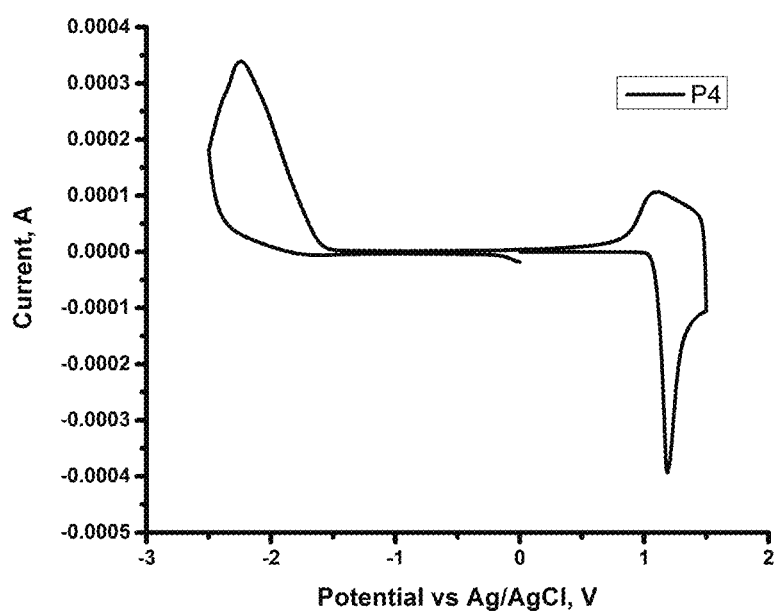
FIG. 5 shows a cyclic voltammogram of polymer P4.
Figure 6A:
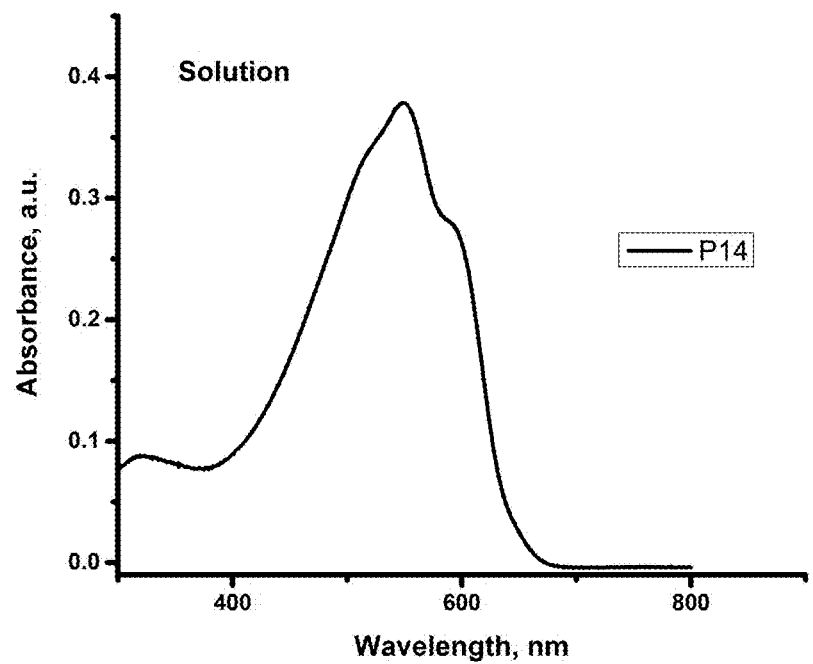
FIGS. 6a-b show a representative optical absorption spectrum and a representative cyclic voltammogram of another polymer according to the present teachings.
Figure 6B:
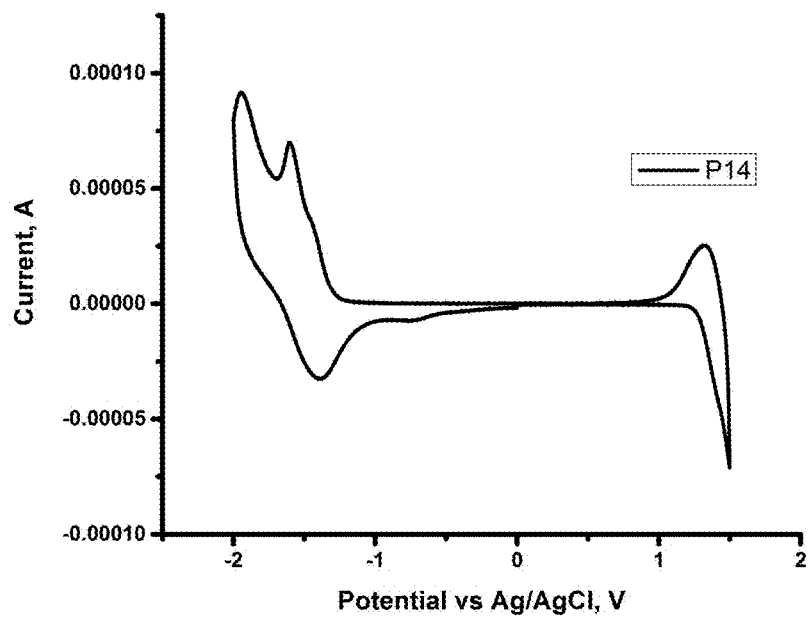

UV/Vis absorption spectra of polymers P1-P18 were collected in solution and as thin films. Representative spectra are depicted in FIGS. 4a, 4b, and 6a. Cyclic voltammetry was used to estimate the HOMO energy. Representative cyclic voltammograms are shown in FIGS. 5 and 6b. The band gap ($E_g$) of polymers P1-P18 was determined as an onset of UV-Vis absorption; $E_{HOMO}$ is determined as an onset of oxidation potential of CV experiment; $E_{LUMO}=E_{HOMO}+E_g$.

TABLE 2
Properties of P1-P18.
| Polymer | $E_g^{Sol}$, eV | $E_g^{Film}$, eV | $E_{HOMO}$, eV | $E_{LUMO}$, eV |
| --- | --- | --- | --- | --- |
| 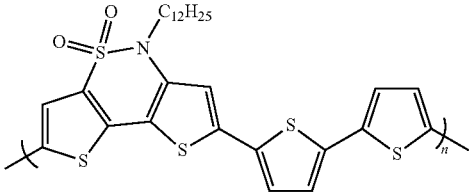<br>P1 | 1.85 | 1.83 | −5.24 | −3.41 |
| 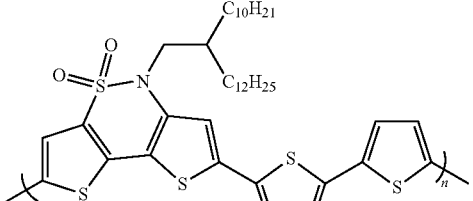<br>P2 | 1.89 | 1.86 | −5.34 | −3.48 |
| 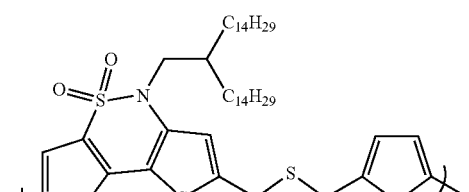<br>P3 | 1.89 | 1.84 | −5.39 | −3.55 |
| 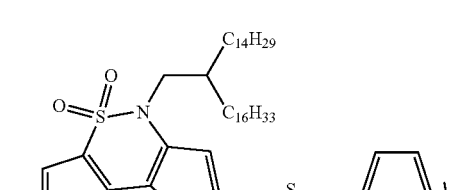<br>P4 | 1.89 | 1.85 | −5.41 | −3.56 |
| 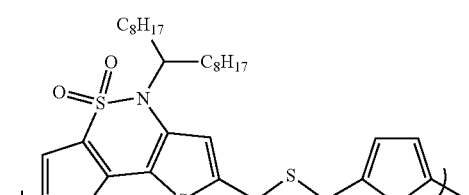<br>P5 | 1.90 | 1.89 | −5.3 | −3.41 |

TABLE 2-continued
Properties of P1-P18.
| Polymer | $E_g^{Sol}$, eV | $E_g^{Film}$, eV | $E_{HOMO}$, eV | $E_{LUMO}$, eV |
|---|---|---|---|---|
| 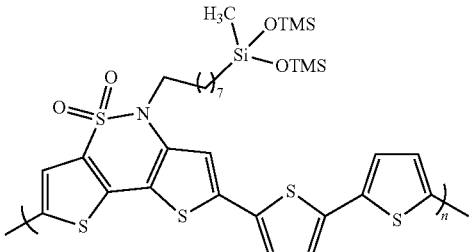 P6 | 1.84 | 1.83 | −5.21 | −3.38 |
| 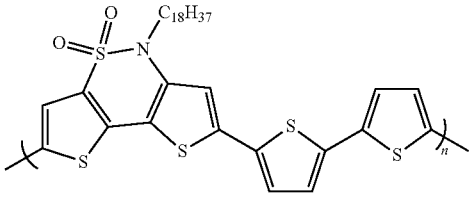 P7 | 1.85 | 1.85 | — | — |
| 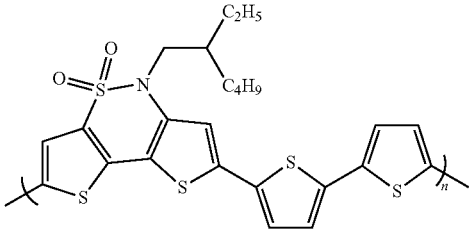 P8 | 1.82 | 1.81 | −5.27 | −3.46 |
| 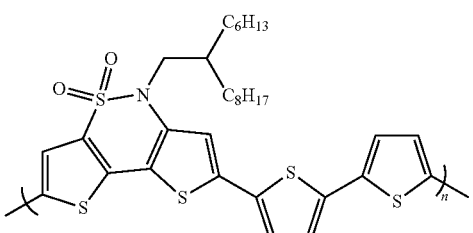 P9 | 1.84 | 1.85 | −5.27 | −3.42 |
| 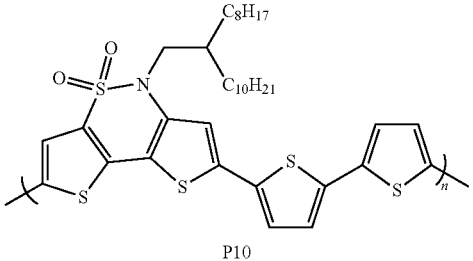 P10 | 1.85 | 1.84 | −5.31 | −3.47 |

TABLE 2-continued
Properties of P1-P18.
| Polymer | $E_g^{Sol}$, eV | $E_g^{Film}$, eV | $E_{HOMO}$, eV | $E_{LUMO}$, eV |
|---|---|---|---|---|
| 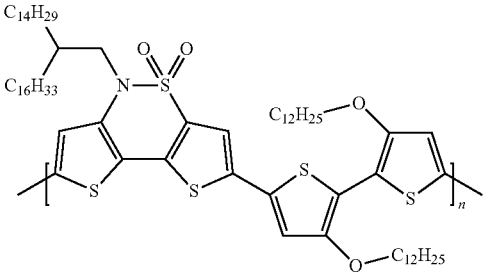  P11 | 1.69 | 1.68 | −5.23 | −3.54 |
| 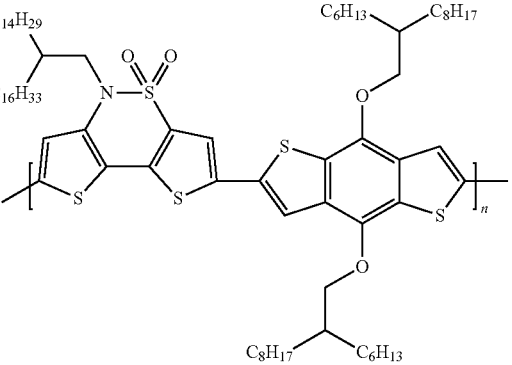  P12 | 2.05 | 2.03 | −5.52 | −3.49 |
| 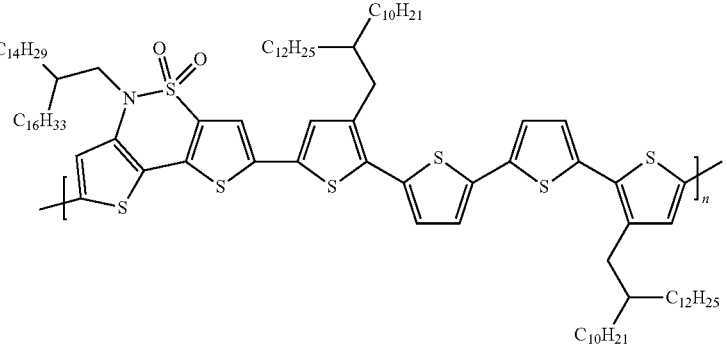  P13 | — | — | — | — |
| 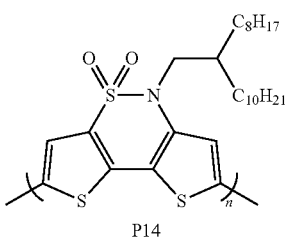  P14 | 1.91 | 1.86 | −5.65 | −3.79 |

TABLE 2-continued

Properties of P1-P18.

| Polymer | $E_g^{Sol}$, eV | $E_g^{Film}$, eV | $E_{HOMO}$, eV | $E_{LUMO}$, eV |
|---|---|---|---|---|
| P15 | 1.89 | 1.85 | −5.47 | −3.62 |
| P16 | 1.90 | 1.85 | −5.40 | −3.55 |
| P17, regular | 1.88 | 1.87 | −5.49 | −3.62 |
| P14 | 1.93 | 1.86 | −5.36 | −3.50 |

Example 3

Synthesis of Molecular Semiconductors

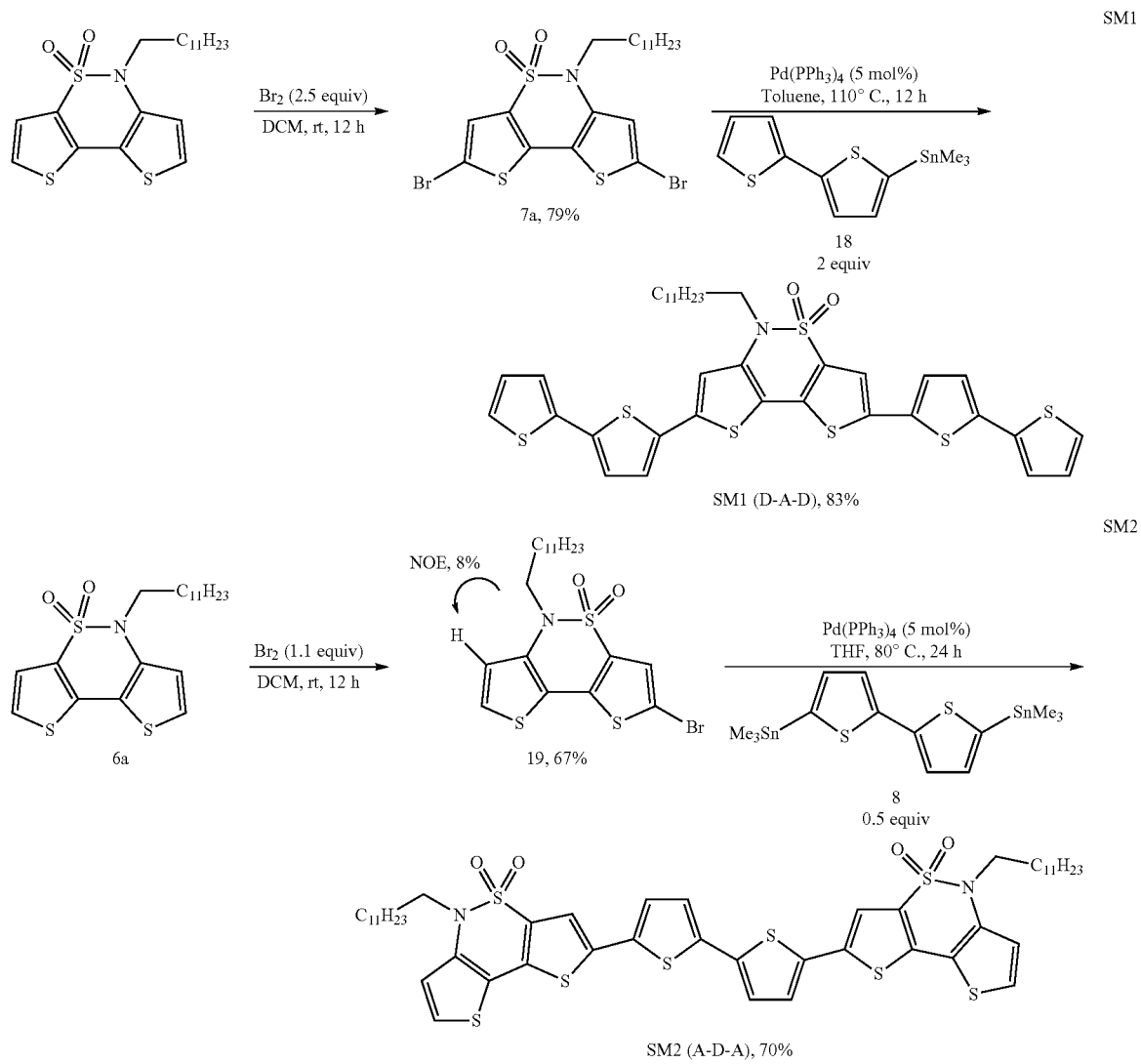

Scheme 9. Synthesis of BTSA-containing molecular semiconductgors SM1 and SM2

SM1: The small molecule SM1 was synthesized using standard Stille procedure (general procedure for polymerization) but using dibromomonomer 7a and monostannane 18. After the reaction was complete, the material was precipitated in MeOH, filtered, and then washed with MeOH (3×50 ml). The resulting orange solid was purified via column chromatography on silica gel using a 1:5 hexane/DCM mixture as the eluent to afford the product SM1 as a bright orange solid at 83% yield. $^1$H NMR (499 MHz, CDCl$_3$) δ 7.38 (s, 1H), 7.24-7.28 (m, 2H), 7.20 (ddd, J=5.1, 3.6, 1.1 Hz, 2H), 7.15 (d, J=3.8 Hz, 1H), 7.06-7.12 (m, 3H), 7.04 (ddd, J=5.1, 3.5, 1.6 Hz, 2H), 6.97 (s, 1H), 3.95 (t, J=7.5 Hz, 2H), 1.75 (m, 2H), 1.17-1.37 (m, 18H), 0.86 (t, J=7.0 Hz, 3H). $^{13}$C NMR (126 MHz, CDCl$_3$) δ 139.21, 138.21, 137.99, 137.23, 136.49, 136.48, 135.83, 134.38, 134.37, 133.82, 128.69, 128.03, 128.00, 125.79, 125.59, 125.19, 125.09, 124.51, 124.43, 124.28, 124.26, 116.89, 114.80, 113.77, 47.89, 31.90, 29.65, 29.63, 29.52, 29.46, 29.35, 29.26, 29.05, 26.54, 22.68, 14.11.

SM2: The small molecule SM2 was synthesized using modified Stille polymerization procedure (THF, 85° C., 24 h) using monobromomonomer 19 and 5,5'-bis(trimethylstannyl)-2,2'-bithiophene 8. After the reaction was complete, the material was precipitated in MeOH, filtered, then washed with MeOH (3×50 ml). The resulting orange solid was purified via column chromatography on silica gel using a 1:5 hexane/DCM mixture as the eluent to afford the product SM2 as a bright orange solid at 70% yield. $^1$H NMR (499 MHz, CDCl$_3$) 7.34-7.42 (m, 4H), 7.14 (q, J=3.9 Hz, 4H), 7.00 (d, J=5.4 Hz, 2H), 3.94 (t, J=7.6 Hz, 4H), 1.71 (m, 4H), 1.15-1.36 (m, 36H), 0.87 (t, J=6.9 Hz, 6H). $^{13}$C NMR (126 MHz, CDCl$_3$) δ 139.04, 136.90, 135.57, 135.08, 134.57, 128.73, 125.96, 125.71, 124.96, 119.50, 117.16, 115.40, 48.00, 31.87, 29.57, 29.45, 29.40, 29.31, 29.23, 29.03, 26.52, 22.65, 14.08. Some signals may overlap.

Example 4

Fabrication and Characterization of OPV Devices

Conventional OPV devices were fabricated by evaporating 8 nm of $MoO_3$ onto pre-cleaned ITO substrates. The donor polymer P3 and molecular acceptor $C_{70}PCBM$ were dissolved in a $CHCl_3$:DCB solvent mixture (9:1 by volume). Diiodooctane (2% by volume) was added to the solution before spin casting the active layers. Finally, 0.6 nm of LiF and 100 nm of Al were evaporated as the top electrode. Devices were encapsulated using a blanket of EPOTEK OG116-31 UV-curable epoxy (Epoxy Technologies) and a cover slip.

The photovoltaic characteristics of the devices were tested in air. The current-voltage (I-V) curves were obtained by a Keithley 2400 source-measure unit. The photocurrent was measured under simulated AM1.5G irradiation (100 mW $cm^{-2}$) using a xenon-lamp-based solar simulator (Newport 91160A 300W Class-A Solar Simulator, 2 inch by 2 inch uniform beam). The light intensity was set using a NREL calibrated silicon photodiode with a color filter. External quantum efficiency was measured using Newport's QE setup. Incident light from a xenon lamp (300 W) passing through a monochromator (Newport, Cornerstone 260) was focused on the active area of the cell. The output current was measured using a current pre-amplifier (Newport, 70710QE) and a lock-in amplifier (Newport, 70105 Dual channel Merlin). A calibrated silicon diode (Newport 70356) was used as a reference.

Figure 7A:
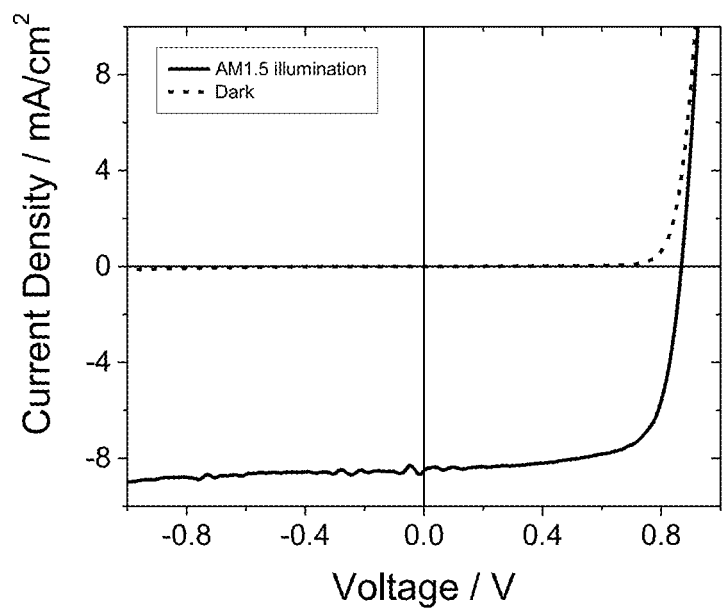
FIGS. 7a-b show the performance of a representative bulk-heterojunction OPV device having a blend material as the active layer, where the blend material includes a polymer (P3) according to the present teachings as the donor and $C_{70}PCBM$ as the acceptor.
Figure 7B:
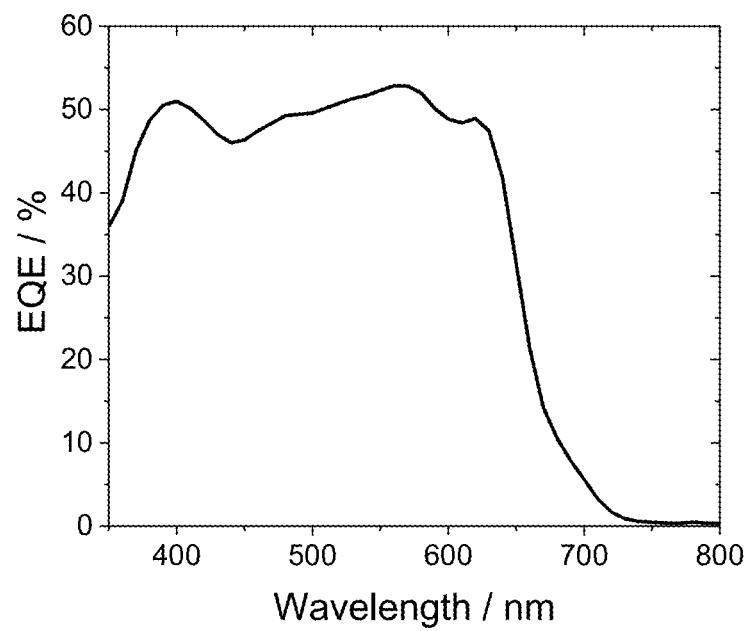
Figure 8:
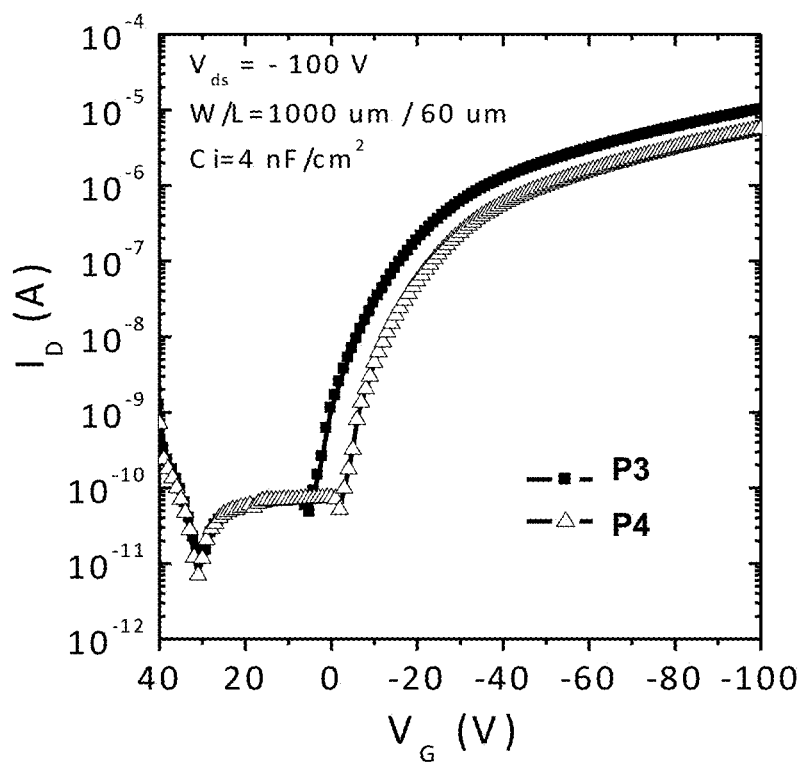
FIG. 8 shows the transfer plots of representative top-gate bottom-contact OTFT devices having the polymer P3 and P4, respectively, as the semiconductor component. Mobilities of ~0.028-0.051 $cm^2/Vs$, on-off current ratio of ~$10^5$, and turn-on voltage ranging from −2 V to +5V were obtained.
Figure 9:
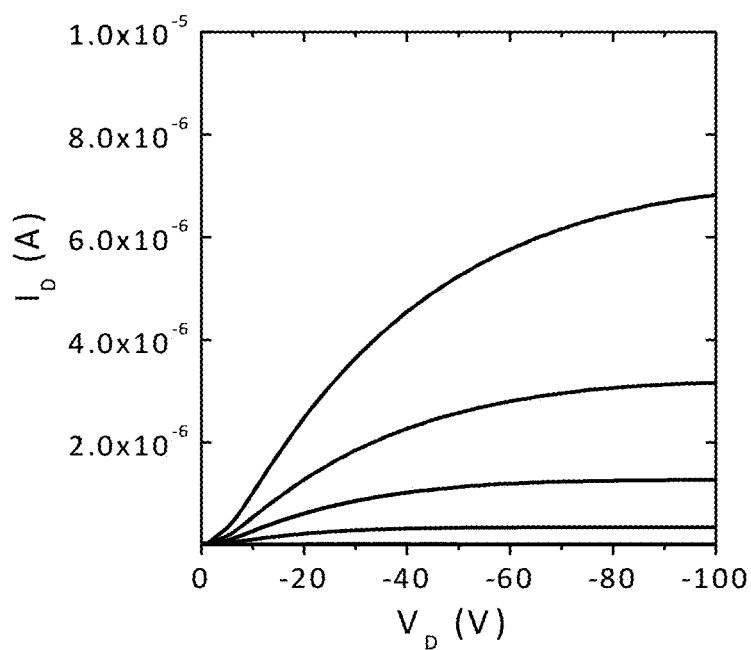
FIG. 9 shows the output plot of a representative top-gate bottom-contact OTFT device having the polymer P3 as the semiconductor component with gate voltage varying step-wise from 0V to −100V at −20V per step.

The JV characteristics for a typical device are summarized in Table 3. The JV scan and EQE curve are shown in FIGS. 7a-b.

TABLE 3

JV characteristics of a $P3:C_{70}PCBM$ blend device measured under simulated AM1.5 (100 $mW/cm^2$).

| $V_{oc}$ [V] | $J_{sc}$ [$mA/cm^2$] | FF [%] | PCE [%] |
|---|---|---|---|
| 0.87 | 8.4 | 71.2 | 5.2 |

Example 5

Fabrication and Characterization of OFET Devices

Example 5a

Top-Gate Bottom-Contact OFETs

Top-gate bottom-contact OFET devices were fabricated with polymers according to the present teachings. Corning Eagle 2000 glasses were used as substrates. Source/drain electrodes were defined by thermal evaporation of a 50 nm thick gold film through shadow masks. The channel lengths and widths are 60 μm and 1000 μm, respectively. The active semiconductor layer (50 nm~100 nm) comprises semiconductor compound dissolved in chloroform or 1,2-dichlorobenzene and was formed by spin-coating then annealing on a 120° C. hot plate for 10 min (unless otherwise specified) to remove the solvent residues. A poly(methyl methacrylate) (PMMA) film was formed on the semiconductor layer as the gate dielectric. The deposition processes of the semiconducting layer and dielectric layer were performed inside of a nitrogen-filled glove box unless specified. The devices were completed by thermally evaporating a 50 nm thick gold film as the gate electrode. The resulting capacitance of such polymer gate dielectric is about 4 $nF/cm^2$. Table 4 summarizes the performance (hole mobility $\mu_h$, current on/off ratio $I_{ON}/I_{OFF}$, and turn on voltage $V_{on}$) of representative TGBC OTFT devices.

TABLE 4

Device performance of TGBC OTFT devices.

| Semiconductor | $\mu_h$ ($cm^2/Vs$) | $I_{ON}/I_{OFF}$ | $V_{on}$ (V) |
|---|---|---|---|
| P1 | 1.7E-3~2.0E-3 | ~$10^4$ | ~-8 |
| P2 | 1.6E-3~2.5E-3 | ~$10^5$ | ~-3 |
| P3 | 2.8E-2~5.1E-2 | ~$10^5$ | ~+5 |
| P4 | 2.8E-2~3.9E-2 | ~$10^4$ | ~-2 |
| P5 | 2.6E-4~4.4E-4 | ~$10^4$ | ~-5 |
| P6 | 8.4E-5~1.2E-4 | ~$10^2$ | ~-24 |
| P7 | 2.3E-4~2.5E-4 | ~$10^3$ | ~-15 |
| P8 | 1.5E-4~2.2E-4 | ~$10^3$ | ~-7 |
| P9 | 5.1E-4~5.9E-4 | ~$10^3$ | ~-14 |
| P10 | 5.4E-4~6.5E-4 | ~$10^3$ | ~-18 |

Example 5b

Bottom-Gate Top-Contact OFETs

Bottom-gate top-contact OFET devices were fabricated with polymers according to the present teachings. Unpatterned 700 μm-thick heavily doped n-type silicon wafers (resistivity 0.005~0.02 Ω·m) coated with a 300+/−5% nm thermal oxide film were used as the gate electrode and gate dielectric, respectively. The silicon oxide substrates were immersed for an hour in a hexane solution of octadecyltrichlorosilane (OTS, 3 mM) at ~50% relative humidity in air, followed by sonication in hexane, acetone, and isopropanol sequentially. The resulting water contact angle was around 109°. The active semiconductor layer (50 nm~100 nm) comprises semiconductor compound dissolved in chloroform and was formed by spin-coating then annealing on a 120° C. hot plate for 10 min (unless otherwise specified) to remove solvent residues. Source/drain electrodes were defined by thermal evaporation of a 50 nm thick gold film through shadow masks.

The deposition process of the semiconducting layer was performed inside of a nitrogen-filled glove box unless specified. The channel lengths and widths are 100 μm and 1000 μm, respectively. The resulting capacitance of the silicon oxide dielectric with OTS treatment is about 10.5 $nF/cm^2$. Table 5 summarizes the performance (hole mobility $\mu_h$, current on/off ratio $I_{ON}/I_{OFF}$, and turn on voltage $V_{on}$) of representative BGTC OTFT devices.

Figure 10:
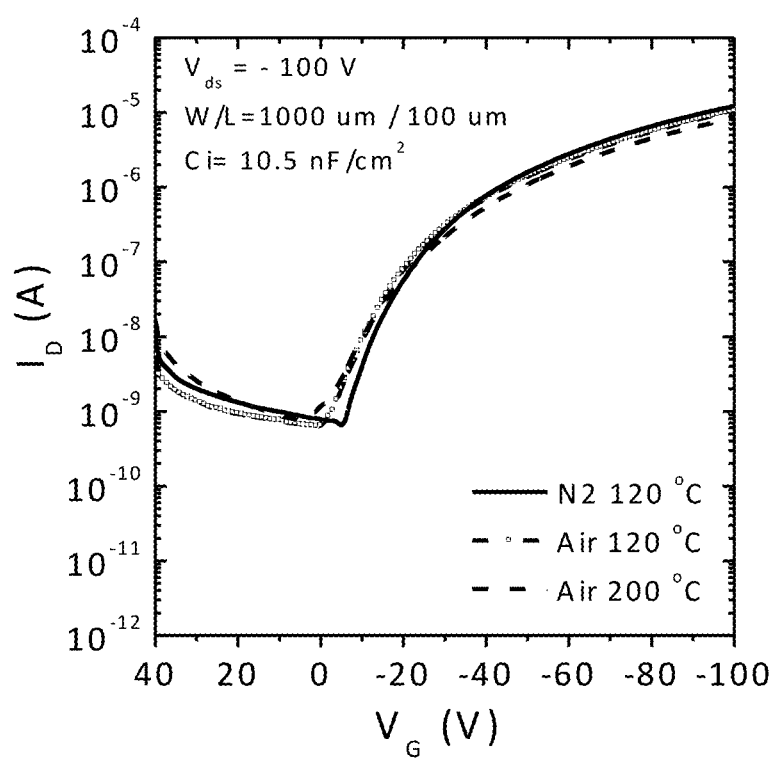
FIG. 10 shows the transfer plots of representative BGTC OTFT devices having the polymer P4 as the semiconductor component, where the semiconductor component was processed in $N_2$ at 120° C., in air at 120° C., and in air at 200° C., respectively.

FIG. 10 compares the transfer plots of BGTC OTFT devices having the polymer P4 as the semiconductor component that were deposited and annealed at 120° C. for 10 minutes in nitrogen, deposited and annealed at 120° C. and 200° C. for 30 minutes in ambient, respectively. The respective average mobilities were 0.042 $cm^2/Vs$, 0.039 $cm^2/Vs$, and 0.036 $cm^2/Vs$, demonstrating the air stability of the polymeric semiconductor.

TABLE 5

Device performance of BGTC OTFT devices.

| Semiconductor | $\mu_h$ ($cm^2/Vs$) | $I_{ON}/I_{OFF}$ | $V_{on}$ (V) |
|---|---|---|---|
| P2 | 6.9E-3~2.2E-2 | ~$10^4$ | ~-14 |
| P3 | 3.4E-3~5.7E-2 | ~$10^5$ | ~3 |

TABLE 5-continued

Device performance of BGTC OTFT devices.

| Semiconductor | $\mu_h$ (cm$^2$/Vs) | $I_{ON}/I_{OFF}$ | $V_{on}$ (V) |
|---|---|---|---|
| P4 | 4.3E−3~5.3E−2 | ~10$^5$ | ~−6 |
| P6 | 3.0E−4~8.2E−4 | ~10$^3$ | ~−27 |

All publications, including but not limited to patents and patent applications, cited in this specification are herein incorporated by reference as if each individual publication were specifically and individually indicated to be incorporated by reference herein as though fully set forth.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A semiconducting compound comprising one or more optionally substituted bithiophene sulfonamide moieties, wherein the one or more optionally substituted bithiophene sulfonamide moieties are identical or different, each being represented by formula (I):

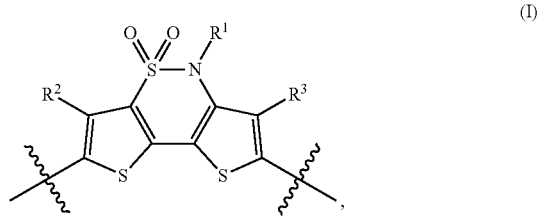

wherein:
R$^1$ is selected from the group consisting of H, a C$_{1-40}$ alkyl group, a C$_{2-40}$ alkenyl group, a C$_{2-40}$ alkynyl group, and a C$_{1-40}$ haloalkyl group, each of which optionally is substituted with 1-10 substituents independently selected from a halogen, —CN, NO$_2$, OH, —NH$_2$, —NH(C$_{1-40}$ alkyl), N(C$_{1-40}$ alkyl)$_2$, —S(O)$_2$OH, —CHO, —C(O)—C$_{1-40}$ alkyl, —C(O)OH, —C(O)—OC$_{1-40}$ alkyl, —C(O)NH$_2$, —C(O)NH—C$_{1-40}$ alkyl, —C(O)N(C$_{1-40}$ alkyl)$_2$, —OC$_{1-40}$ alkyl, —SiH$_3$, —SiH(C$_{1-40}$ alkyl)$_2$, —SiH$_2$(C$_{1-40}$ alkyl), —Si(C$_{1-40}$ alkyl)$_3$, —Si(C$_{1-40}$ alkyl)$_2$(—O—Si(C$_{1-40}$ alkyl)$_3$), —Si(C$_{1-40}$ alkyl)(—O—Si(C$_{1-40}$ alkyl)$_3$)$_2$, —Si(—O—Si(C$_{1-40}$ alkyl)$_3$)$_3$, —O—SiH$_3$, —O—SiH(C$_{1-40}$ alkyl)$_2$, —O—SiH$_2$(C$_{1-40}$ alkyl), —O—Si(C$_{1-40}$ alkyl)$_3$, —O—Si(C$_{1-40}$ alkyl)$_2$(—O—Si(C$_{1-40}$ alkyl)$_3$), and —O—Si(C$_{1-40}$ alkyl)(—O—Si(C$_{1-40}$ alkyl)$_3$)$_2$; and R$^2$ and R$^3$ independently are selected from the group consisting of H, F, Cl, —CN, a C$_{1-40}$ alkyl group, a C$_{2-40}$ alkenyl group, a C$_{2-40}$ alkynyl group, a C$_{1-40}$ haloalkyl group, a C$_{1-40}$ alkoxy group, and a C$_{1-40}$ thioalkyl group, wherein each of the C$_{1-40}$ alkyl group, the C$_{2-40}$ alkenyl group, the C$_{2-40}$ alkynyl group, the C$_{1-40}$ haloalkyl group, the C$_{1-40}$ alkoxy group, and the C$_{1-40}$ thioalkyl group optionally is substituted with 1-5 substituents independently selected from a halogen, —CN, NO$_2$, OH, —NH$_2$, —NH(C$_{1-6}$ alkyl), —N(C$_{1-6}$ alkyl)$_2$, —S(O)$_2$OH, —CHO, —C(O)—C$_{1-6}$ alkyl, —C(O)OH, —C(O)—OC$_{1-6}$ alkyl, —C(O)NH$_2$, —C(O)NH—C$_{1-6}$ alkyl, —C(O)N(C$_{1-6}$ alkyl)$_2$, —OC$_{1-6}$ alkyl, —SiH$_3$, —SiH(C$_{1-40}$ alkyl)$_2$, —SiH$_2$(C$_{1-40}$ alkyl), —Si(C$_{1-40}$ alkyl)$_3$, —Si(C$_{1-40}$ alkyl)$_2$(—O—Si(C$_{1-40}$ alkyl)$_3$), —Si(C$_{1-40}$ alkyl)(-O—Si(C$_{1-40}$ alkyl)$_3$)$_2$, —Si(—O—Si(C$_{1-40}$ alkyl)$_3$)$_3$, —O—SiH$_3$, alkyl)$_2$, —O—SiH$_2$(C$_{1-40}$ alkyl), —O—Si(C$_{1-40}$ alkyl)$_3$ alkyl)$_3$), and —O—Si(C$_{1-40}$ alkyl)(-O—Si (C$_{1-40}$ alkyl)$_3$)$_2$.

2. The compound of claim 1, wherein R$^1$ is selected from the group consisting of:
a) a linear C$_{6-40}$ alkyl, alkenyl, alkynyl or halolalkyl group optionally substituted with 1-10 substituents independently selected from a halogen, —CN, NO$_2$, OH, —NH$_2$, —NH(C$_{1-40}$ alkyl), —N(C$_{1-40}$ alkyl)$_2$, —S(O)$_2$OH, —CHO, —C(O)—C$_{1-40}$ alkyl, —C(O)OH, —C(O)—OC$_{1-40}$ alkyl, —C(O)NH$_2$, —C(O)NH—C$_{1-40}$ alkyl, —C(O)N(C$_{1-40}$ alkyl)$_2$, —OC$_{1-40}$ alkyl, —SiH$_3$, —SiH(C$_{1-40}$ alkyl)$_2$, —SiH$_2$(C$_{1-40}$ alkyl), —Si(C$_{1-40}$ alkyl)$_3$, —Si(C$_{1-40}$ alkyl)$_2$(—O—Si(C$_{1-40}$ alkyl)$_3$), —Si(C$_{1-40}$ alkyl)(-O—Si(C$_{1-40}$ alkyl)$_3$)$_2$, —Si(—O—Si(C$_{1-40}$ alkyl)$_3$)$_3$, —O—SiH$_3$, —O—SiH(C$_{1-40}$ alkyl)$_2$, —O—SiH$_2$(C$_{1-40}$ alkyl), —O—Si(C$_{1-40}$ alkyl)$_3$, —O—Si(C$_{1-40}$ alkyl)$_2$(—O—Si(C$_{1-40}$ alkyl)$_3$), and —O—Si(C$_{1-40}$ alkyl)(-O—Si(C$_{1-40}$ alkyl)$_3$)$_2$;

b) a branched C$_{6-40}$ alkyl, alkenyl, alkynl or halolalkyl group having the formula —CHR'$_2$, where each R' independently is a C$_{1-20}$ alkyl group, a C$_{1-20}$ haloalkyl group, a C$_{2-20}$ alkenyl group, or a C$_{2-20}$ alkynyl group, each of which optionally is substituted with 1-10 substituents independently selected from a halogen, —CN, NO$_2$, OH, —NH$_2$, —NH(C$_{1-40}$ alkyl), —N(C$_{1-40}$ alkyl)$_2$, —S(O)$_2$OH, —CHO, —C(O)—C$_{1-40}$ alkyl, —C(O)OH, —C(O)—OC$_{1-40}$ alkyl, —C(O)NH$_2$, —C(O)NH—C$_{1-40}$ alkyl, —C(O)N(C$_{1-40}$ alkyl)$_2$, —OC$_{1-40}$ alkyl, —SiH$_3$, —SiH(C$_{1-40}$ alkyl)$_2$, —SiH$_2$(C$_{1-40}$ alkyl), —Si(C$_{1-40}$ alkyl)$_3$, —Si(C$_{1-40}$ alkyl)$_2$(—O—Si(C$_{1-40}$ alkyl)$_3$), —Si(C$_{1-40}$ alkyl)(-O—Si(C$_{1-40}$ alkyl)$_3$)$_2$, —Si(—O—Si(C$_{1-40}$ alkyl)$_3$)$_3$, —O—SiH$_3$, —O—SiH(C$_{1-40}$ alkyl)$_2$, —O—SiH$_2$(C$_{1-40}$ alkyl), —O—Si(C$_{1-40}$ alkyl)$_3$, —O—Si(C$_{1-40}$ alkyl)$_2$(—O—Si(C$_{1-40}$ alkyl)$_3$), and —O—Si(C$_{1-40}$ alkyl)(-O—Si(C$_{1-40}$ alkyl)$_3$)$_2$; and c) a branched C$_{6-40}$ alkyl, alkenyl, alkynl or halolalkyl group having the formula —CH$_2$—CHR'$_2$, where each R' independently is a C$_{1-20}$ alkyl group, a C$_{1-20}$ haloalkyl group, a C$_{2-20}$ alkenyl group, or a C$_{2-20}$ alkynyl group, each of which optionally is substituted with 1-10 substituents independently selected from a halogen, —CN, NO$_2$, OH, —NH$_2$, —NH(C$_{1-40}$ alkyl), —N(C$_{1-40}$ alkyl)$_2$, —S(O)$_2$OH, —CHO, —C(O)—C$_{1-40}$ alkyl, —C(O)OH, —C(O)—OC$_{1-40}$ alkyl, —C(O)NH$_2$, —C(O)NH—C$_{1-40}$ alkyl, —C(O)N(C$_{1-40}$ alkyl)$_2$, —OC$_{1-40}$ alkyl, —SiH$_3$, —SiH(C$_{1-40}$ alkyl)$_2$, —SiH$_2$(C$_{1-40}$ alkyl), —Si(C$_{1-40}$ alkyl)$_3$, —Si(C$_{1-40}$ alkyl)$_2$(—O—Si(C$_{1-40}$ alkyl)$_3$), —Si(C$_{1-40}$ alkyl)(-O—Si(C$_{1-40}$ alkyl)$_3$)$_2$, —Si(—O—Si(C$_{1-40}$ alkyl)$_3$)$_3$, —O—SiH$_3$, —O—SiH(C$_{1-40}$ alkyl)$_2$, —O—SiH$_2$ (C$_{1-40}$ alkyl), —O—Si(C$_{1-40}$ alkyl)$_3$, —O—Si(C$_{1-40}$ alkyl)$_2$(—O—Si(C$_{1-40}$ alkyl)$_3$), and —O—Si(C$_{1-40}$ alkyl)(-O—Si(C$_{1-40}$ alkyl)$_3$)$_2$.

3. The compound of claim 2, wherein R$^2$ and R$^3$ are H.

4. The compound of claim 1, wherein the compound is a polymer having a first repeating unit M$_1$ comprising one or more optionally substituted bithiophene sulfonamide moieties represented by formula (I) and wherein said polymer has a degree of polymerization (n) ranging from 3 to 1,000.
5. The compound of claim 4, wherein $M_1$ has a formula selected from the group consisting of:
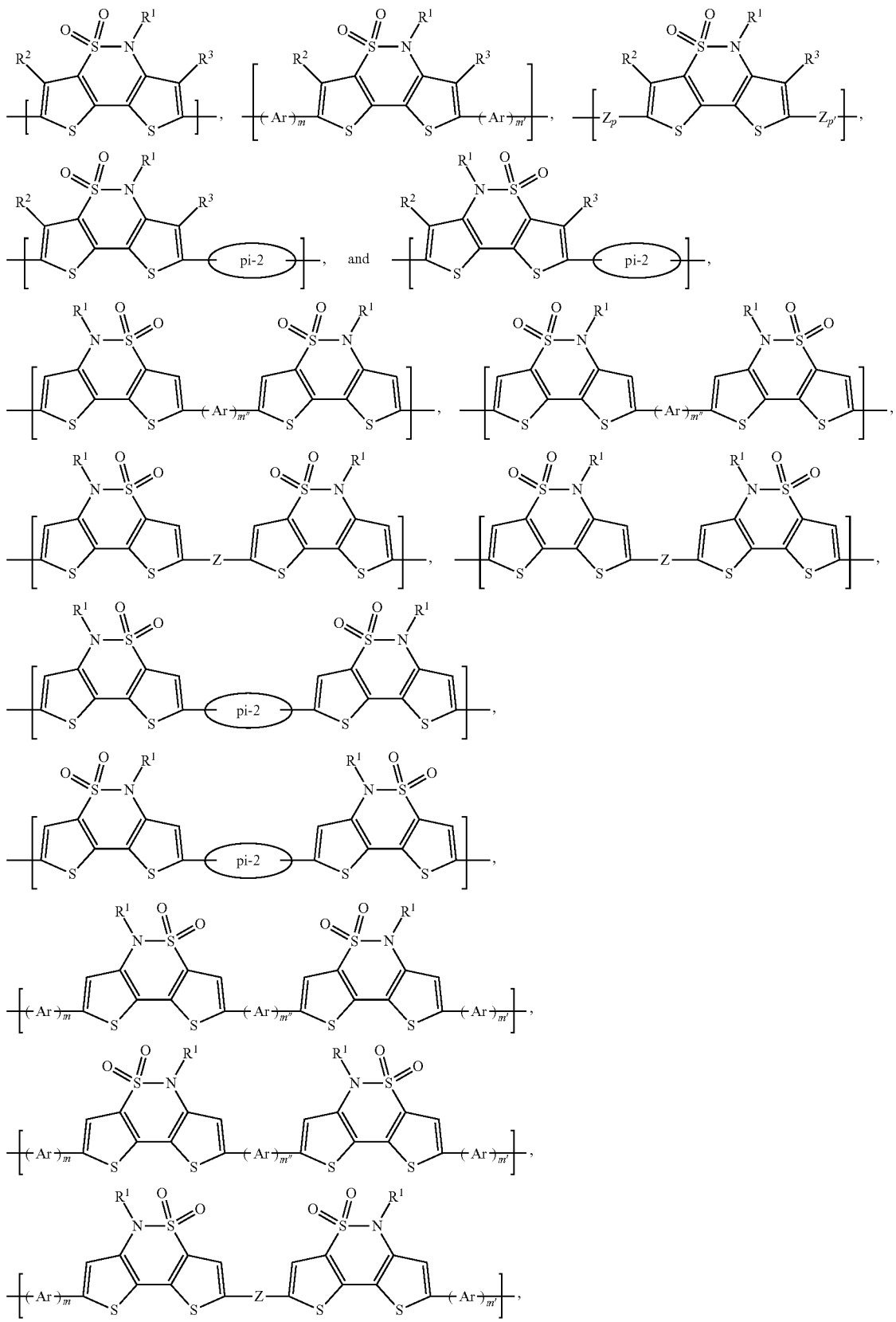

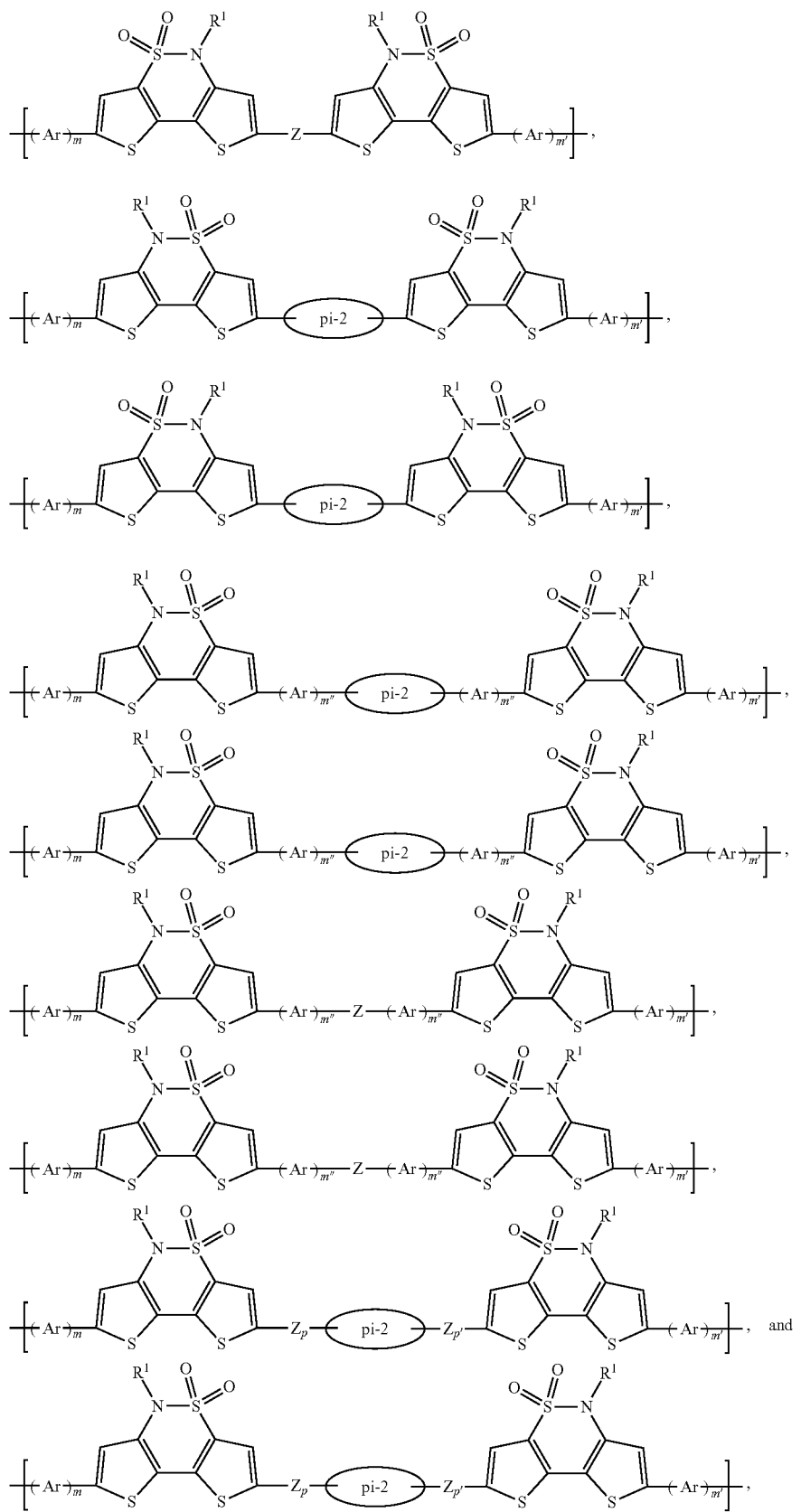

wherein:

pi-2 is an optionally substituted conjugated polycyclic moiety other than an optionally substituted bithiophene sulfonamide moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0;

m" is 1, 2, 3, 4, 5 or 6; and p and p' independently are 0 and 1, provided that at least one of p and p' is 1.

6. The compound of claim 5, wherein pi-2 is an optionally substituted $C_{8-26}$ aryl group or 8-26 membered heteroaryl group.

7. The compound of claim 6, wherein pi-2 is selected from the group consisting of:

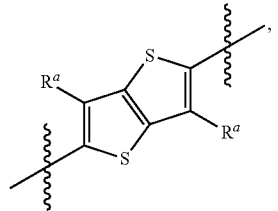,

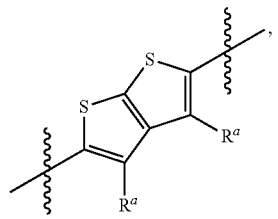,

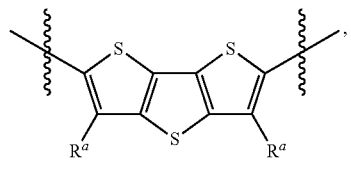,

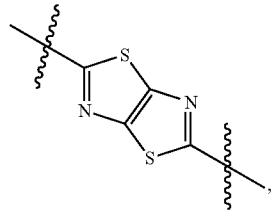,

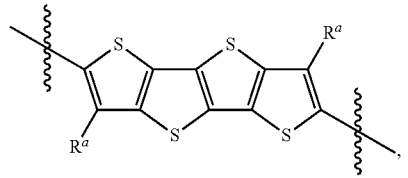,

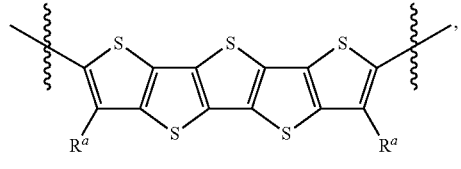,

-continued

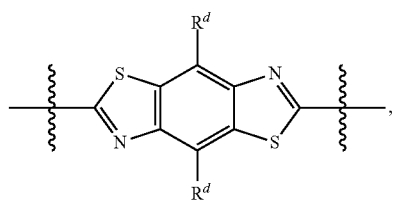,

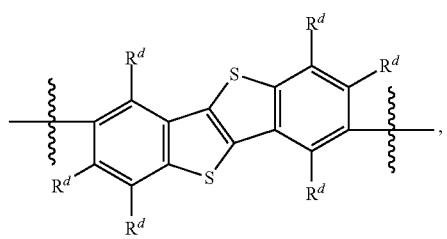,

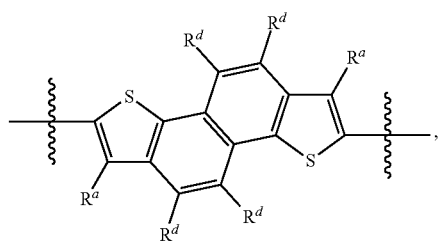,

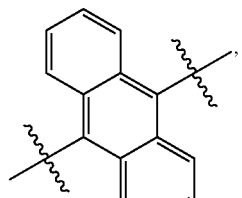,

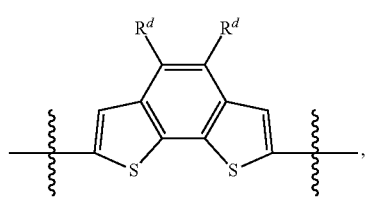,

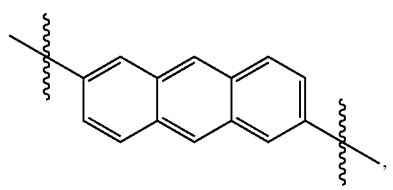,

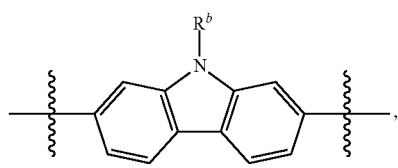,

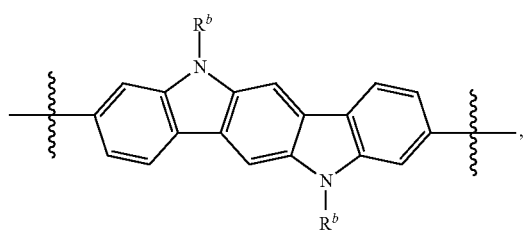,

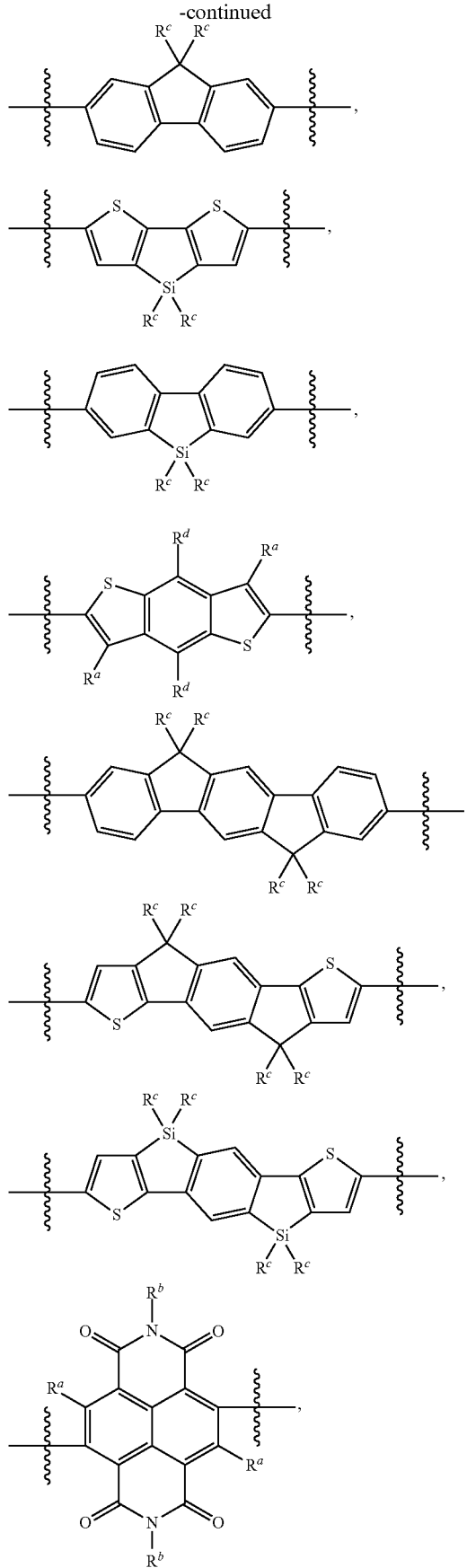
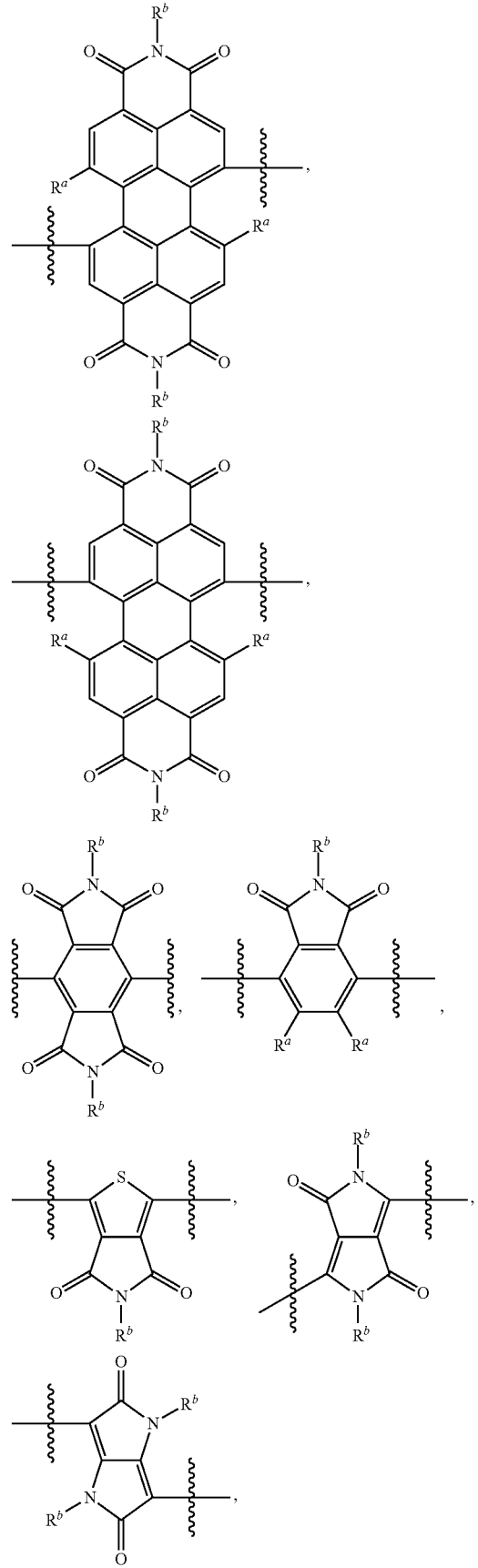

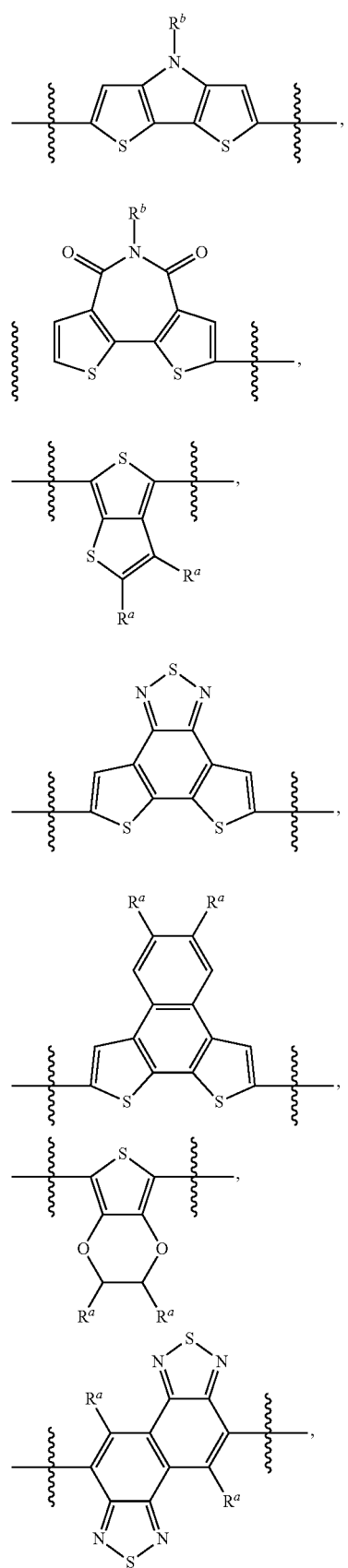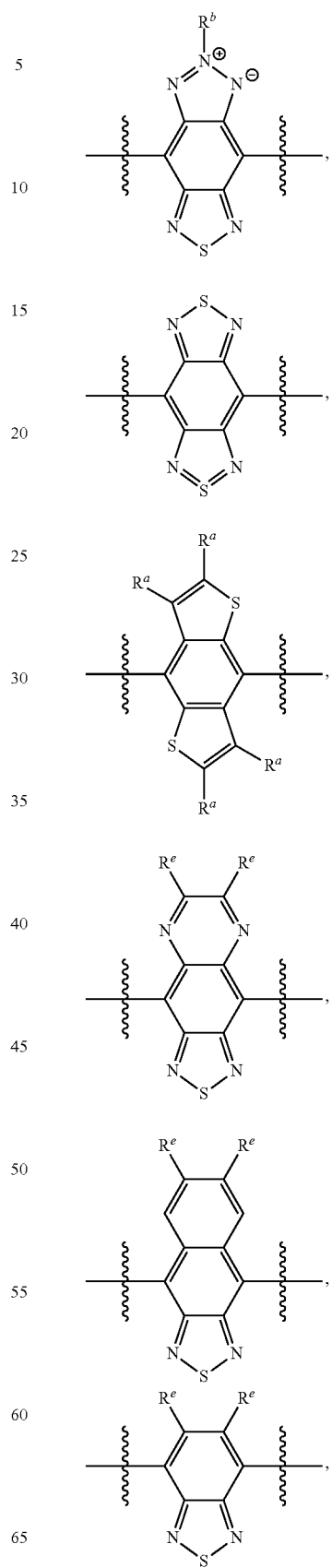

-continued

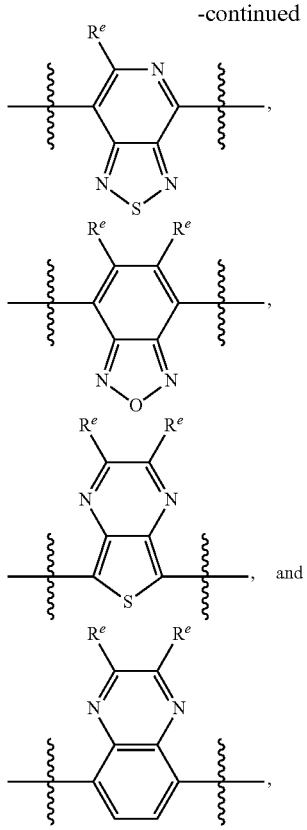

wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

8. The compound of claim 5, wherein Ar in $(Ar)_m$, $(Ar)_{m'}$, and $(Ar)_{m''}$ is represented by:

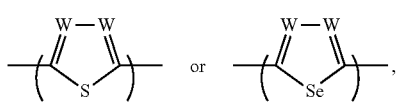

wherein each W independently is selected from N, CH, and $CR^4$, wherein $R^4$ is selected from F, Cl, —CN, R, OR, SR, C(O)R, OC(O)R, and C(O)OR, and wherein R is selected from a $C_{1-40}$ alkyl group, a $C_{2-40}$ alkenyl group, a $C_{2-40}$ alkynyl group, and a $C_{1-40}$ haloalkyl group.

9. The compound of claim 8, wherein $(Ar)_m$, $(Ar)_{m'}$, and $(Ar)_{m''}$ independently are selected from:

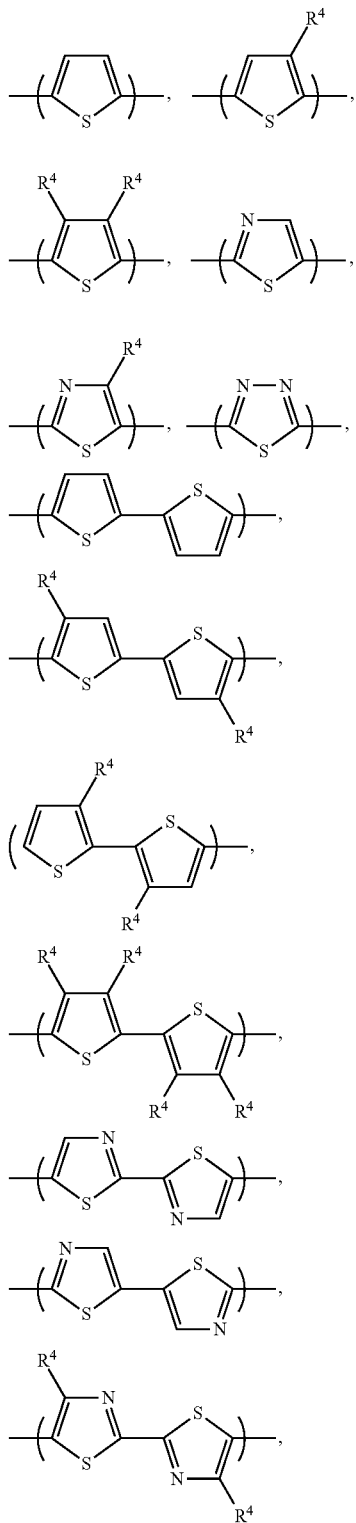

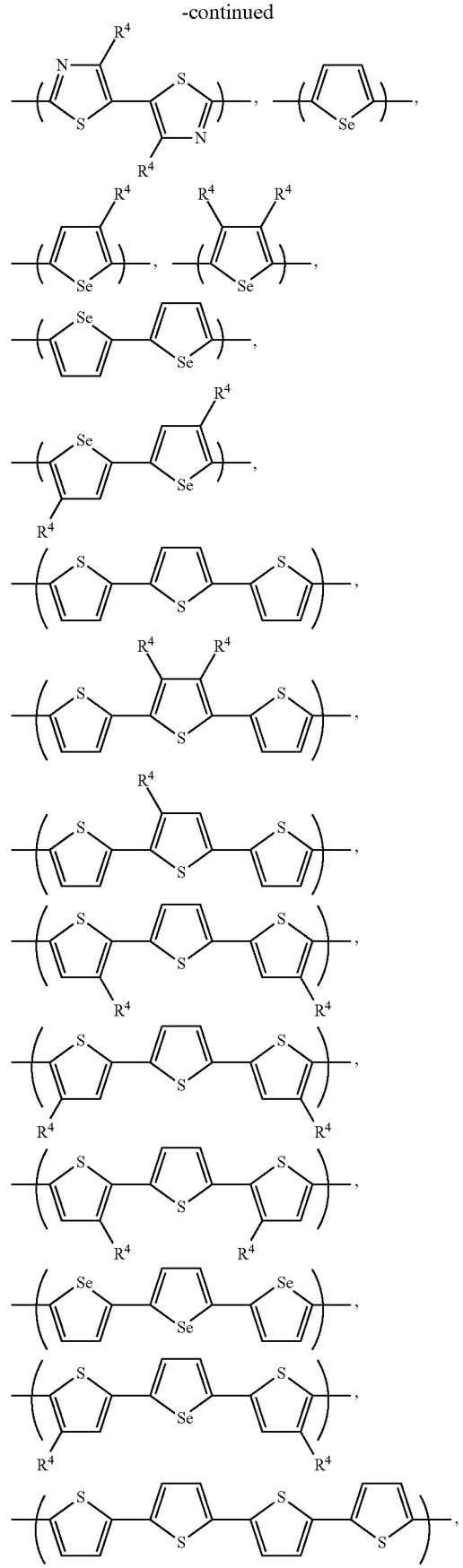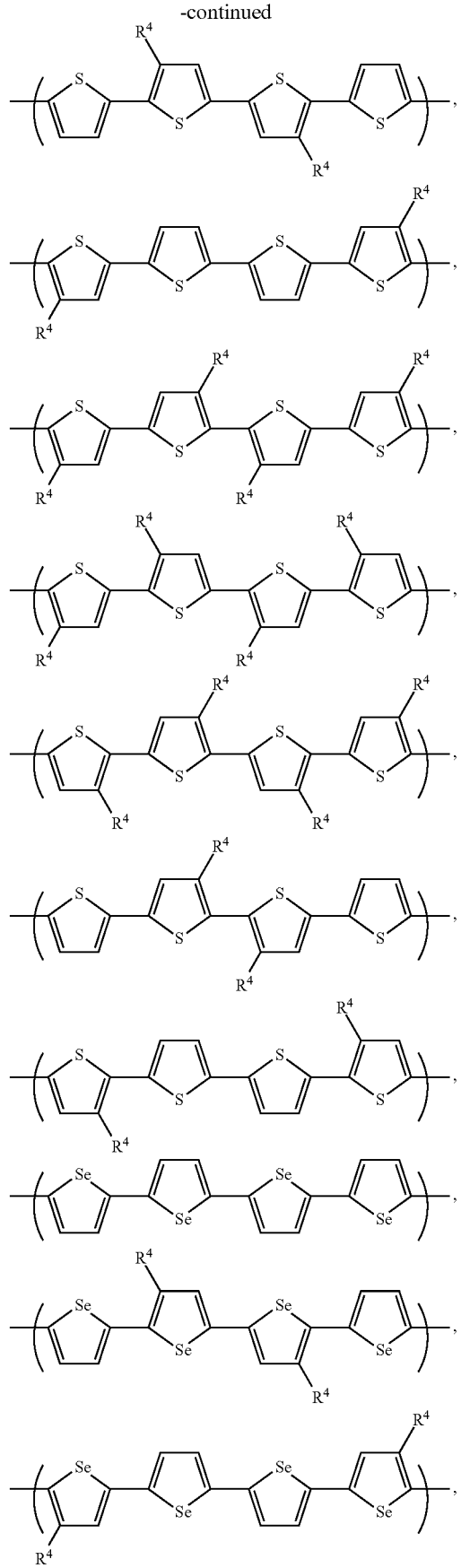

-continued

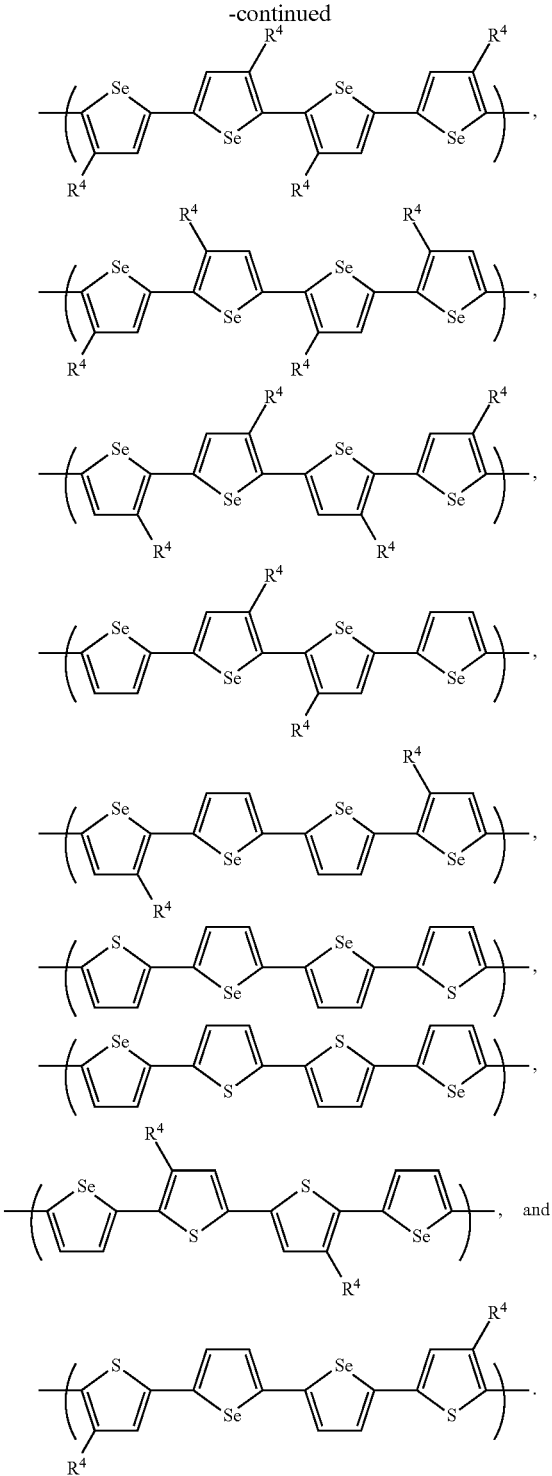

10. The compound of claim 5, wherein Z is selected from:

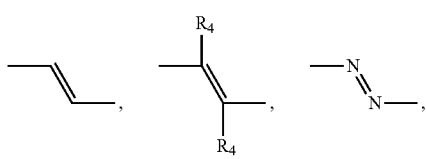

-continued

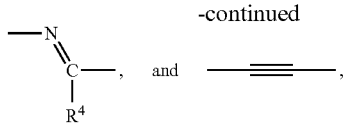

wherein $R^4$ is selected from F, Cl, —CN, R, OR, SR, C(O)R, OC(O)R, and C(O)OR, and wherein R is selected from a $C_{1-40}$ alkyl group, a $C_{2-40}$ alkenyl group, a $C_{2-40}$ alkynyl group, and a $C_{1-40}$ haloalkyl group.

11. The compound of claim 4, further comprising one or more repeating units other than $M_1$, the one or more other repeating units ($M_2$) being selected from:

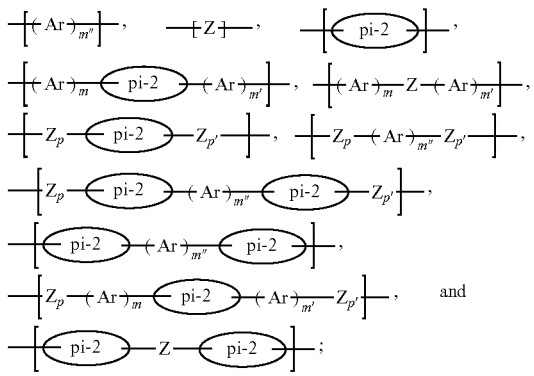

wherein:
pi-2 is an optionally substituted conjugated polycyclic moiety other than an optionally substituted bithiophene sulfonamide moiety;
Ar, at each occurrence, is independently an optionally substituted 5- or 6-membered aryl or heteroaryl group;
Z is a conjugated noncyclic linker;
m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

12. The compound of claim 11, wherein:
Z is selected from the group consisting of:

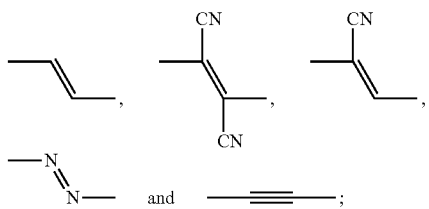

$(Ar)_m$ $(Ar)_{m'}$, and $(Ar)_{m''}$ independently are selected from the group consisting of:

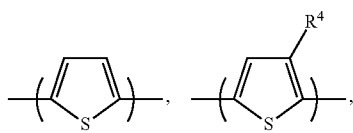

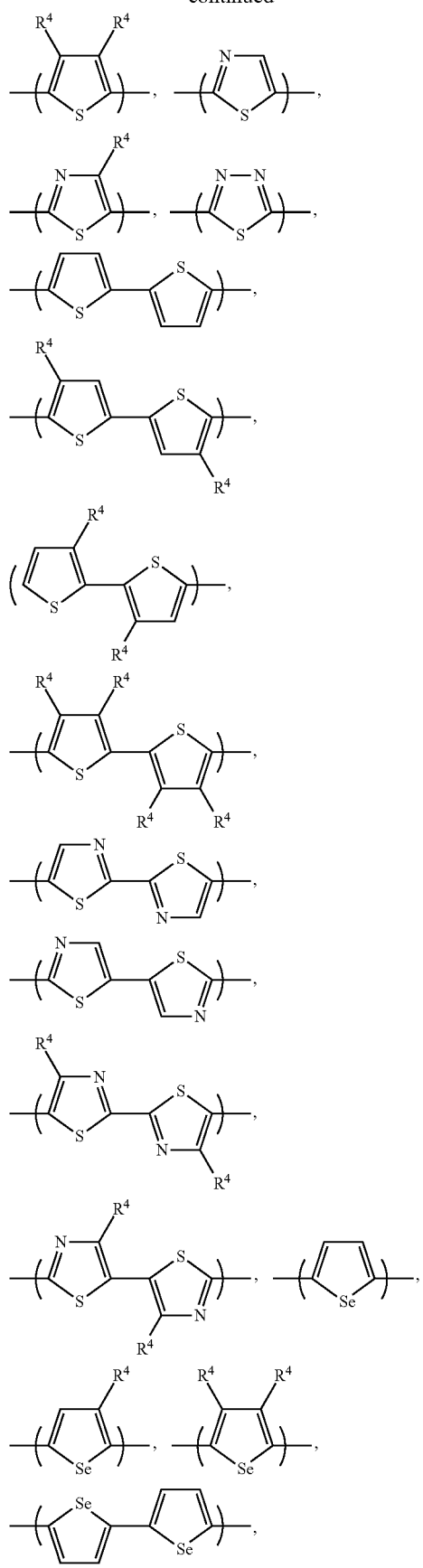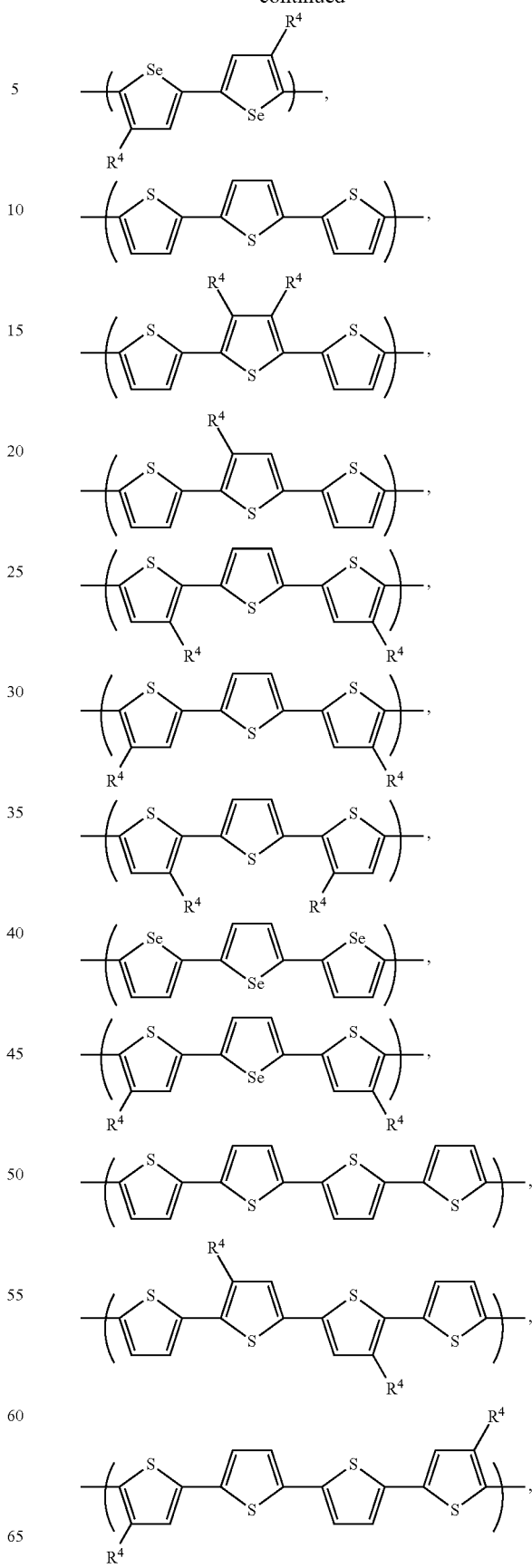

-continued
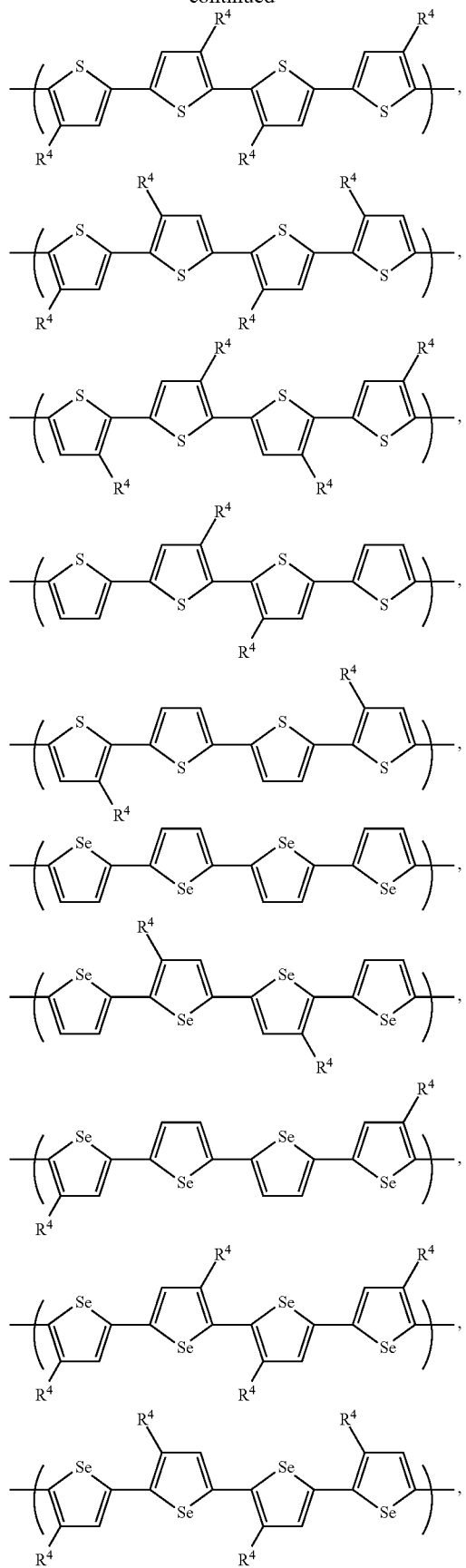
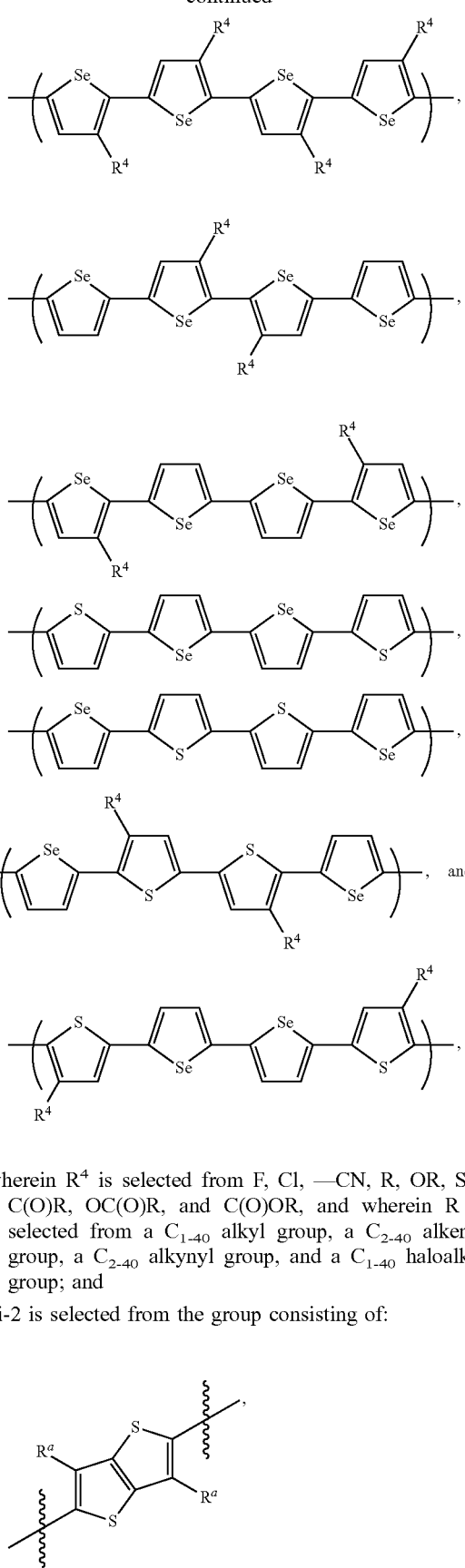
wherein R⁴ is selected from F, Cl, —CN, R, OR, SR, C(O)R, OC(O)R, and C(O)OR, and wherein R is selected from a $C_{1-40}$ alkyl group, a $C_{2-40}$ alkenyl group, a $C_{2-40}$ alkynyl group, and a $C_{1-40}$ haloalkyl group; and
pi-2 is selected from the group consisting of:
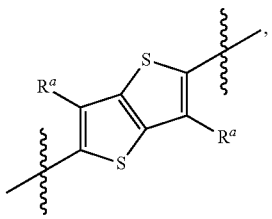

127
-continued
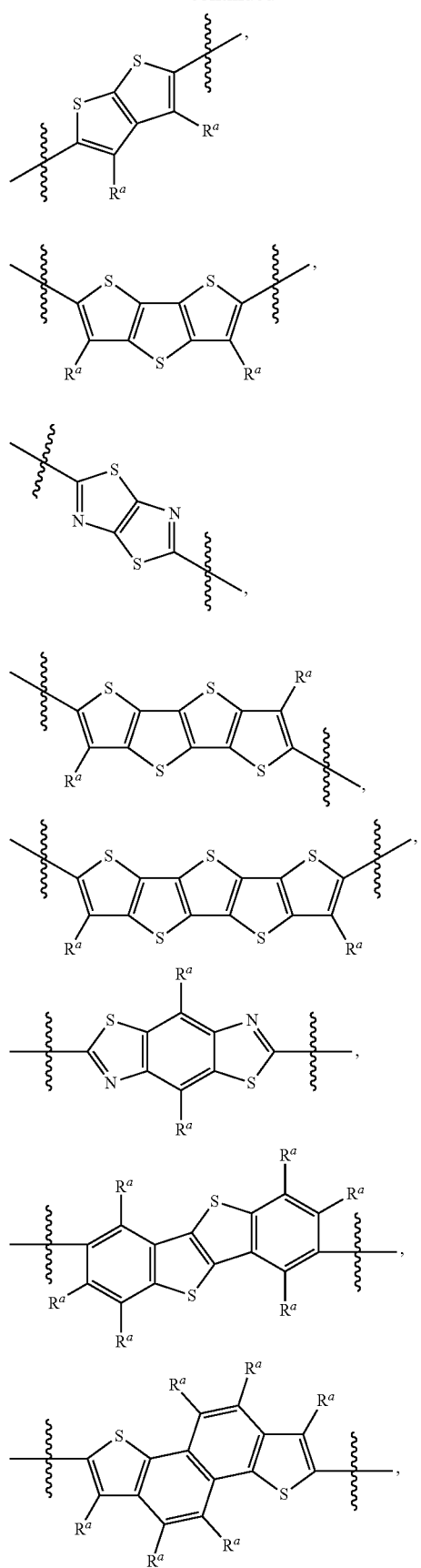
128
-continued
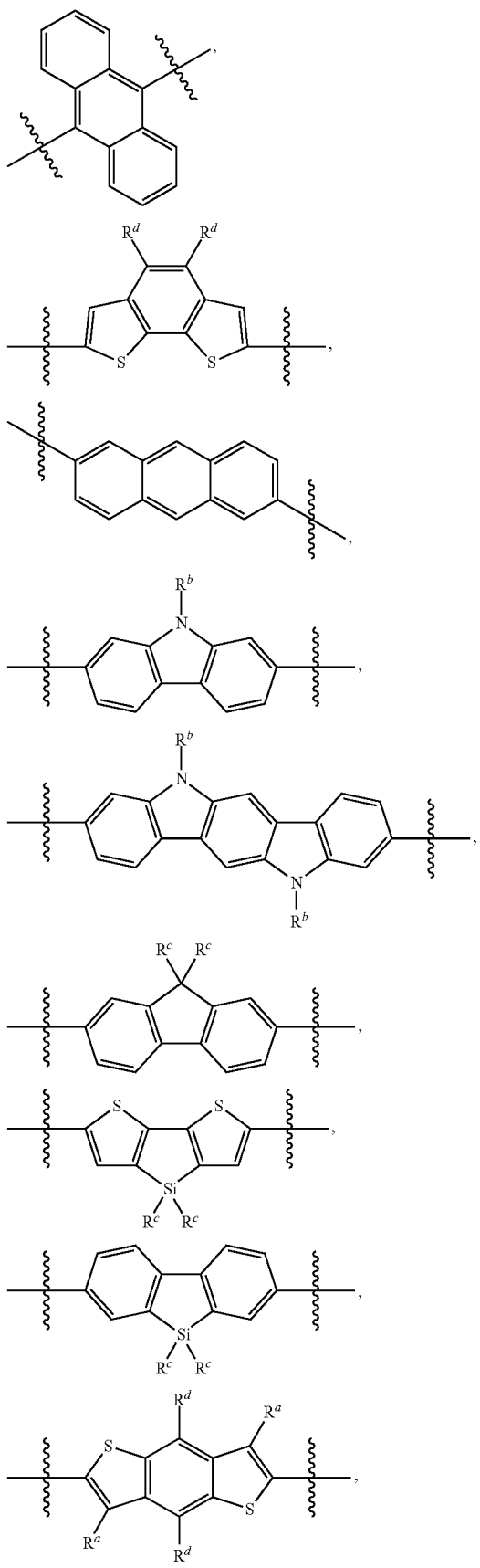

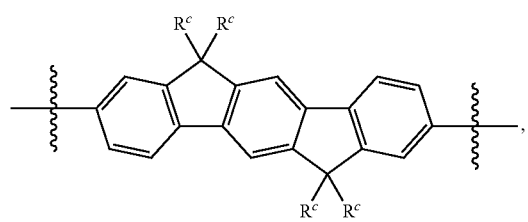
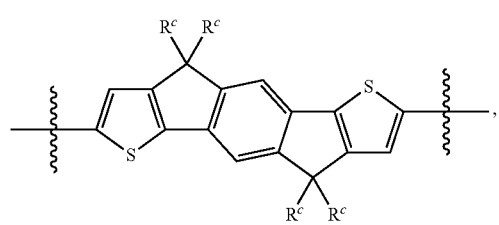
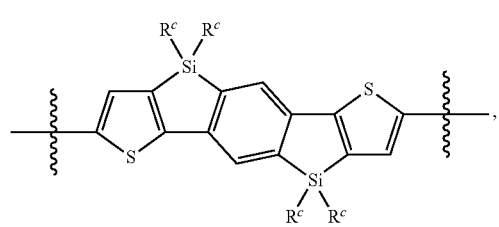
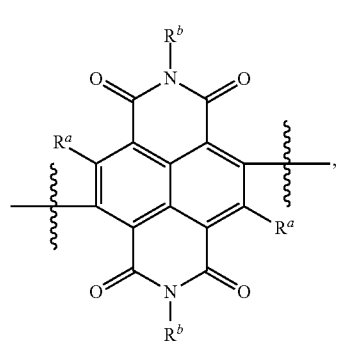
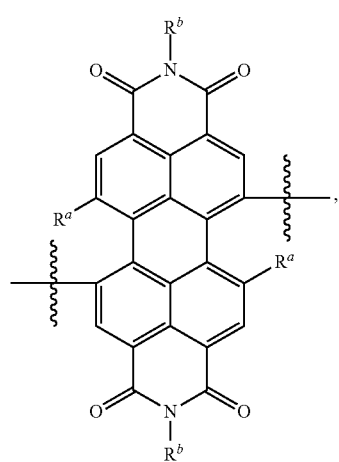
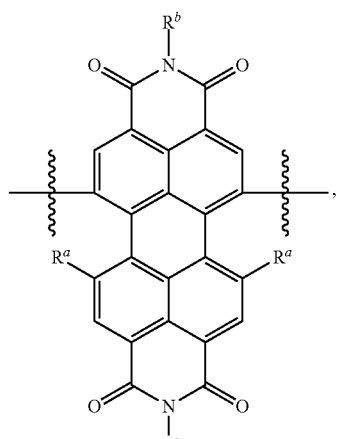
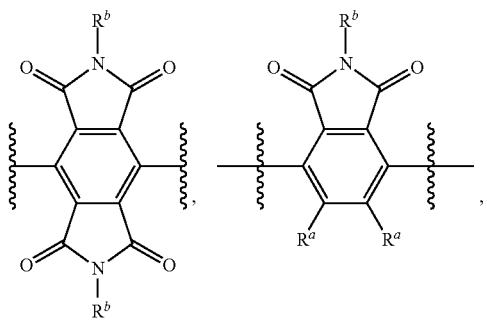
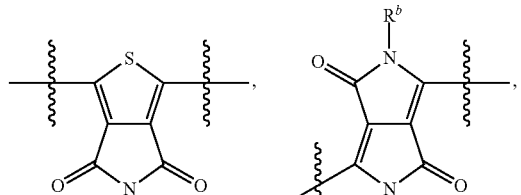
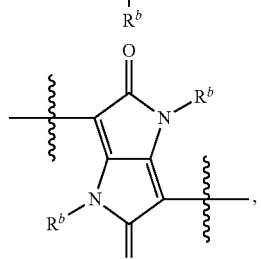
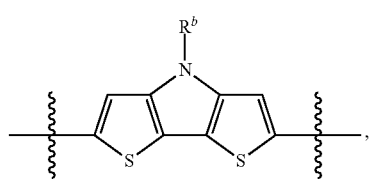
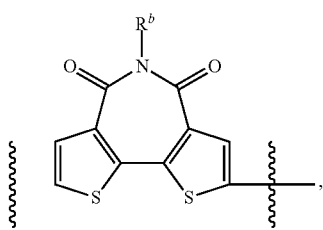

131
-continued
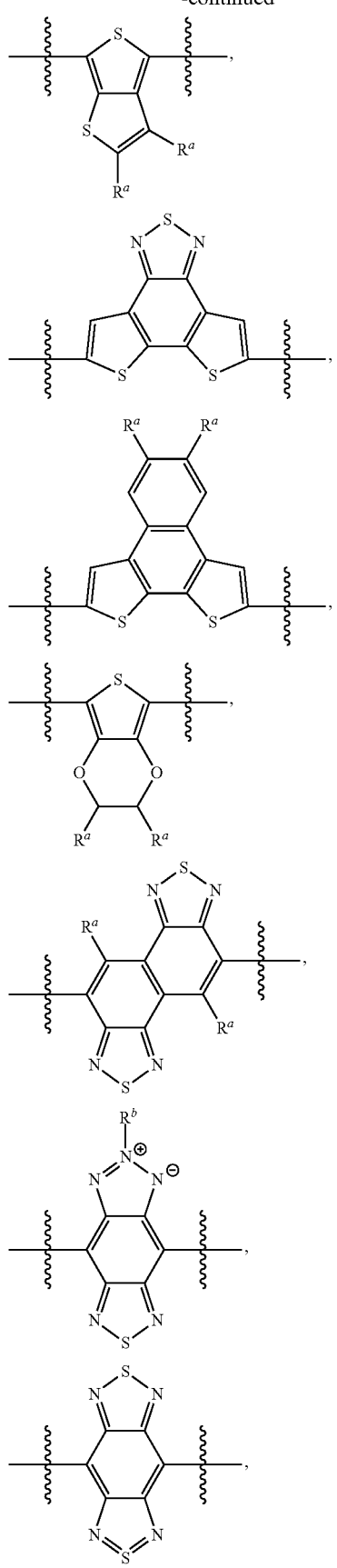
132
-continued
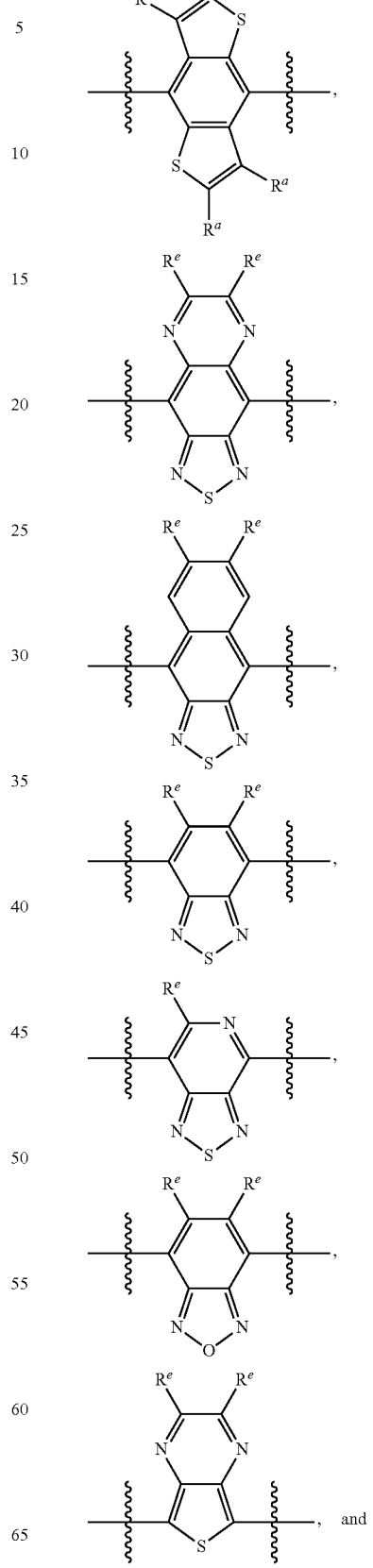

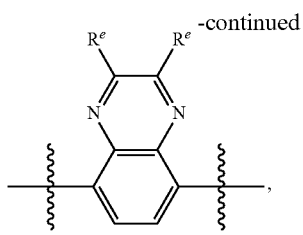

wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$; and $R^e$ is selected from the group consisting of H, F, Cl, —CN, R, —OR, —SR, —C(O)R, —OC(O)R, —C(O)OR, and $R^f$; wherein $R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group; and R is selected from the group consisting of a $C_{1-40}$ alkyl group, a $C_{1-40}$ haloalkyl group, a $C_{2-40}$ alkenyl group, and a $C_{2-40}$ alkynyl group.

13. The compound of claim 12, wherein $M_1$ is selected from the group consisting of:

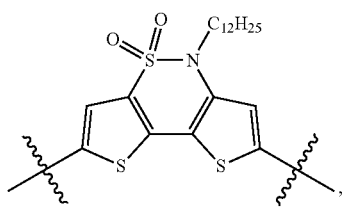

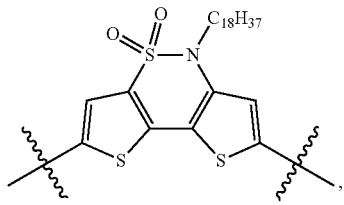

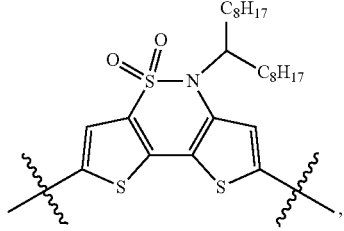

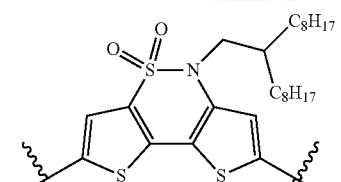

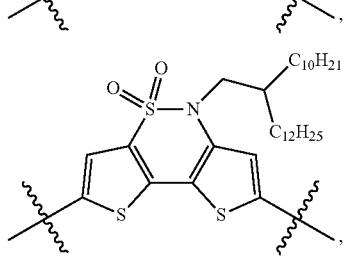

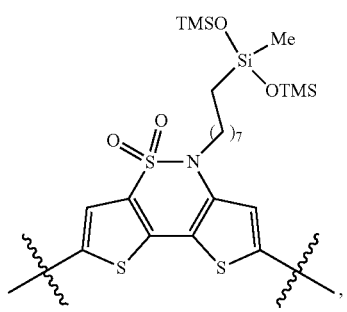

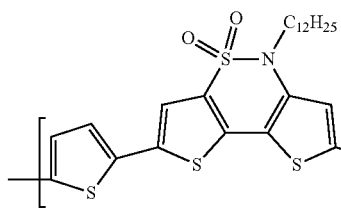

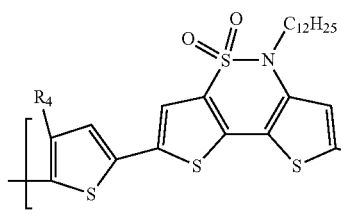

$M_2$ is selected from the group consisting of:

, 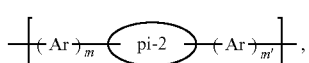, and

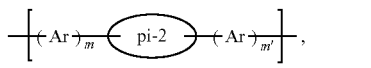

wherein $(Ar)_m$ and $(Ar)_{m'}$ are selected from:

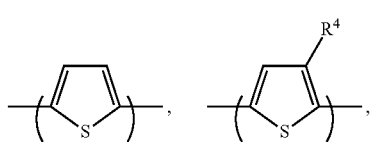

-continued

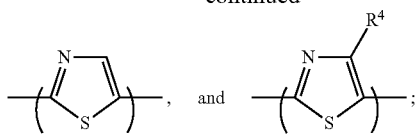

and R[4] is selected from the group consisting of F, Cl, —CN, R, OR, SR, C(O)R, OC(O)R, and C(O)OR; wherein R is selected from the group consisting of a $C_{1-40}$ alkyl group, a $C_{2-40}$ alkenyl group, a $C_{2-40}$ alkynyl group, and a $C_{1-40}$ haloalkyl group.

14. The compound of claim 11, wherein the compound is a copolymer having a formula selected from the group consisting of:

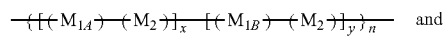

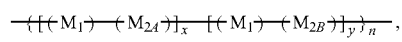

wherein $M_{1A}$ and $M_{1B}$ represent different repeating units having the formula $M_1$, and $M_{2A}$ and $M_{2B}$ represent different repeating units having the formula $M_2$, x and y are real numbers representing molar ratios, and n is the degree of polymerization.

15. The compound of claim 1, wherein the compound has a formula selected from the group consisting of:

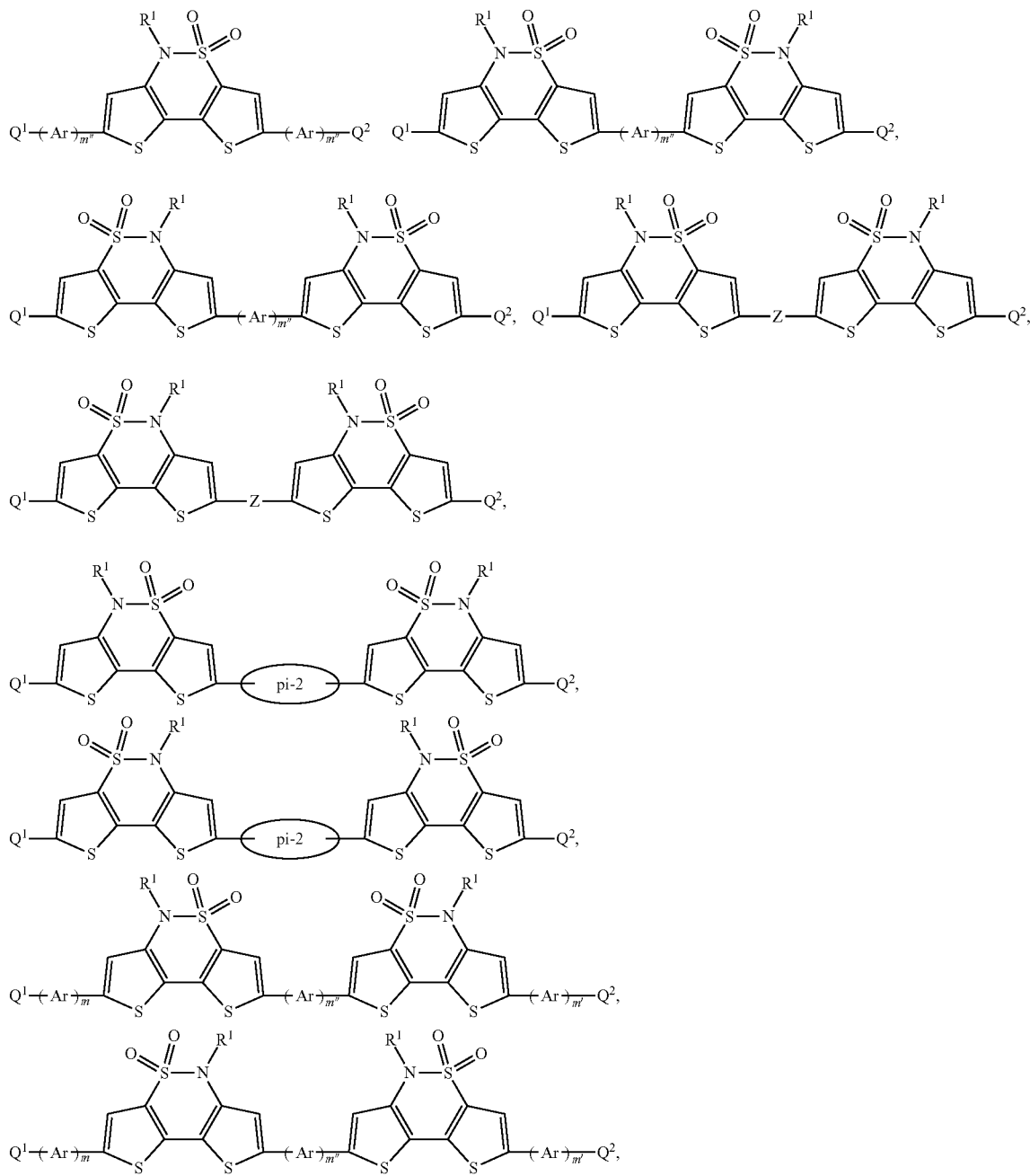

-continued

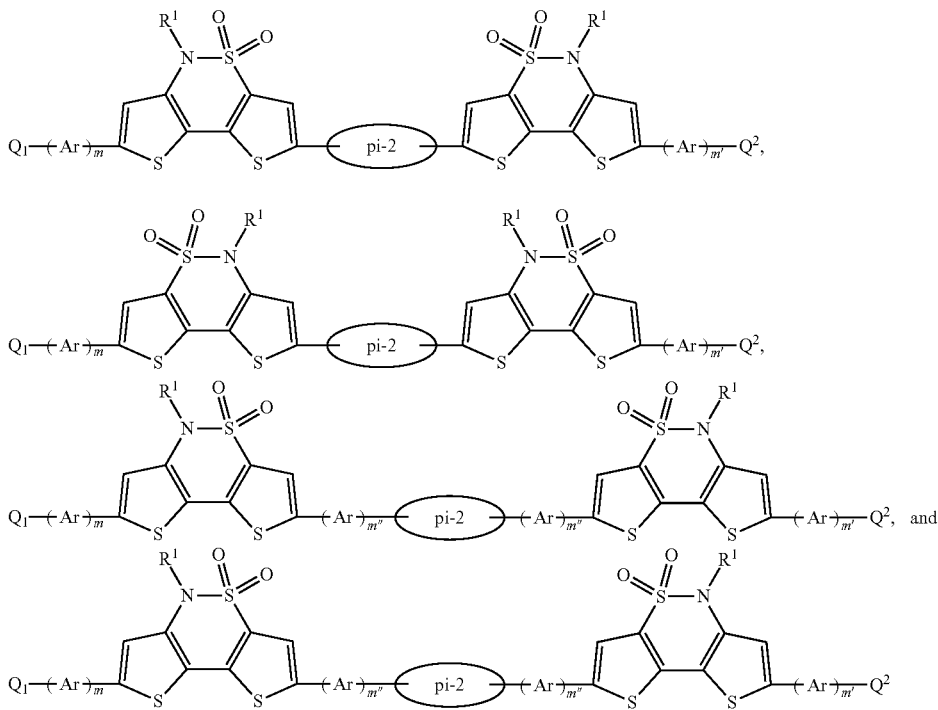

wherein:
Q¹ and Q² independently are selected from the group consisting of H, R, and C(O)R, wherein R is a $C_{1-40}$ alkyl or haloalkyl group;
pi-2 is an optionally substituted conjugated polycyclic moiety other than an optionally substituted bithiophene sulfonamide moiety;
Ar, at each occurrence, is independently an optionally substituted 5- or 6-membered aryl or heteroaryl group;

Z is a conjugated noncyclic linker;
m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

16. The compound of claim 15, wherein the compound is represented by a formula selected from the group consisting of:

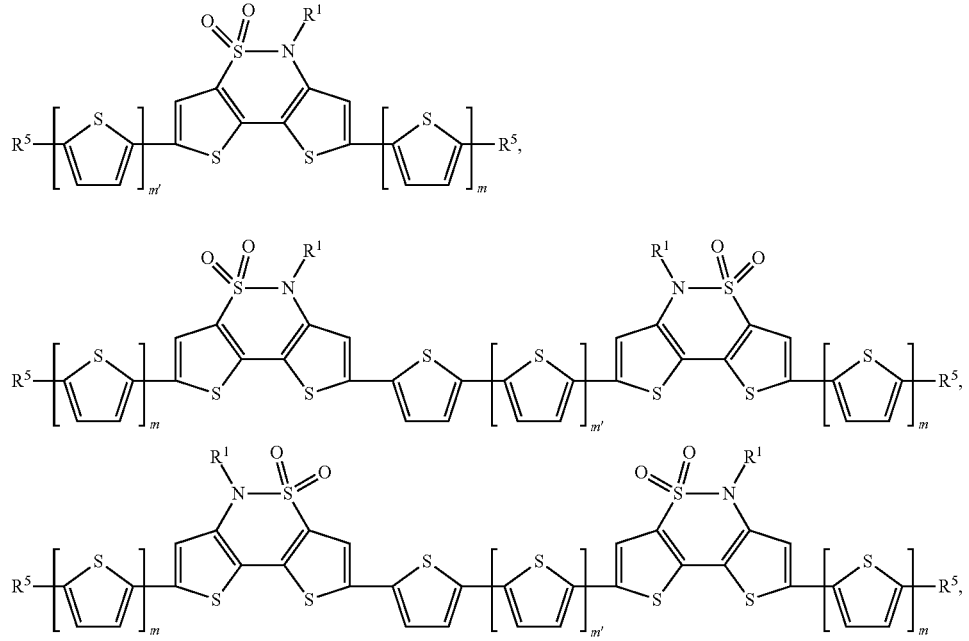

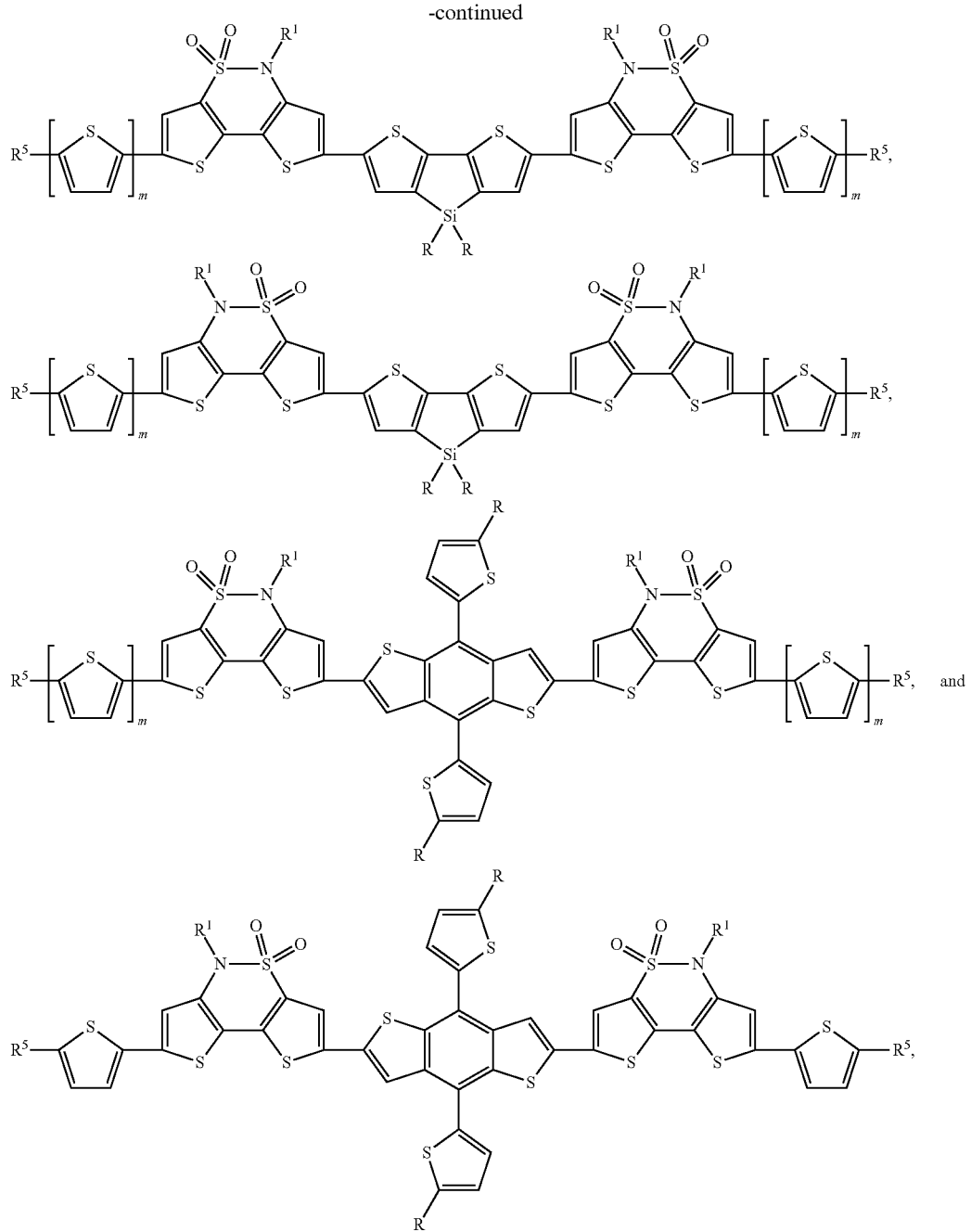
wherein R⁵ is H or R.
* * * * *